US006797467B1

(12) United States Patent
Murphy et al.

(10) Patent No.: US 6,797,467 B1
(45) Date of Patent: *Sep. 28, 2004

(54) COMPOSITIONS AND METHODS FOR DETERMINING INTERACTIONS OF MITOCHONDRIAL COMPONENTS, AND FOR IDENTIFYING AGENTS THAT ALTER SUCH INTERACTIONS

(75) Inventors: Anne N. Murphy, Encinitas, CA (US); William Clevenger, Oceanside, CA (US); Sandra Eileen Wiley, San Diego, CA (US); Alexander Y. Andreyev, San Diego, CA (US); Luciano G. Frigeri, San Diego, CA (US); Gonul Velicelebi, San Diego, CA (US); Robert E. Davis, San Diego, CA (US)

(73) Assignee: MitoKor, Inc., San Diego, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 09/709,785

(22) Filed: Nov. 3, 2000

Related U.S. Application Data

(63) Continuation-in-part of application No. 09/434,354, filed on Nov. 3, 1999.

(51) Int. Cl.[7] .......................... C12Q 1/68; C12Q 1/00; G01N 33/53; A01N 47/28; C07H 21/04
(52) U.S. Cl. ................. 435/6; 435/4; 435/7.8; 435/26; 514/588; 536/22.1; 800/301
(58) Field of Search .................... 435/4, 6, 7.8, 26; 536/22.1; 514/588; 800/301

(56) References Cited

U.S. PATENT DOCUMENTS

| | | | |
|---|---|---|---|
| 5,447,852 A | 9/1995 | Friedman et al. | 435/69.7 |
| 5,523,227 A | 6/1996 | Bram et al. | 435/240.2 |
| 5,773,225 A | * 6/1998 | Luban | 435/7.8 |
| 5,780,235 A | 7/1998 | Bandman et al. | 435/6 |
| 5,968,802 A | 10/1999 | Wang et al. | 435/233 |
| 6,140,067 A | * 10/2000 | Anderson | 435/26 |
| 6,150,415 A | 11/2000 | Hammock et al. | 514/588 |
| 6,183,948 B1 | * 2/2001 | Marban | 435/4 |
| 6,211,440 B1 | * 4/2001 | Briggs | 800/301 |

FOREIGN PATENT DOCUMENTS

| | | |
|---|---|---|
| WO | WO 98/06737 | 2/1998 |
| WO | WO 98/19714 | 5/1998 |
| WO | WO 99/07845 | 2/1999 |
| WO | WO 00/26370 | 5/2000 |

OTHER PUBLICATIONS

Halestrap et al., "Elucidating the molecular mechanism of the—", *B. B. Acta*, (1998), vol. 1366, pp. 79–94.*
Adams et al., "Complementary DNA Sequencing: Expressed Sequence Tags and Human Genome Project," *Science* 252:1651–1656, 1991.
Allgood and Eastman, "Chimeric Receptors as Gene Switches," *Current Opinion in Biotechnology* 8:474–479, 1997.
Aquila et al., "Complete Amino Acid Sequence of the ADP/ATP Carrier from Beef Heart Mitochondria," *Hoppe–Seyler's Z. Physiol. Chem.* 363:345–349, 1982.
Battini et al., "Molecular Cloning of a cDNA for a Human ADP/ATP Carrier Which is Growth–Regulated," *The J. of Biological Chemistry* 262(9):4355–4359, 1987.
Bergsma et al., "The Cyclophilin Multigene Family of Peptidyl–Prolyl Isomerases," *The J. of Biological Chemistry* 266(34):23204–23214, 1991.
Bernardi et al., "Recent Progress on Regulation of the Mitochondrial Permeability Transition Pore; a Cyclosporin–Sensitive Pore in the Inner Mitochondrial Membrane," *J. of Bioenergetics and Biomembranes* 26(5):509–517, 1994.
Brunelli and Pall, "A Series of Yeast Shuttle Vectors for Expression of cDNAs and Other DNA Sequences," *Yeast* 9:1299–1309, 1993.
Cacalano et al., "Evidence for a Functional Receptor for Cyclosporin A on the Surface of Lymphocytes," *Proc. Natl. Acad. Sci. USA* 89:4353–4357, 1992.
Carra and Schleif, "Variation of Half–Site Organization and DNA Looping by AraC Protein," *The EMBO J.* 12(1):35–44, 1993.
Costantini et al., "On the Effects of Paraquat on Isolated Mitochondria. Evidence that Paraquat Causes Opening of the Cyclosporin A–Sensitive Permeability Transition Pore Synergistically with Nitric Oxide," *Toxicology* 99:77–88, 1995.
Cozens et al., "DNA Sequences of Two Expressed Nuclear Genes for Human Mitochondrial ADP/ATP Translocase," *J. Mol. Biol.* 206:261–280, 1989.
Crompton et al., "Cyclophilin–D Binds Strongly to Complexes of the Voltage–Dependent Anion Channel and the Adenine Nucleotide Translocase to form the Permeability Transition Pose," *Eur. J. Biochem.* 258:729–735, 1998.
Cruz–Orive and Weibel, "Recent Stereological Methods for Cell Biology: a Brief Survey," *Am. J. Physiol.* 258:L148–L156, 1990.
Ernster and Schatz, "Mitochondria: A Historical Review," *J. Cell. Biol.* 91(3):227s–255s, 1981.
Fiore et al., "The Mitochondrial ADP/ATP Carrier: Structural, Physiological and Pathological Aspects," *Biochimie* 80:137–150, 1998.

(List continued on next page.)

Primary Examiner—Ethan Whisenant
Assistant Examiner—Arun Kr. Chakrabarti
(74) Attorney, Agent, or Firm—SEED Intellectual Property Law Group PLLC

(57) ABSTRACT

Compositions and methods are provided for identifying agents that alter mitochondrial membrane permeability transition. The screening methods generally detect agents that alter the interaction between the mitochondrial adenine nucleotide translocator and cyclophilin D. Such agents may be used, for example, in the treatment of a variety of conditions associated with altered mitochondrial function.

17 Claims, 14 Drawing Sheets

OTHER PUBLICATIONS

Fischer and Schmid, "The Mechanism of Protein Folding. Implications of in Vitro Refolding Models for de Novo Protein Folding and Translocation in the Cell," *Biochemistry* 29(9):2205–2212, 1990.

Franke and Luban, "Cyclophilin and GAG in HIV–1 Replication and Pathogenesis," *Advances in Experimental Medicine and Biology* 374:217–228, 1995.

Galat, "Peptidylproline Cis–Trans–Isomerases: Immunophilins," *Eur. J. Biochem.* 216:689–707, 1993.

GenBank Acc. No. AA490268, Jun. 25, 1997.
GenBank Acc. No. AA874983, Mar. 20, 1998.
GenBank Acc. No. AA955975, May 7, 1998.
Genbank Acc. No. AAA58434, Dec. 31, 1994.
GenBank Acc. No. AAB08453, Sep. 18, 1996.
GenBank Acc. No. AF020338, Sep. 24, 1997.
GenBank Acc. No. AF039571, Feb. 2, 1999.
GenBank Acc. No. AF178950, Oct. 20, 1999.
GenBank Acc. No. AF178951, Oct. 20, 1999.
GenBank Acc. No. AF178952, Oct. 20, 1999.
GenBank Acc. No. AI668824, May 14, 1999.
GenBank Acc. No. AI875905, Jul. 21, 1999.
GenBank Acc. No. AI892042, Jul. 27, 1999.
GenBank Acc. No. L06132, Jan. 14, 1995.
GenBank Acc. No. L06328, Jan. 14, 1995.
GenBank Acc. No. L21950, May 20, 1994.
GenBank Acc. No. L21951, May 20, 1994.
GenBank Acc. No. M34907, Apr. 27, 1993.
GenBank Acc. No. M36035, Dec. 20, 1993.
GenBank Acc. No. M80254, Dec. 31, 1994.
GenBank Acc. No. N86710, Apr. 1, 1996.
GenBank Acc. No. NM_003374, Nov. 1, 2000.
GenBank Acc. No. NM_003375, Nov. 1, 2000.
GenBank Acc. No. NM_004758, Nov. 1, 2000.
GenBank Acc. No. NM_005038, Nov. 1, 2000.
GenBank Acc. No. NM_005662, Nov. 1, 2000.
GenBank Acc. No. S75494, Apr. 5, 1999.
GenBank Acc. No. S75651, Jul. 27, 1995.
GenBank Acc. No. U04335, Nov. 8, 1994.
GenBank Acc. No. U17900, Jan. 12, 1999.
GenBank Acc. No. U50388, Oct. 31, 1996.
GenBank Acc. No. U50389, Oct. 31, 1996.
GenBank Acc. No. U68544, Sep. 18, 1996.
GenBank Acc. No. U70314, Feb. 11, 1998.
GenBank Acc. No. U89987, Oct. 4, 2000.
GenBank Acc. No. U89988, Oct. 4, 2000.
GenBank Acc. No. U89989, Oct. 4, 2000.
GenBank Acc. No. X62123, Jun. 8, 1994.
GenBank Acc. No. Z82214, Dec. 12, 1999.

Giraud et al., "Expression of Human ANT2 Gene in Highly Proliferative Cells: GRBOX, a New Transcriptional Element, Is Involved in the Regulation of Glycolytic ATP Import into Mitochondria," *J. Mol. Biol.* 281:409–418, 1998.

Green and Reed, "Mitochondria and Apoptosis," *Science* 281:1309–1312, Aug. 28, 1998.

Griffin et al., "Specific Covalent Labeling of Recombinant Protein Molecules Inside Live Cells," *Science* 281:269–272, 1998.

Guzman et al., "Tight Regulation, Modulation, and High–Level Expression by Vectors Containing the Arabinose $P_{BAD}$ Promotor," *J. of Bacteriology* 177(14):4121–4130, 1995.

Haendler et al., "Complementary DNA for human T–cell cyclophilin," *The EMBO J.* 6(4):947–950, 1987.

Haldimann et al., "Use of New Methods for Construction of Tightly Regulated Arabinose and Rhamnose Promoter Fusions in Studies of the *Escherichia coli* Phosphate Regulon," *J. of Bacteriology* 180(5):1277–1286, 1998.

Halestrap et al., "Cyclosporin A Binding to Mitochondrial Cyclophilin Inhibits the Permeability Transition Pore and Protects Hearts from Ischaemia/Reperfusion Injury," *Molecular and Cellular Biochemistry* 174:167–172, 1997.

Halestrap et al., "Elucidating the Molecular Mechanism of the Permeability Transition Pore and its Role in Reperfusion Injury of the Heart," *Biochimica et. Biophysica Acta* 1366:79–94, 1998.

Halestrap et al., "Mitochondrial Calcium Handling and Oxidative Stress," *Biochemical Society Transactions* 21(2):353–358, 1993.

Holloway and Bram, "Co–localization of Calcium–Modulating Cyclophilin Ligand with Intracellular Calcium Pools," *The J. of Biological Chemistry* 273(26):16346–16350, 1998.

Hunter and Haworth, "The $Ca^{2+}$–Induced Membrane Transition in Mitochondria: The Protective Mechanisms," *Archives of Biochemistry and Biophysics* 195(2):453–459, 1979.

Jäschke et al., "Human T Cell Cyclophilin18 Binds to Thiol–Specific Antioxidant Protein Aop1 and Stimulates its Activity," *J. Mol. Biol.* 277:763–769, 1998.

Jürgensmeier et al., "Bax Directly Induces Release of Cytochrome c From Isolated Mitochondria," *Proc. Natl. Acad. Sci.* 95:4997–5002, 1998.

Kamo et al., "Membrane Potential of Mitochondria Measured with an Electrode Sensitive to Tetraphenyl Phosphonium and Relationship Between Proton Electrochemical Potential and Phosphorylation Potential in Steady State," *J. Membrane Biol.* 49:105–121, 1979.

Kendall and Badminton, "*Aequorea victoria* Bioluminescence Moves into an Exciting New Era," *Biotechnology* 16:216–224, 1998.

Klingenberg et al., "Isolation of the ADP, ATP Carrier as the Carboxyatractylate Protein Complex from Mitochondria," *Biochimica et Biophysica Acta* 503:193–210, 1978.

Korfron et al., "Determination of Kinetic Constants for Peptidyl Prolyl Cis–Trans Isomerases by an Improved Spectrophotometric Assay," *Biochemistry* 30:6127–6134, 1991.

Kroemer et al., "The Mitochondrial Death/Life Regulator in Apoptosis and Necrosis," *Annu. Rev. Physiol.* 60:619–642, 1998.

Ku et al., "The Human Fibroblast Adenine Nucleotide Translocator Gene: Molecular Cloning and Sequence," *The J. of Biological Chemistry* 265(27):16060–16063, 1990.

Li et al., "A Human Muscle Adenine Nucleotide Translocator Gene Has Four Exons, is Located on Chromosome 4, and is Differentially Expressed," *The J. of Biological Chemistry* 264(24):13998–14004, 1989.

Lutz and Bujard, "Independent and Tight Regulation of Transcriptional Units in *Escherichia coli* Via the LacR/O, the TetR/O and AraC/$I_1$–$I_2$ Regulatory Elements," *Nucleic Acids Research* 25(6):1203–1210, 1997.

Mahajan et al., "Bcl–2 and Bax Interactions in Mitochondria Probed with Green Fluorescent Protein and Fluorescence Resonance Energy Transfer," *Nature Biotechnology* 16:547–552, 1998.

Makrides, "Strategies for Achieving High–Level Expression of Genes in *Escherichia coli,*" *Microbiological Reviews* 60(3):512–538, 1996.

Mancini et al., "Flow Cytometric Measurement of Mitochondrial Mass and Function: A Novel Method for Assessing Chemoresistance," *Ann. Surg. Oncol.* 5(3):287–295, 1998.

Mancini et al., "Mitochondrial Proliferation and Paradoxical Membrane Depolarization During Terminal Differentiation and Apoptosis in a Human Colon Carcinoma Cell Line," *The J. of Cell Biology* 138(2):449–469, 1997.

Marzo et al., "The Permeability Transition Pore Complex: A Target for Apoptosis Regulation by Caspases and Bcl–2–Related Proteins," *J. Exp. Med.* 187(8):1261–1271, 1998.

Mayer, "A New Set of Useful Cloning and Expression Vectors Derived From pBlueScript," *Gene* 163:41–46, 1995.

Murphy and Bredesen, *Mitochondria & Free Radicals in Neurodegenerative Diseases*, Wiley–Liss, New York, Chapter 8, "Mitochondria, Reactive Oxygen Species, and Apoptosis," pp. 159–186.

Neckelmann et al., "cDNA Sequence of a Human Skeletal Muscle ADP/ATP Translocator: Lack of a Leader Peptide, Divergence from a Fibroblast Translocator cDNA, and Coevolution with Mitochondrial DNA Genes," *Proc. Natl. Acad. Sci. USA* 84:7580–7584, 1987.

Nicolli et al., "Interactions of Cyclophilin with the Mitochondrial Inner Membrane and Regulations of the Permeability Transition Pore, a Cyclosporin A–Sensitive Channel," *The Journal of Biological Chemistry* 271(4):2185–2192, 1996.

Petit et al., "Disruption of the Outer Mitochondrial Membrane as a Result of Large Amplitude Swelling: The Impact of Irreversible Permeability Transition," *FEBS Letters* 426:111–116, 1998.

Porter and Brand, "Causes of Differences in Respiration Rate of Hepatocytes from Mammals of Different Body Mass," *American J. of Physiology: Regulatory, Integrative and Comparative Physiology* 38(5):R1213–R1224, 1995.

Price et al., "Human Cyclophilin B: A Second Cyclophilin Gene Encodes a Peptidyl–Prolyl Isomerase with a Signal Sequence," *Proc. Natl. Acad. Sci. USA* 88:1903–1907,1991.

Ratajczak et al., "The Cyclophilin Component of the Unactivated Estrogen Receptor Contains a Tetratricopeptide Repeat Domain and Shares Identity with p59 (FKBP59)," *The J. of Biological Chemistry* 268(18):13187–13192, 1993.

Schwerzmann et al., "Molecular Architecture of the Inner Membrane of Mitochondria from Rat Liver: A Combined Biochemical and Stereological Study," *The J. of Cell Biology* 102(1):97–103, 1986.

Shinohara et al., "Isolation and Characterization of cDNA Clones and a Genomic Clone Encoding Rat Mitochondrial Adenine Nucleotide Translocator," *Biochimica et Biophysica Acta* 1152:192–196, 1993.

Stamnes et al., "The Cyclophilin Homolog ninaA is a Tissue–Specific Integral Membrane Protein Required for the Proper Synthesis of a Subset of Drosophila Rhodopsins," *Cell* 65:219–227, 1991.

Stepien et al., "Differential Expression of Adenine Nucleotide Translocator Isoforms in Mammalian Tissues and During Muscle Cell Differentiation," *The J. of Biological Chemistry* 267(21):14592–14597, 1992.

Sterling, "Direct Thyroid Hormone Activation of Mitochondria: The Role of Adenine Nucleotide Translocase," *Endocrinology* 119(1):292–295, 1986.

Streicher–Scott et al., "Use of Carboxyatractylate and Tight–Binding Inhibitor Theory to Determine the Concentration of Functional Mitochondrial Adenine Nucleotide Translocators in a Reconstituted System," *Analytical Biochemistry* 210(1):69–76, 1993.

Susin et al., "Mitochondria as Regulators of Apoptosis: Doubt No More," *Biochimica et Biophysica Acta* 1366:151–165, 1998.

Swanson et al., "Cyclosporin–Mediated Inhibition of Bovine Calcineurin by Cyclophilins A and B," *Proc. Natl. Acad. Sci. USA* 89:3741–3745, 1992.

Taylor et al., "Structures of Cyclophilin–Ligand Complexes," *Prog. Biophys. Molec. Biol.* 67(2/3):155–181, 1997.

Vayssière et al., "Participation of the Mitochondrial Genome in the Differentiation of Neuroblastoma Cells," *In Vitro Cell. Dev. Biol.* 28A:763–772, 1992.

Wallace et al., *Mitochondria & Free Radicals in Neurodegenerative Diseases*, Wiley–Liss, New York, 1998, Chapter 13, "Mitochondrial Defects in Neurodegenerative Diseases and Aging," pp. 283–307.

Walsh et al., "Cyclosporin A, the Cyclophilin Class of Peptidylprolyl Isomerases, and Blockade of T Cell Signal Transduction," *The J. of Biological Chemistry* 267(19), 13115–13118, 1992.

White and Reynolds, "Mitochondrial Depolarization in Glutamate–Stimulated Neurons: An Early Signal Specific to Excitotoxin Exposure," *The J. of Neuroscience* 16(18):5688–5697, 1996.

Woodfield et al., "Direct Demonstration of a Specific Interaction Between Cyclophilin–D and the Adenine Nucleotide Translocase Confirms Their Role in the Mitochondrial Permeability Transition," *Biochem. J.* 336:287–290, 1998.

Wu et al., "Nup358, a Cytoplasmically Exposed Nucleoporin with Peptide Repeats, Ran–GTP Binding Sites, Zinc Fingers, a Cyclophilin A Homologous Domain, and a Leucine–rich Region," *The J. of Biological Chemistry* 270(23):14209–14213, 1995.

Xu et al., "Detection of Programmed Cell Death Using Fluorescence Energy Transfer," *Nucleic Acids Research* 26(8):2034–2035, 1998.

Zoratti and Szabò, "The Mitochondrial Permeability Transition," *Biochimica et Biophysica Acta* 1241:139–176, 1995.

Saito et al., "Expression of a Gene for Cyclophilin Which Contains an Amino–Terminal Endoplasmic Reticulum–Targeting Signal," *Plant Cell Physiol.* 40(1):77–87, 1999.

Smagula and Douglas, "ADP–ATP Carrier of *Saccharomyces cerevisiae* Contains a Mitochondrial Import Signal Between Amino Acids 72 and 111," *Journal of Cellular Biochemistry* 36:323–327, 1988.

Yang and Cortopassi, "dATP Causes Specific Release of Cytochrome C from Mitochondria," *Biochemical and Biophusical Research Communications* 250:454–457, 1998.

* cited by examiner

```
ANT1m  ATGGGTGATCACGCTTGGAGCTTCCTAAAGGACTTCCTGGCCGGGGCGGTCGCCGCTGCCGTCTCCAAGACCGCGGTCGC   80
ANT2m  ATGACAGATGCCGCTGTGTCCTTCGCCAAGGACTTCCTGGCAGGTGGAGTGGCCGCAGCCATCTCCAAGACGGCGGTAGC   80
ANT3m  ATGACGGAACAGGCCATCTCCTTCGCCAAAGACTTCTTTGGCCGGAGGCATCGCCGCCGCCATCTCCAAGACGGCCGTGGC   80

ANT1m  CCCCATCGAGAGGGTCAAAACTGCTGCTGCAGGTCCAGCATGCCAGCAAACAGATCAGTGCTGAGAAGCAGTACAAAGGGA  160
ANT2m  GCCCATCGAGCGGGTCAAGCTGCTGCTGCAGGTGCAGCATGCCAGCAAGCAGATCACTGCAGATAAGCAATACAAAGGCA  160
ANT3m  TCCGATCGAGCGGGTCAAGCTGCTGCTGCAGGTCCAGCACGCCAGCAAGCAGATCGCCGCCGACAAGCAGTACAAGGGCA  160

ANT1m  TCATTGATTGTGTGGTGAGAATCCCTAAGGAGCAGGGCTTCCTCTCCTTCTGGAGGGGTAACCTGGCCAACGTGATCCGT  240
ANT2m  TTATAGACTGCGTGGTCCGTATTCCCAAGGAGCAGGGAGTTTCTGTCCTTCTGGCGCGGTAACCTGGCCAATGTCATCAGA  240
ANT3m  TCGTGGACTGCATTGTCCGCATCCCCAAGGAGCAGGGCGTGCTGTCCTTCTGGAGGGGCAACCTTGCCAACGTCATTCGC  240

ANT1m  TACTTCCCCACCCAAGCTCTCAACTTCGCCTTCAAGGACAAGTACAAGCAGCTCTTCTTAGGGGGTGTGGATCGGCATAA  320
ANT2m  TACTTCCCCACCCAGGCTCTTAACTTCGCCTTCAAAGATAAAATACAAGCAGATCTTCCTGGGTGGTGTGGACAAGAGAAC  320
ANT3m  TACTTCCCCACTCAAGCCCTCAACTTCGCCTTCAAGGATAAGTACAAGCAGATCTTCCTGGGGGGCGTGGACAAGCACAC  320

ANT1m  GCAGTTCTGGCGCTACTTTGCTGGTAACCTGGCGTCCGGTGGGGCCGCTGGGGCCACCTCCCTTTGCTTTGTCTACCCGC  400
ANT2m  CCAGTTTTTGGCTCTACTTTGCAGGGAATCTGGCATCGGGTGGTGCCGCAGGGGCCACATCCCTGTGTTTGTGTACCCTC  400
ANT3m  GCAGTTCTGGAGGTACTTTGCGGGGCAACCTGGCCTCCGGCGGTGCGGCCGGCGCGACCTCCCTCTGCTTCGTGTACCCGC  400

ANT1m  TGGACTTTGCTAGGACCAGGTTGGCTGCTGATGTGGGCAGGC---GCGCCCAGCGTGAGTTCCATGGTCTGGGCGACTGT  477
ANT2m  TTGATTTTGCCCGTACCCGTCTAGCAGCTGATGTGGGTAAAGCTGGAGCTGAAAGGGAATTCCGAGGCCTCGGTGACTGC  480
ANT3m  TGGATTTTGCCAGAACCCGCCTGGCAGCGGACGTGGGAAAGTCAGGCACAGAGCGCGAGTTCCGAGGCCTGGGAGACTGC  480

ANT1m  ATCATCAAGATCTTCAAGTCTGATGGCCTGAGGGGGCTCTACCAGGGTTTCAACGTCTCTGTGCCAAGGCATCATTATCTA  557
ANT2m  CTGGGTAAGATCTACAAAATCTGATGGGATTAAGGGCCTGTACCAAGGCTTTAACGTGTCTGTGCAGGGTATTATCATCTA  560
ANT3m  CTGGTGAAGATCACCAAGTCCGACGGCATCCGGGGGCCTGTACCAGGGCTTCAGTGTCTCCGTGCAGGGCATCATCATCTA  560

ANT1m  TAGAGCTGCCTACTTCGGAGTCTATGATACTGCCAAGGGGATGCTGCCTGACCCCAAGAACGTGCACATTTTTGTGAGCT  637
ANT2m  CCGAGCCGCCTACTTCGGTATCTATGACACTGCAAAGGGAATGCTTCCGGATCCCAAGAACACTCACATCGTCATCAGCT  660
ANT3m  CCGGGCGGCCTACTTCGGCGTGTACGATACGGCCAAGGGCATGCTCCCCGACCCCAAGAACACGCACATCGTGGTGAGCT  640

ANT1m  GGATGATTGCCCAGAGTGTGACGGCAGTCGCAGGGCTGCTGTCCTACCCCTTTGACACTGTTCGTCGTAGAATGATGATG  717
ANT2m  GGATGATCGCACAGACTGTCACTGCTGTTGCCGGGTTTGACTTCCTATCCATTTGACACTGTTCGCCGCCGCATGATGATG  720
ANT3m  GGATGATCGCGCAGACCGTGACGGCCGTGGCCGGCGTGGTGTCCTACCCCTTCGACACGGTGCGGCGGCGCATGATGATG  720

ANT1m  CAGTCCGGCCGGAAAGGGGCCGGATATTATGTACACGGGGACAGTTGACTGCTGGAGGAAGATTGCAAAAGACGAAGGAGC  797
ANT2m  CAGTCAGGGCGCAAAGGAACTGACATCATGTACACAGGCACGGTTGACTGCTGGCGGAAGATTGCTCGTGATGAAGGAGG  800
ANT3m  CAGTCCGGGCGCAAAGGAGCTGACATCATGTACACGGGCACCGTCGACTGTTGGAGGAAGATCTTCAGAGATGAGGGGGG  800
```

Fig. 1A

```
ANT1m  CAAGGCCTTCTTCAAAGGTGCCTGGTCCAATGTGCTGAGAGGCATGGGCGGTGCTTTTGTATTGGTGTTGTATGATGAGA  877
ANT2m  CAAAGCTTTTTTCAAGGGTGCATGGTCCAATGTTCTCAGAGGCATGGGTGGTGCTTTTGTGCTTGTCTTGTATGATGAAA  880
ANT3m  CAAGGCCTTCTTCAAGGGTGCGTGGTCCAAGGTCCTGCGGGGCATGGGGGGCGCCTTCGTGCTGGTCCTGTACGACGAGC  880

ANT1m  TCAAAAAATATGTCTAA                                                                 894
ANT2m  TCAAGAAGTACACATAA                                                                 897
ANT3m  TCAAGAAGGTGATCTAA                                                                 897
```

*Fig. 1B*

```
hANT1p  MGDHAWSFLKDFLAGAVAAAVSKTAVAPIERVKLLLQVQHASKQISAEKQ   50
hANT2p  MTDAAVSFAKDFLAGGVAAAISKTAVAPIERVKLLLQVQHASKQITADKQ   50
hANT3p  MTEQAISFAKDFLAGGIAAAISKTAVAPIERVKLLLQVQHASKQIAADKQ   50 hANT1p  YKGIIDCVVRIPKEQGFLSFWRGNLANVIRYFPTQALNFAFKDKYKQLFL  100
hANT2p  YKGIIDCVVRIPKEQGVLSFWRGNLANVIRYFPTQALNFAFKDKYKQIFL  100
hANT3p  YKGIVDCIVRIPKEQGVLSFWRGNLANVIRYFPTQALNFAFKDKYKQIFL  100 hANT1p  GGVDRHKQFWRYFAGNLASGGAAGATSLCFVYPLDFARTRLAADVGRR-A  149
hANT2p  GGVDKRTQFWRYFAGNLASGGAAGATSLCFVYPLDFARTRLAADVGKAGA  150
hANT3p  GGVDKHTQFWRYFAGNLASGGAAGATSLCFVYPLDFARTRLAADVGKSGT  150 hANT1p  QREFHGLGDCIIKIFKSDGLRGLYQGFNVSVQGIIIYRAAYFGVYDTAKG  199
hANT2p  EREFRGLGDCLGKIYKSDGIKGLYQGFNVSVQGIIIYRAAYFGIYDTAKG  200
hANT3p  EREFRGLGDCLVKITKSDGIRGLYQGFSVSVQGIIIYRAAYFGVYDTAKG  200 hANT1p  MLPDPKNVHIFVSWMIAQSVTAVAGLLSYPFDTVRRRMMMQSGRKGADIM  249
hANT2p  MLPDPKNTHIVISWMIAQTVTAVAGLTSYPFDTVRRRMMMQSGRKGTDIM  250
hANT3p  MLPDPKNTHIVVSWMIAQTVTAVAGVVSYPFDTVRRRMMMQSGRKGADIM  250 hANT1p  YTGTVDCWRKIAKDEGAKAFFKGAWSNVLRGMGGAFVLVLYDEIKKYV.  298
hANT2p  YTGTLDCWRKIARDEGGKAFFKGAWSNVLRGMGGAFVLVLYDEIKKYT.  299
hANT3p  YTGTVDCWRKIFRDEGGKAFFKGAWSNVLRGMGGAFVLVLYDELKKVI.  299
```

*Fig. 2*

```
ATGGTCAACCCCACCGTGTTCTTCGACATTGCCGTCGACGGCGAGCCCTTGGGCCGCGTCTCCTTTGAGC  70
TACCAGTTGGGGTGGCACAAGAAGCTGTAACGGCAGCTGCCGCTCGGGAACCCGGCGCAGAGGAAACTCG
  M  V  N  P  T  V  F  F  D  I  A  V  D  G  E  P  L  G  R  V  S  F  E

TGTTTGCAGACAAGGTCCCAAAGACAGCAGAAAATTTTCGTGCTCTGAGCACTGGAGAGAAAGGATTTGG  140
ACAAACGTCTGTTCCAGGGTTTCTGTCGTCTTTTAAAAGCACGAGACTCGTGACCTCTCTTTCCTAAACC
 L  F  A  D  K  V  P  K  T  A  E  N  F  R  A  L  S  T  G  E  K  G  F  G

TTATAAGGGTTCCTGCTTTCACAGAATTATTCCAGGGTTTATGTGTCAGGGTGGTGACTTCACACGCCAT  210
AATATTCCCAAGGACGAAAGTGTCTTAATAAGGTCCCAAATACACAGTCCCACCACTGAAGTGTGCGGTA
   Y  K  G  S  C  F  H  R  I  I  P  G  F  M  C  Q  G  G  D  F  T  R  H

AATGGCACTGGTGGCAAGTCCATCTATGGGGAGAAATTTGAAGATGAGAACTTCATCCTAAAGCATACGG  280
TTACCGTGACCACCGTTCAGGTAGATACCCCTCTTTAAACTTCTACTCTTGAAGTAGGATTTCGTATGCC
   N  G  T  G  G  K  S  I  Y  G  E  K  F  E  D  E  N  F  I  L  K  H  T

GTCCTGGCATCTTGTCCATGGCAAATGCTGGACCCAACACAAATGGTTCCCAGTTTTTCATCTGCACTGC  350
CAGGACCGTAGAACAGGTACCGTTTACGACCTGGGTTGTGTTTACCAAGGGTCAAAAAGTAGACGTGACG
  G  P  G  I  L  S  M  A  N  A  G  P  N  T  N  G  S  Q  F  F  I  C  T  A

CAAGACTGAGTGGTTGGATGGCAAGCATGTGGTGTTTGGCAAAGTGAAAGAAGGCATGAATATTGTGGAG  420
GTTCTGACTCACCAACCTACCGTTCGTACACCACAAACCGTTTCACTTTCTTCCGTACTTATAACACCTC
   K  T  E  W  L  D  G  K  H  V  V  F  G  K  V  K  E  G  M  N  I  V  E

GCCATGGAGCGCTTTGGGTCCAGGAATGGCAAGACCAGCAAGAAGATCACCATTGCTGACTGTGGACAAC  490
CGGTACCTCGCGAAACCCAGGTCCTTACCGTTCTGGTCGTTCTTCTAGTGGTAACGACTGACACCTGTTG
   A  M  E  R  F  G  S  R  N  G  K  T  S  K  K  I  T  I  A  D  C  G  Q
TCGAATAA  498
AGCTTATT
 L  E
```

*Fig. 7*

```
ATGGTCAACCCCACCGTGTTCTTCGACATTGCCGTCGACGGCGAGCCCTTGGGCCGCGTCTCCTTTGAGC  70
TACCAGTTGGGGTGGCACAAGAAGCTGTAACGGCAGCTGCCGCTCGGGAACCCGGCGCAGAGGAAACTCG
  M  V  N  P  T  V  F  F  D  I  A  V  D  G  E  P  L  G  R  V  S  F  E

TGTTTGCAGACAAGGTCCCAAAGACAGCAGAAAATTTTCGTGCTCTGAGCACTGGAGAGAAAGGATTTGG  140
ACAAACGTCTGTTCCAGGGTTTCTGTCGTCTTTTAAAAGCACGAGACTCGTGACCTCTCTTTCCTAAACC
  L  F  A  D  K  V  P  K  T  A  E  N  F  R  A  L  S  T  G  E  K  G  F  G

TTATAAGGGTTCCTGCTTTCACAGAATTATTCCAGGGTTTATGTGTCAGGGTGGTGACTTCACACGCCAT  210
AATATTCCCAAGGACGAAAGTGTCTTAATAAGGTCCCAAATACACAGTCCCACCACTGAAGTGTGCGGTA
   Y  K  G  S  C  F  H  R  I  I  P  G  F  M  C  Q  G  G  D  F  T  R  H

AATGGCACTGGTGGCAAGTCCATCTATGGGGAGAAATTTGAAGATGAGAACTTCATCCTAAAGCATACGG  280
TTACCGTGACCACCGTTCAGGTAGATACCCCTCTTTAAACTTCTACTCTTGAAGTAGGATTTCGTATGCC
    N  G  T  G  G  K  S  I  Y  G  E  K  F  E  D  E  N  F  I  L  K  H  T

GTCCTGGCATCTTGTCCATGGCAAATGCTGGACCCAACACAAATGGTTCCCAGTTTTTCATCTGCACTGC  350
CAGGACCGTAGAACAGGTACCGTTTACGACCTGGGTTGTGTTTACCAAGGGTCAAAAAGTAGACGTGACG
  G  P  G  I  L  S  M  A  N  A  G  P  N  T  N  G  S  Q  F  F  I  C  T  A

CAAGACTGAGTGGTTGGATGGCAAGCATGTGGTGTTTGGCAAAGTGAAAGAAGGCATGAATATTGTGGAG  420
GTTCTGACTCACCAACCTACCGTTCGTACACCACAAACCGTTTCACTTTCTTCCGTACTTATAACACCTC
   K  T  E  W  L  D  G  K  H  V  V  F  G  K  V  K  E  G  M  N  I  V  E

GCCATGGAGCGCTTTGGGTCCAGGAATGGCAAGACCAGCAAGAAGATCACCATTGCTGACTGTGGACAAC  490
CGGTACCTCGCGAAACCCAGGTCCTTACCGTTCTGGTCGTTCTTCTAGTGGTAACGACTGACACCTGTTG
   A  M  E  R  F  G  S  R  N  G  K  T  S  K  K  I  T  I  A  D  C  G  Q
TCGAATAA  498
AGCTTATT
 L  E
```

*Fig. 8*

COMPOSITIONS AND METHODS FOR DETERMINING INTERACTIONS OF MITOCHONDRIAL COMPONENTS, AND FOR IDENTIFYING AGENTS THAT ALTER SUCH INTERACTIONS

CROSS-REFERENCES TO RELATED APPLICATIONS

This application is a continuation-in-part of U.S. Ser. No. 09/434,354 filed Nov. 3, 1999, which is incorporated herein by reference in its entirety.

TECHNICAL FIELD

The invention relates generally to methods for identifying agents that affect mitochondrial membrane permeability transition. More specifically, the invention relates to compositions and screening methods for use in identifying agents that alter the interaction between the mitochondrial adenine nucleotide translocator and cyclophilin D.

BACKGROUND OF THE INVENTION

Mitochondria are the main energy source in cells of higher organisms, and provide direct and indirect biochemical regulation of a wide array of cellular respiratory, oxidative and metabolic processes. Such processes include electron transport chain (ETC) activity, which drives oxidative phosphorylation to produce metabolic energy in the form of adenosine triphosphate (ATP), and which also underlies a central mitochondrial role in intracellular calcium homeostasis.

Mitochondrial ultrastructural characterization reveals the presence of an outer mitochondrial membrane that serves as an interface between the organelle and the cytosol, a highly folded inner miitochondrial membrane that appears to form attachments to the outer membrane at multiple sites, and an intermembrane space between the two mitochondrial membranes. The subcompartment within the inner mitochondrial membrane is commonly referred to as the mitochondrial matrix. (For a review, see, e.g., Ernster et al., 1981, *J. Cell Biol.* 91:227s.) The cristae, originally postulated to occur as infoldings of the inner mitochondrial membrane, have recently been characterized using three-dimensional electron tomography as also including tube-like conduits that may form networks, and that can be connected to the inner membrane by open, circular (30 nm diameter) junctions (Perkins et al., 1997, *Journal of Structural Biology* 119:260). While the outer membrane is freely permeable to ionic and non-ionic solutes having molecular weights less than about ten kilodaltons, the inner mitochondrial membrane exhibits selective and regulated permeability for many small molecules, including certain cations, and is impermeable to large (>~10 kDa) molecules.

Altered or defective mitochondrial activity, including but not limited to failure at any step of the ETC, may result in catastrophic mitochondrial collapse that has been termed "permeability transition" (PT) or "mitochondrial permeability transition" (MPT). According to generally accepted theories of mitochondrial function, proper ETC respiratory activity requires maintenance of an electrochemical potential ($\Delta\Psi m$) in the inner mitochondrial membrane by a coupled chemiosmotic mechanism. Altered or defective mitochondrial activity may dissipate this membrane potential, thereby preventing ATP biosynthesis and halting the production of a vital biochemical energy source. In addition, mitochondrial proteins such as cytochrome c may leak out of the mitochondria after permeability transition and may induce the genetically programmed cell suicide sequence known as apoptosis or programmed cell death (PCD).

Four of the five multi-subunit protein complexes (Complexes I, III, IV and V) that mediate ETC activity are localized to the inner mitochondrial membrane, which is the most protein rich of biological membranes in cells (75% by weight); the remaining ETC complex (Complex II) is situated in the matrix. In at least three distinct chemical reactions known to take place within the ETC, positively-charged protons are moved from the mitochondrial matrix, across the inner membrane, to the intermembrane space. This disequilibrium of charged species creates an electrochemical potential of approximately 220 mV referred to as the "proton motive force" (PMF), which is often represented by the notation $\Delta\psi$ or $\Delta\psi m$ and represents the sum of the electric potential and the pH differential across the inner mitochondrial membrane (see, e.g, Ernster et al., 1981 *J. Cell Biol.* 91:227s and references cited therein).

This membrane potential provides the energy contributed to the phosphate bond created when adenosine diphosphate (ADP) is phosphorylated to yield ATP by ETC Complex V, a process that is "coupled" stoichiometrically with transport of a proton into the matrix; $\Delta\psi m$ is also the driving force for the influx of cytosolic $Ca^{2+}$ into the mitochondrion. Under normal metabolic conditions, the inner membrane is largely impermeable to proton movement from the intermembrane space into the matrix, leaving ETC Complex V as the primary means whereby protons can return to the matrix. When, however, the integrity of the inner mitochondrial membrane is compromised, as occurs during MPT that may accompany a disease associated with altered mitochondrial function, protons are able to bypass the conduit of Complex V without generating ATP, thereby "uncoupling" respiration because electron transfer and associated proton pumping yields no ATP. Thus, mitochondrial permeability transition involves the opening of a mitochondrial membrane "pore", a process by which, inter alia, the ETC and $\Delta\psi m$ are uncoupled, $\Delta\psi m$ collapses and mitochondrial membranes lose the ability to selectively regulate permeability to solutes both small (e.g., ionic $Ca^{2+}$, $Na^+$, $K^+$, $H^+$) and large (e.g., proteins).

The mitochondrial permeability transition "pore" may not be a discrete assembly or multi-subunit complex, and the term thus refers instead to any mitochondrial molecular component (including, e.g., a mitochondrial membrane per se) that regulates the inner membrane selective permeability where such regulated function is impaired during MPT. A mitochondrial molecular component may be a protein, polypeptide, peptide, amino acid or derivative thereof; a lipid, fatty acid or the like, or derivative thereof; a carbohydrate, saccharide or the like or derivative thereof; a nucleic acid, nucleotide, nucleoside, purine, pyrimidine or related molecule, or derivative thereof, or the like; or any other biological molecule that is a constituent of a mitochondrion. A mitochondrial permeability transition pore component, also referred to as a mitochondrial pore component, may be any mitochondrial molecular component that regulates the selective permeability characteristic of mitochondrial membranes as described above, including those responsible for establishing $\Delta\Psi m$ and those that are functionally modified during MPT. Mitochondrial pore components may also include factors that interact with mitocbondria, for example through transient or stable association with other mitochondrial pore components, in a manner that regulates MPT. Examples of such factors include cyclophilins (described in greater detail below), calcium modulating cyclophilin ligand (CAML, see, e.g., Table 1, infra, and references cited therein) and members of the Bcl-2 family including Bcl-2 (e.g., Green et al., 1998 *Science* 281:1309), Bax (Marzo et al., 1998 *Science* 281:2027) and Bak (Narita et al., 1998 *Proc. Nat. Acad. Sci. USA* 95:14681).

Without wishing to be bound by theory, it is unresolved whether this pore is a physically discrete conduit that is formed in mitochondrial membranes, for example by assembly or aggregation of particular mitochondrial and/or cytosolic proteins and possibly other molecular species, or whether the opening of the "pore" may simply represent a general increase in the porosity of the mitochondrial membrane. In any event, certain mitochondrial molecular components may contribute to the MPT mechanism, including ETC components or other mitochondrial components described herein. For example, some non-limiting examples of mitochondrial permeability transition pore components that appear to contribute to the MPT mechanism include members of the following families of gene products (see, e.g., Table 1, infra, and references cited therein): adenine nucleotide translocator (ANT); peripheral benzodiazepine receptor (PBzR; McEnery et al., 1992 *Proc. Nat. Acad. USA* 89:3170); PBzR-associated protein (PRAX); voltage dependent anion channel (VDAC, also known as porin); cyclophilin (Cyp); calcium modulating cyclophilin ligand (CAML); the mitochondrial calcium uniporter, mitochondria associated hexokinase(s) and mitochondrial intermembrane creatine kinases.

MPT may result from direct or indirect effects of mitochondrial genes, gene products or downstream mediator molecules and/or extramitochondrial genes, gene products or downstream mediators. MPT may also result from other known or unknown causes. Loss of mitochondrial potential may be a critical event in the progression of diseases associated with altered mitochondrial function, including degenerative diseases.

Mitochondrial defects may contribute significantly to the pathogenesis of diseases associated with altered mitochondrial function. Such defects may be related to the discrete mitochondrial genome that resides in mitochondrial DNA (i.e., the mitochondrial chromosome) and/or to the extramitochondrial genome, which includes nuclear chromosomal DNA and other extramitochondrial DNA. For example, alterations in the structural and/or functional properties of mitochondrial components, including alterations deriving from genetic and/or environmental factors or alterations derived from cellular compensatory mechanisms, may play a role in the pathogenesis of any disease associated with altered mitochondrial function. A number of degenerative diseases are thought to be caused by, or to be associated with, alterations in mitochondrial function. These include Alzheimer's Disease (AD); diabetes mellitus; Parkinson's Disease; Huntington's disease; dystonia; Leber's hereditary optic neuropathy; schizophrenia; mitochondrial encephalopathy, lactic acidosis, and stroke (MELAS); cancer; psoriasis; hyperproliferative disorders; raitochondrial diabetes and deafness (MIDD) and myoclonic epilepsy ragged red fiber syndrome. The extensive list of additional diseases associated with altered mitochondrial function continues to expand as aberrant mitochondrial or mitonuclear activities are implicated in particular disease processes.

A hallmark pathology of AD and potentially other diseases associated with altered mitochondrial function is the death of selected cellular populations in particular affected tissues, which results from apoptosis (also referred to as "programmed cell death" or PCD). Mitochondrial dysfunction is thought to be critical in the cascade of events leading to apoptosis in various cell types (Kroemer et al., *FASEB J.* 9:1277–87, 1995), and may be a cause of apoptotic cell death in neurons of the AD brain. Altered mitochondrial physiology may be among the earliest events in PCD (Zamzami et al., *J. Exp. Med.* 182:367–77, 1995; Zamzami et al., *J. Exp. Med* 181;1661–72, 1995) and elevated reactive oxygen species (ROS) levels that result from such altered mitochondrial function may initiate the apoptotic cascade (Ausserer et al., *Mol. Cell. Biol.* 14:5032–42, 1994).

Thus, in addition to their role in energy production in growing cells, mitochondria (or, at least, mitochondrial components) participate in apoptosis (Newmeyer et al., 1994, *Cell* 79:353–364; Liu et al., 1996, *Cell* 86:147–157). Apoptosis is apparently also required for, inter alia, normal development of the nervous system and proper functioning of the immune system. Moreover, some disease states are thought to be associated with either insufficient (e.g., cancer, autoimmune diseases) or excessive (e.g., stroke damage, AD-associated neurodegeneration) levels of apoptosis. For general reviews of apoptosis, and the role of mitochondria therein, see Green and Reed (1998, *Science* 281:1309–1312), Green (1998, *Cell* 94:695–698) and Kromer (1997, *Nature Medicine* 3:614–620). Hence, agents that affect apoptotic events, including those associated with mitochondrial components, might have a variety of palliative, prophylactic and therapeutic uses.

The adenine nucleotide translocator (ANT) is an example of one particular mitochondrial pore component as provided herein. ANT, nuclear encoded polypeptide that is a major component of the inner mitochondrial membrane, is responsible for mediating transport of ADP and ATP across the mitochondrial inner membrane. For example, ANT is believed to mediate stoichiometric ATP/proton exchange or cotransport across the inner mitochondrial membrane, and ANT inhibitors (such as atractyloside or bongkrekic acid) induce MPT under certain conditions. Three human ANT isoforms have been described that differ in their tissue expression patterns and other mammalian ANT homologues have been described (see, e.g., Wallace et al., 1998 in *Milochondria & Free Radicals in Neurodegenerative Diseases,* Beal, Howell and Bodis-Wollner, Eds., Wiley-Liss, New York, pp. 283–307, and references cited therein). ANT has also been implicated as an important molecular component of the mitochondrial permeability transition pore, a $Ca^{2+}$-regulated inner membrane channel that, as described above, plays an important modulating role in apoptotic processes.

Members of the cyclophilin family of highly conserved proteins provide an example of mitochondrial pore components as provided herein that are factors which, as described above, may stably or transiently interact with other mitochondrial pore components in a manner that regulates MPT. The cyclophilins (Cyps) are a family of ubiquitous proteins expressed in all organisms. All Cyp family members share a conserved core of about 109 amino acids, but differ from one another by unique extensions that function in organelle and membrane transport (e.g., Walsh et al., 1992 *J. Biol. Chem.* 267:13115–18). At least eight human Cyp isoforms are known, including single domain and two-domain cyclophilins (e.g., Taylor et al., 1997 *Prog. Biophys. Mol. Biol.* 67:155–81). Distinct isoforms localize to different cell compartments, including cytoplasmic, endoplasmic reticulum (ER), mitochondrial, and cell surface isoforms (Handler et al. *EMBO J.* 6:947–50, 1987; Price et al. *Proc. Natl. Acad. Sci. USA* 88:1903–07, 1991, Bergsma et al. *J. Biol. Chem* 266: 23204–14; Cacalano et al. *Proc Natl Acad Sci USA* 89:

4353–57, 1992). For example, and as described in greater detail below, Cyclophilin D (CypD) is another molecule that may regulate mitochondrial permeability.

Cyclophilins are believed to perform multiple functions within cells. For example, Cyps catalyze the interconversion of cis and trans isomers of peptidylprolyl bonds in peptides and proteins, thereby facilitating the folding of proteins for which isomerization of peptidylprolyl bonds is rate limiting (see, e.g., Galat, *Eur. J. Biochem.* 216:689–707, 1993; Fischer et al., *Biochem.* 29:2205–2212, 1990; Stamnes et al., *Cell* 65:219–27, 1991). This peptidylproyl cis-trans-isomerase activity can be blocked by the immunosuppressant cyclosporin A (e.g., Fruman et al., *Proc. Natl. Acad. Sci. USA* 89:3741 45, 1992). Cyp family members also appear to mediate other activities by forming complexes with fully folded, functional proteins (see, e.g., Jaschke et al., *J. Mol. Biol.* 277:763–69, 1998; Ratajczk et al., *J. Biol. Chem.* 268:13187–92, 1993; Wu et al., *J. Biol. Chem.* 270:14209–19, 1995; Holloway et al., *J. Biol. Chem.* 273:16346–50, 1998; Franke et al., *Adv. Exp. Med. Biol.* 374: 217–28, 1995).

CypD is the only mitochondrial isoform of the Cyp family identified to date. The human CypD polypeptide is 207 amino acids long and has an $NH_2$-terminal hydrophobic extension, which may serve to transport the polypeptide across mitochondrial membranes to the matrix (Bergsma et al., *J. Biol. Chem.* 266:23204–14, 1991). Cyp D is believed to participate in the formation of the mitochondrial permeability transition pore by interacting with the voltage-dependent anion channel (VDAC) and with ANT, at contact sites between the mitochondrial outer and inner membranes (Crompton et al., *Eur. J. Biochem.* 258 729–35, 1998; Woodfield et al., 1998, *Biochem. J.* 336:287–90). CypD binding to ANT may also sensitize the pore complex to $Ca^{2+}$ concentration (Halestrap et al., *Biochim. Biophys. Acta.* 1366:79–94, 1998). In vitro, relatively high $Ca^{2+}$ concentrations increase mitochondrial membrane permeability, resulting in free diffusion of low molecular weight solutes across the inner membrane (e.g., Halestrap et al., *Mol. Cell. Biochem.* 174:167–172, 1997; Hunter et al., *Arch. Biochem. Biophys.* 195:453–59, 1979). Oxidative stress, adenine nucleotide depletion and decreased membrane potential may also increase mitochondrial permeability (e.g., Bernardi et al., *J. Bioenerg. Biomembr.* 26:509–17, 1994; Zoratti et al., *Biochim. Biophys. Acta* 1241:139–76, 1995). This opening of the mitochondrial permeability transition pore may be an event in the pathogenesis of diseases associated with altered mitochondrial function, such as those described above. For example, MPT may contribute to necrotic cell death following vascular ischemia/reperfusion injury as may occur following cardiac bypass surgery, thrombolysis and organ transplantation (e.g., Halestrap et al., *Biochem. Soc. Trans.* 21:353–58, 1993; Halestrap et al., *Mol. Cell. Biochem.* 174:167–172, 1997). As another example, a VDAC-ANT-CypD complex may also participate in mitochondrial outer membrane rupture resulting in the release of apoptogenic proteins from the intermembrane space (e.g., Petit et al., *FEBS Lett.* 426:111–16, 1998; Marzo et al. *J. Exp. Med.* 187:1261–71, 1998).

To provide improved therapies for diseases associated with altered mitochondrial function such as those discussed above, agents that alter mitochondrial permeability transition may be beneficial, and assays to specifically detect such agents are needed. The present invention fulfills these needs and further provides other related advantages.

SUMMARY OF THE INVENTION

The present invention is directed to assays for identifying and using agents that alter mitochondrial membrane permeability transition, and to related compositions and methods. In one aspect, the invention provides a nucleic acid expression construct comprising a promoter operably linked to a polynucleotide encoding a mitochondrial permeability transition pore component polypeptide fused to an energy transfer molecule polypeptide, or a variant thereof. In one embodiment the mitochondrial permeability transition pore component is an adenine nucleotide translocator, which in certain further embodiments is human ANT1, human ANT2 or human ANT3. In one embodiment the mitochondrial permeability transition pore component is porin, hexokinase, creatine kinase, PRAX, CAML or the peripheral benzodiazepine receptor. The invention also provides, in certain embodiments, a nucleic acid expression construct comprising a promoter operably linked to a polynucleotide encoding a cyclophilin polypeptide fused to an energy transfer molecule polypeptide, or a variant thereof. In one embodiment the cyclophilin is cyclophilin D, and in other embodiments the cyclophilin is human cyclophilin A, cyclophilin B, human cyclophilin C or human Cyp-60. In certain embodiments the expression construct comprises a vector that is a plasmid, a cosmid, a shuttle vector, a viral vector or a vector comprising a chromosomal origin of replication. In certain embodiments the vector comprises a plasmid that is pBAD-His, pEYFP-C1 or pECFP-N1.

According to certain embodiments of the invention, the promoter is externally regulated. In some embodiments the energy transfer molecule is a green fluorescent protein (GFP), a FLASH sequence or an aequorin protein. In certain further embodiments the green fluorescent protein is blue-shifted GFP, cyan-shifted GFP, red-shifted GFP or yellow-shifted GFP. In certain other embodiments the energy transfer molecule is a derivative of an energy transfer molecule selected that is a green fluorescent protein (GFP), a FLASH sequence or an aequorin protein.

In another aspect, the invention provides a polypeptide comprising a mitochondrial permeability transition pore component polypeptide fused to an energy transfer molecule polypeptide, or a derivative thereof. In certain embodiments the mitochondrial permeability transition pore component is an adenine nucleotide translocator, which in certain further embodiments is human ANT1, human ANT2 or human ANT3. In certain other embodiments the mitochondrial permeability transition pore component is porin, hexokinase, creatine kinase, PRAX, CAML or the peripheral benzodiazepine receptor. In another embodiment the invention provides a polypeptide comprising a cyclophilin polypeptide fused to an energy transfer molecule polypeptide, or a derivative thereof. In certain embodiments the cyclophilin is cyclophilin D, and in certain other embodiments the cyclophilin is human cyclophilin A, cyclophilin B, human cyclophilin C or human Cyp-60. In certain embodiments the energy transfer molecule is a green fluorescent protein (GFP), a FLASH sequence or an aequorin protein. In certain further embodiments, the green fluorescent protein is blue-shifted GFP, cyan-shifted GFP, red-shifted GFP or yellow-shifted GFP.

Turning to another aspect, the invention provides a host cell for identifying agents that alter mitochondrial permeability transition, comprising (a) a first nucleic acid expression construct, comprising a promoter operably linked to a polynucleotide encoding a mitochondrial permeability transition pore component polypeptide fused to a polynucleotide encoding a first energy transfer molecule or a variant thereof; and (b) a second nucleic acid expression construct, comprising a promoter operably linked to a polynucleotide encoding a cyclophilin polypeptide fused to a polynucleotide encoding a second energy transfer molecule or a variant thereof, wherein binding of the mitochondrial permeability transition pore component polypeptide to the cyclophilin polypeptide results in detectable energy transfer between the first and second energy transfer molecules. In certain embodiments the mitochondrial permeability transition pore component is an adenine nucleotide translocator, which in certain further embodiments is human ANT1, human ANT2 or human ANT3. In certain other embodiments the mitochondrial permeability transition pore component is porin, hexokinase, creatine kinase, PRAX, CAML or the peripheral benzodiazepine receptor. In certain embodiments the cyclophilin is human cyclophilin A, cyclophilin B, human cyclophilin C or human Cyp-60. In certain other embodiments the host cell is a prokaryotic cell, and in certain other embodiments the host cell is a eukaryotic cell. In certain further embodiments the eukaryotic cell is a 293, COS-7, Sf9, CHO, Hep-2, MDCK or Jurkat cell. In certain other embodiments the first and second energy transfer molecules are green fluorescent protein (GFP), blue-shifted GFP, cyan-shifted GFP, red-shifted GFP or yellow-shifted GFP. In certain other embodiments the first and second energy transfer molecules have an excitation maximum at a wavelength ranging from 300 nm to 650 nm, and an emission maximum at a wavelength ranging from 350 nm to 675 nm. In certain other embodiments the first energy transfer molecule and the second energy transfer molecule have excitation and emission maxima at different wavelengths. In still other certain embodiments at least one nucleic acid expression construct is extrachromosomal, while in other embodiments at least one nucleic acid expression construct is integrated into a host cell chromosome. In certain further embodiments the host cell chromosome is a mitochondrial chromosome.

It is yet another aspect of the invention to provide a method for screening for an agent that alters mitochondrial permeability transition (MPT), comprising the steps of (a) contacting a host cell, according to the invention as described above, comprising a mitochondrion with a candidate agent and an inducer of MPT; (b) exposing the cell to an excitation energy; (c) detecting a level of energy transfer between the first and second energy transfer molecules; and (d) comparing the level of energy transfer to a first reference level generated in the absence of candidate agent, and therefrom identifying an agent that alters MPT. In one embodiment the host cell is further contacted with an inhibitor of MPT to generate a second reference level, and in a further embodiment the inhibitor of MPT is low pH, inducers of high mitochondrial membrane potential or cyclosporin A. In another embodiment the inducer of MPT is atractyloside or bonkrekic acid. In another embodiment the inducer of MPT comprises a compound that increases $Ca^{+2}$ concentration in the mitochondria, and in certain further embodiments the compound is an ionophores, ionomycin, thapsigargin, amino acid neurotransmitters, glutamate, N-methyl-D-aspartic acid, carbachol, apoptogens, or an inducer of potassium depolarization. In another embodiment, the host cell is further contacted with an inducer of oxidative stress, and in certain further embodiments the inducer of oxidative stress is ethacrynic acid, buthionine sulfoximine, diamide, menadione, t-butyl hydroperoxide, phenyl-arsine oxide or nitric oxide. In certain other embodiments the candidate agent increases energy transfer between the first and second energy transfer molecules, while in certain other embodiments the candidate agent decreases energy transfer between the first and second energy transfer molecules. In another embodiment the first and second energy transfer molecules are green fluorescent protein (GFP), blue-shifted GFP, cyan-shifted GFP, red-shifted GFP or yellow-shifted GFP. In some embodiments the excitation energy is light with a wavelength ranging from 300 nm to 650 nm. In other embodiments the first and second energy transfer molecules have an excitation maximum at a wavelength ranging from 300 nm to 650 nm, and an emission maximum at a wavelength ranging from 350 nm to 675 nm.

In certain other embodiments the first energy transfer molecule and the second energy transfer molecule have excitation and emission maxima at different wavelengths. In certain other embodiments (a) the first energy transfer molecule has an excitation maximum at a wavelength ranging from 400 nm to 500 nm and an emission maximum at a wavelength ranging from 450 nm to 525 nm, and the second energy transfer molecule has an excitation maximum at a wavelength ranging from 450 nm to 525 nm and an emission maximum at a wavelength ranging from 500 nm to 550 nm; or (b) the second energy transfer molecule has an excitation maximum at a wavelength ranging from 400 nm to 450 nm and an emission maximum at a wavelength ranging from 450 nm to 500 nm, and the first energy transfer molecule has an excitation maximum at a wavelength ranging from 500 nm to 525 nm and an emission maximum at a wavelength ranging from 525 nm to 550 nm. In certain other embodiments (a) the first energy transfer molecule has an excitation maximum at a wavelength of about 433 nm and an emission maximum at a wavelength of about 475 nm, and the second energy transfer molecule has an excitation maximum at a wavelength of about 513 nm and an emission maximum at a wavelength of about 527 nm; or (b the second energy transfer molecule has an excitation maximum at a wavelength of about 433 nm and an emission maximum at a wavelength of about 475 nm, and the first energy transfer molecule has an excitation maximum at a wavelength of about 513 nm and an emission maximum at a wavelength of about 527 nm.

The present invention provides, in another aspect, a method for detecting an agent that alters mitochondrial permeability transition (MPT), comprising the steps of (a) contacting a cyclophilin D polypeptide with an adenine nucleotide translocator polypeptide and a candidate agent, under conditions and for a time sufficient to permit the cyclophilin D, adenine nucleotide translocator, and the candidate agent to interact; and (b) detecting a level of binding of cyclophilin D polypeptide to adenine nucleotide translocator polypeptide, relative to a level of binding detected in the absence of the candidate agent, and therefrom detecting an agent that alters MPT. In certain embodiments the cyclophilin D polypeptide is immobilized on a support, and in certain embodiments the cyclophilin D polypeptide is a fusion protein. In certain other embodiments the adenine nucleotide translocator polypeptide is immobilized on a support, and in certain embodiments the adenine nucleotide translocator polypeptide is a fusion protein. In certain further embodiments the fusion protein comprises a protease recognition sequence, while in certain other further embodiments the fusion protein comprises a ligand for a receptor. In certain other embodiments the candidate agent is a peptide, a polypeptide, a protein or a small molecule. In some embodiments the candidate agent is a small molecule present within a combinatorial library. The invention thus also provides in certain embodiments an agent capable of altering mitochondrial permeability transition, wherein the agent is identified by the methods just described. In certain other embodiments the invention provides a method for altering survival of a cell, comprising contacting a cell with an agent identified according to the methods just described, under conditions and for a time sufficient to modulate cell survival. In certain other embodiments, the invention provides a method for altering mitochondrial permeability transition (MPT), comprising contacting a mitochondrion with an agent identified according to the methods just described, under conditions and for a time sufficient to alter MPT. In certain further embodiments the mitochondrion is present within a cell. In certain further embodiments the cell is present within a living organism. In other embodiments the cell is a cybrid cell.

In still another aspect the present invention provides a method for preparing a mitochondrial permeability transition pore component polypeptide fused to an energy transfer molecule, comprising the steps of (a) culturing a host cell comprising a nucleic acid expression construct that encodes a fusion protein comprising an adenine nucleotide translocator polypeptide or a derivative thereof fused to an energy transfer molecule polypeptide or a derivative thereof, under conditions that permit expression of the fusion protein; and (b) recovering the fusion protein from the culture. In certain embodiments the mitochondrial permeability transition pore component is an adenine nucleotide translocator, which in certain further embodiments is human ANT1, human ANT2 or human ANT3. In certain other embodiments the mitochondrial permeability transition pore component is porin, hexokinase, creatine kinase, PRAX, CAML or the peripheral benzodiazepine receptor. In another embodiment the invention provides a method for preparing a cyclophilin polypeptide fused to an energy transfer molecule, comprising the steps of (a) culturing a host cell comprising a nucleic acid expression construct that encodes a fusion protein comprising a cyclophilin polypeptide or a derivative thereof fused to an energy transfer molecule polypeptide or a derivative thereof, under conditions that permit expression of the fusion protein; and (b) recovering fusion protein from the culture. In certain embodiments the cyclophilin polypeptide is a cyclophilin D polypeptide, and in certain other embodiments the cyclophilin polypeptide is human cyclophilin A, cyclophilin B, human cyclophilin C or human Cyp-60. In certain embodiments the host cell is a prokaryotic cell, and in certain other embodiments the host cell is a eukaryotic cell, which in certain further embodiments is a 293, a COS-1, a COS-7, a Sf9, a CHO, a Hep-2, a MDCK or a Jurkat cell. In other embodiments, the nucleic acid expression construct is extrachromosomal. In other embodiments, the nucleic acid expression construct is integrated into a host cell chromosome, which in certain further embodiments is a mitochondrial chromosome. In certain other embodiments the fusion protein comprises a recognition sequence for a protease, and in certain other embodiments the fusion protein comprises a ligand for a receptor.

In certain other embodiments the invention provides a kit for screening for agents that alter mitochondrial permeability transition, comprising (a) an isolated cyclophilin D polypeptide or a derivative thereof; (b) an isolated adenine nucleotide translocator polypeptide or a derivative thereof; and (c) a detection reagent that specifically binds to at least one of the foregoing polypeptides. In certain embodiments the cyclophilin D polypeptide is immobilized on a support. In certain other embodiments the adenine nucleotide translocator polypeptide is immobilized on a support. In other embodiments the detection reagent is an antibody or antigen-binding fragment thereof. In another embodiment the invention provides a kit for screening for agents that alter mitochondrial permeability transition (MPT), comprising (a) a host cell; (b) a first nucleic acid expression construct, comprising a promoter operably linked to a polynucleotide encoding an adenine nucleotide translocator polypeptide fused to a first energy transfer molecule or a variant thereof; and (c) a second nucleic acid expression construct, comprising a promoter operably linked to a polynucleotide encoding a cyclophilin D polypeptide fused to a second energy transfer molecule or a variant thereof. In a further embodiment the host cell is a prokaryotic cell, and in a different further embodiment the host cell is a eukaryotic cell, which in certain further embodiments is a 293, a COS-1, a COS-7, a Sf9, a CHO, a Hep-2, a MDCK or a Jurkat cell. In certain other embodiments, the first and second energy transfer molecules are green fluorescent protein (GFP), blue-shifted GFP, cyan-shifted GFP, red-shifted GFP or yellow-shifted GFP.

These and other aspects of the present invention will become apparent upon reference to the following detailed description and attached drawings. All references disclosed herein are hereby incorporated by reference in their entireties as if each was incorporated individually.

BRIEF DESCRIPTION OF THE DRAWINGS

FIG. 1 shows the nucleotide sequences of the coding regions of human ANT1 ("ANT1m"), (SEQ ID NO: 1), human ANT2 ("ANT2m") (SEQ ID NO: 57) and human ANT3 ("ANT3m") (SEQ ID NO: 3).

FIG. 2 shows the polypeptide sequences of human ANT1 ("ANT1p") (SEQ ID NO: 47), human ANT2 ("ANT2p") (SEQ ID NO: 48) and human ANT3 ("ANT3p") (SEQ ID NO: 49).

FIG. 7 shows the nucleotide sequence (SEQ ID NO:26) and amino acid sequence (SEQ ID NO:27) of human cyclophilin A (huCypA).

FIG. 8 shows the nucleotide sequence (SEQ ID NO:39) and amino acid sequence (SEQ ID NO:40) of human cyclophilin D (huCypD).

DETAILED DESCRIPTION OF THE INVENTION

Figure 3:
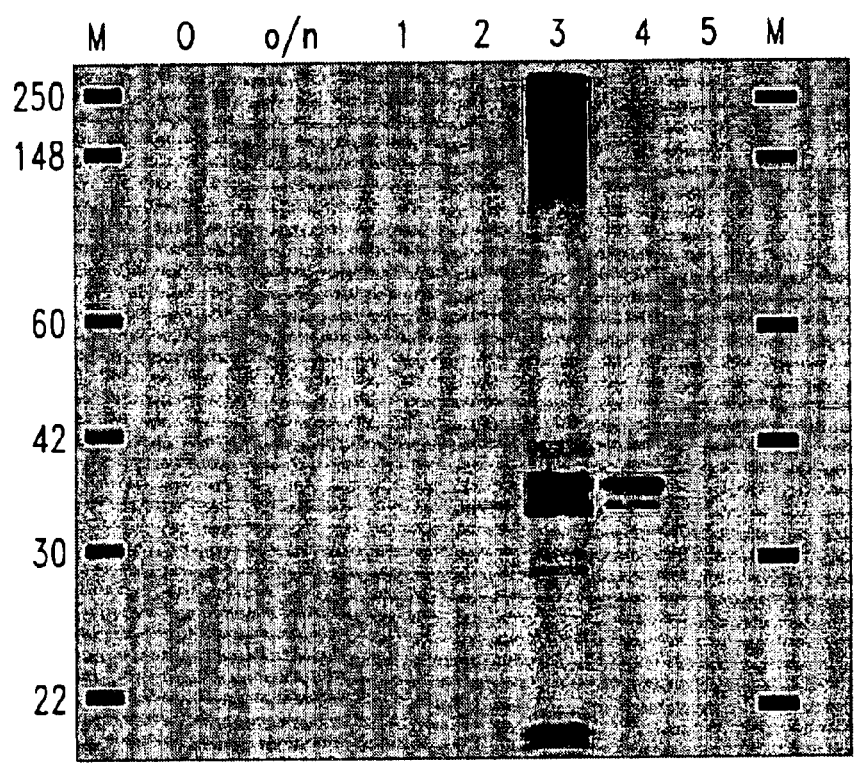
FIG. 3 shows induction of His-Tagged, XPRESS™-epitope containing huANT3 protein in *E. coli* as determined by Western analysis.

As noted above, the present invention provides compositions and assays for use in identifying agents that alter mitochondrial permeability transition (MPT). The invention thus relates generally to the surprising discovery that alteration of mitochondrial permeability transition can be predicted and/or observed by detecting interactions between selected pairs of mitochondrial permeability transition pore components that have been modified to provide energy transfer molecule fusion polypeptides, as described herein. The invention therefore contemplates exploitation of such interactions wherein any pair of mitochondrial pore component polypeptides may be fused to suitable energy transfer molecules for use in the methods provided herein, according to the instant disclosure. Although the present disclosure describes various embodiments wherein interaction is detected between a mitochondrial permeability transition pore component (which in certain embodiments is an adenine nucleotide translocator polypeptide) and a cyclophilin polypeptide, the invention is not intended to be so limited and relates generally to interactions between a first and a second mitochondrial pore component.

Thus, for example, the present invention is directed more specifically in certain embodiments to adenine nucleotide translocator (ANT) and cyclophilin D (CypD) polypeptides, such as fusion proteins; to nucleic acid expression constructs encoding such polypeptides; and to screening methods for detecting natural and synthetic agents (e.g., small molecules, ANT ligands and CypD ligands) that interact with such polypeptides and/or complexes thereof. However, the spirit and scope of the various embodiments disclosed herein are not intended to be limited to ANT-cyclophilin interactions, but instead are intended to encompass interactions between any mitochondrial pore components as provided herein, including interactions involving pore components that are factors which interact with mitochondria, for example through transient or stable association with other mitochondrial pore components, in a manner that regulates MPT.

As noted above, the selective permeability of the inner mitochondrial membrane requires proper functioning of the ETC to maintain an electrochemical potential along the membrane. Adenine nucleotide translocator (ANT) is believed to mediate ATP/proton exchange or cotransport across the inner mitochondrial membrane, and to specifically bind with cyclophilin D (CypD) to potentiate, under certain conditions, formation of the MPT "pore." The role in MPT of these and other mitochondrial molecular components, and factors influencing such components, may be investigated using the methods provided herein. In certain preferred aspects, the present invention pertains to binding and functional assays wherein an interaction between ANT and CypD is detected to screen for and identify agents that alter MPT.

Adenine Nucleotide Translocator (Ant) and Cyclophilin D (CypD) Polypeptides

The present invention is directed generally to adenine nucleotide translocator (ANT) and cyclophilin D (CypD) polypeptides, such as fusion proteins. Such polypeptides may comprise any ANT or CypD isoform. The present invention further provides methods for producing recombinant ANT and CypD polypeptides, including fusion proteins, by culturing host cells containing ANT-encoding and/or CypD-encoding nucleic acid expression constructs. The invention is also directed to methods for screening for agents that alter MPT using isolated recombinant ANT and CypD polypeptides (such as fusion proteins).

The polypeptides and nucleic acids of the present invention are preferably provided in an isolated form, and in certain preferred embodiments are purified to homogeneity. As used herein, the term "isolated" means that the material is removed from its original environment (e.g., the natural environment if it is naturally occurring). For example, a naturally occurring nucleic acid or polypeptide present in a living animal is not isolated, but the same nucleic acid or polypeptide, separated from some or all of the co-existing materials in the natural system, is isolated. Such nucleic acids could be part of a vector and/or such nucleic acids or polypeptides could be part of a composition, and still be isolated in that such vector or composition is not part of its natural environment.

ANT and CypD polypeptides as provided herein may comprise one or more deduced amino acid sequences of FIGS. 1 and 8 (SEQ ID NOS: 1, 57, 3 and 39). Alternatively, such polypeptides may comprise one or more polypeptide sequences encoded by ANT/CypD nucleic acid expression constructs as provided herein. Polypeptides comprising fragments, analogs and derivatives of such polypeptide sequences, as well as fusion proteins, are further contemplated. As used herein, the terms "fragment," "derivative" and "analog" when referring to ANT and CypD polypeptides or fusion proteins, refer to any ANT and CypD polypeptides or fusion proteins that retain essentially the same biological function or activity as such polypeptide. For example, an analog may be a proprotein that can be activated by cleavage to produce an active ANT and/or CypD polypeptide. The polypeptide of the present invention may be a recombinant polypeptide or a synthetic polypeptide, and is preferably a recombinant polypeptide.

A fragment, derivative or analog of an ANT or a CypD polypeptide, including ANT and CypD polypeptides and fusion proteins encoded by the nucleic acid expression constructs, may be (i) one in which one or more of the amino acid residues are substituted with a conserved or non-conserved amino acid residue (preferably a conserved amino acid residue) and such substituted amino acid residue may or may not be one encoded by the genetic code, (ii) one in which one or more of the amino acid residues includes a substituent group, (iii) one in which the ANT and/or CypD polypeptides are fused with another compound, such as a compound to increase the half-life of the polypeptide (e.g., polyethylene glycol), and/or (iv) one in which additional amino acids are fused to the ANT and/or CypD polypeptides, including amino acid sequences that are employed for detection of the ANT and/or CypD polypeptide as described in greater detail below, and/or for purification of the ANT/CypD polypeptide or a proprotein sequence. Such fragments, derivatives and analogs are deemed to be within the scope of those skilled in the art from the teachings herein.

Within certain methods provided herein, bacterial, insect, yeast and/or mammalian expression systems can be designed for reliable production of detectable recombinant ANT and/or CypD polypeptides in significant quantities. In certain embodiments, compositions and methods for producing recombinant ANT and CypD fusion proteins are provided, wherein the fusion proteins comprise energy transfer molecule polypeptide sequences. Within certain of these and other embodiments, compositions and methods are provided for producing detectable recombinant ANT fusion proteins and CypD fusion proteins from an externally regulated promoter. In certain preferred embodiments, the design of such expression systems includes the use of a host cell that includes at least one mitochondrion.

ANT and CypD polypeptides, such as fusion proteins, may be useful within intact host cells, or in preparations of intact organelles such as mitochondria, cell membranes or intracellular vesicles. Such polypeptides may further be useful in disrupted cell preparations including, but not limited, to cell homogenates or lysates, submitochondrial particles, uni- and multi-lamellar membrane vesicles or other preparations. Alternatively, the ANT and CypD polypeptides can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the functional protein. Finally, high performance liquid chromatography (HPLC) can be employed for final purification steps.

The polypeptides of the present invention may be a naturally purified product, a product of chemical synthetic procedures, or a product of recombinant techniques from a prokaryotic or eukaryotic host (for example, bacterial, yeast, higher plant, insect or mammalian cells in culture). Depending upon the host employed in a recombinant production procedure, the polypeptides and fusion proteins of the present invention may be glycosylated or may be non-glycosylated. Polypeptides may also include an initial methionine amino acid residue.

The compositions and methods provided herein can be adapted to any prokaryotic or eukaryotic ANT, including plant and animal ANTs, which may further include, for example, yeast, vertebrate and mammalian ANTs, including rodent, non-human primate and human ANTs, for which amino acid sequences and/or encoding nucleic acids will be known to those familiar with the art. Three human ANT (huANT) isoforms have been described that differ in their tissue expression patterns (Stepien et al., 1992 *J. Biol. Chem.* 267:14592; see also Wallace et al., 1998 in *Mitochondria & Free Radicals in Neurodegenerative Diseases,* Beal, Howell and Bodis-Wollner, Eds., Wiley-Liss, New York, pp. 283–307, and references cited therein). Nucleic acid sequences for cDNAs (see Neckelmann et al., *Proc. Nat'l. Acad. Sci. U.S.A.* 84;7580–7584 (1987) for huANT1 cDNA; Battini et al., *J. Biol. Chem.* 262:4355–4359 (1987) for huANT2 cDNA, and Cozens et al., *J. Mol. Biol.* 206:261–280 (1989) for huANT3 cDNA) and amino acid sequences for these three human ANT isoforms have been reported; and ANT gene sequences have been determined for a number of species (see, e.g., Li et al., 1989 *J. Biol. Chem.* 264:13998 for huANT1 genomic DNA; Liew et al. GenBank Acc. No. N86710 for huANT2; Shinohara et al., 1993 *Biochim. Biophys. Acta* 1152:192 for rat ANT gene; for others see also, e.g., Ku et al., 1990 *J. Biol. Chem.* 265:16060; Adams et al., 1991 *Science* 252:1651; and WO 98/19714.). ANT sequences among mammalian species are highly conserved; for example, at the amino acid level murine ANT1 and ANT2 exhibit 98% sequence identity with human ANT2. Full length amino acid sequences of at least 29 ANT proteins have been reported to date from a variety of animal and plant species, with most of these deduced from nucleic acid sequences (Fiore et al., 1998 *Biochimie* 80:137–150).

Similarly, the compositions and methods of the present invention may also be adapted to any prokaryotic or eukaryotic Cyp such as a CypD, including plant and animal CypDs, which may further include, for example, yeast, parasite, invertebrate, rodent, and human CypDs, for which amino acid sequences and/or encoding nucleic acids will be known to those familiar with the art (see, e.g., Table 1, infra). In addition to the nucleic and amino acid sequences of three human CypD (also known as Cyp3) isoforms (see, e.g., Bergsma et al., 1991, *J. Biol. Chem.* 266 23204–14, GenBank Acc. No. M80254 for cDNA and Acc. No. AAA58434 for deduced amino acid sequence of human Cyp3), CypD sequences from other species have been reported (see, e.g., GenBank Acc. No. U68544 for cDNA and No. AAB08453 for deduced amino acid sequence of rat CypD).

The polypeptides of the present invention include ANT and CypD polypeptides and fusion proteins having amino acid sequences that are identical or similar to sequences known in the art. For example, by way of illustration and not limitation, the human ANT and CypD polypeptides of FIGS. 1, 2, 7 and 8 (SEQ ID NOS: 47–49, 27 and 40) are contemplated for use according to the instant invention, as are polypeptides having at least 70% similarity (preferably a 70% identity) to the polypeptides of FIGS. 1, 2, 7 and 8 and more preferably 90% similarity (more preferably a 90% identity) to the polypeptides of FIGS. 1, 2, 7 and 8 and still more preferably a 95% similarity (still more preferably a 95% identity) to the polypeptides of FIGS. 1, 2, 7 and 8 and to portions of such polypeptides, wherein such portions of ANT and CypD polypeptides generally contain at least 8 consecutive amino acids, preferably at least 12 consecutive amino acids, more preferably at least 20 consecutive amino acids, more preferably at least 30 consecutive amino acids and more preferably at least 50 consecutive amino acids.

"Similarity" between two polypeptides is generally determined by comparing the amino acid sequence and conserved amino acid substitutes thereto of the polypeptide to the sequence of a second polypeptide. Fragments or portions of the polypeptides of the present invention may be employed for producing the corresponding full-length polypeptide by peptide synthesis; therefore, the fragments may be employed as intermediates for producing the full-length polypeptides. Fragments or portions of the nucleic acids of the present invention may be used to synthesize full-length nucleic acids of the present invention.

As discussed above, the present invention relates in part to methods for producing and isolating ANT and CypD polypeptides, including human ANT and human CypD polypeptides, as well as ANT fusion proteins and CypD fusion proteins. ANT polypeptides may generally be produced in useful amounts using a nucleic acid expression vector having a promoter operably linked to a polynucleotide encoding an ANT polypeptide. Similarly, CypD polypeptides may generally be produced in useful amounts using a nucleic acid expression vector having a promoter operably linked to a polynucleotide encoding a CypD polypeptide. In preferred embodiments, a nucleic acid expression construct encodes a fusion protein comprising an ANT or CypD polypeptide fused to an energy transfer molecule polypeptide, as provided herein. Although the ANT encoding and CypD encoding nucleic acid expression constructs as described herein may be separate vectors, the invention is not intended to be so limited, such that those familiar with the art will readily appreciate that the ANT and CypD polypeptides and/or fusion proteins may be placed on a single nucleic acid construct. For example, a single nucleic acid expression construct may have polynucleotide sequences encoding ANT and CypD fusion proteins operably linked to a single promoter, or each polynucleotide sequence encoding a fusion protein may have its own operably linked promoter. In either construct, both fusion proteins may be expressed substantially at the same time.

In certain embodiments, for instance, the present invention provides compositions and methods for producing recombinant ANT and CypD polypeptides and fusion proteins through the use of an externally regulated promoter as provided herein. In other embodiments, for example, the present invention may be adapted to include more than one externally regulated promoter to allow, for example, different production levels of ANT polypeptide, relative to CypD polypeptide.

The present invention also pertains in part to the use of ANT and CypD polypeptides, which include full length proteins and polypeptides, fragments, and variants thereof, and further include ANT fusion proteins and CypD fusion proteins, as provided herein. In certain preferred embodiments, such as those described in greater detail below, human ANT and CypD polypeptides may be used in various binding assays, screening assays, functional assays and the like. In certain particularly preferred embodiments, an ANT fusion protein comprises an energy transfer molecule polypeptide, and a CypD fusion protein comprises an energy transfer molecule polypeptide distinct from that present in the ANT fusion protein, wherein selection of suitable energy transfer molecule polypeptides is as provided herein. The expression of recombinant ANT and CypD polypeptides can be achieved at levels that enable the use of the ANT and CypD polypeptide products in such assays, and the present invention provides assays (including high throughput assays) for identifying agents (including, e.g., ANT ligands and CypD ligands) that alter the interaction between ANT and CypD polypeptides and/or fusion proteins. The present invention further relates in part to agents and ligands of ANT and CypD polypeptides. Such agents may, for example, enhance or impair any ANT and CypD functions known to the art, including but not limited to those described herein.

Energy Transfer Molecules and Fusion Proteins

As discussed above, the present invention also pertains in part to compositions and methods for producing and isolating ANT and CypD polypeptides, including ANT and CypD fusion proteins, for identifying agents that interact with ANT, CypD, and ANT/CypD complexes. Certain aspects of the present invention are based on the discovery that fluorescence resonance energy transfer (FRET) techniques can be used to detect ANT-CypD interactions between ANT and CypD fusion proteins, wherein one fusion protein comprises an ANT polypeptide fused to an energy transfer molecule polypeptide such as a suitable energy transfer donor polypeptide sequence, domain or region, and the other fusion protein comprises a CypD polypeptide fused to an energy transfer molecule polypeptide such as a suitable energy transfer acceptor polypeptide sequence, domain or region. As another non-limiting example, one fusion protein may comprise an ANT polypeptide fused to an energy transfer molecule polypeptide such as a suitable energy transfer acceptor polypeptide sequence, domain or region and the other fusion protein may comprise a CypD polypeptide fused to an energy transfer molecule polypeptide such as a suitable energy transfer donor polypeptide sequence, domain or region.

The energy emission spectrum of an energy transfer donor molecule (e.g., an energy transfer molecule polypeptide that is a suitable energy donor) should at least partially overlap the energy absorption spectrum of the energy transfer acceptor molecule (e.g., an energy transfer molecule polypeptide that is a suitable energy acceptor) with which it is paired for use in FRET, so that energy transfer from the donor to the acceptor can occur. Typically, an energy transfer donor molecule has an emission peak wavelength (herein, "λD (em)") that is within several nm of the excitation peak wavelength of the energy transfer acceptor molecule herein, "λA(ex)"). That is, the difference between D(em) and A(ex) is typically from about 70 nm to about 20 nm or less, with typical values for the difference $$\Delta \approx \lambda D(em) - \lambda A(ex)$$

being $\leq 60$ nm, $\leq 50$ nm, $\leq 40$ nm, $\leq 30$ nm, $\leq 25$ nm, $\leq 20$ nm, $\leq 15$ nm, $\leq 10$ nm, $\leq 5$ nm or $\leq 1$ nm.

When excitation or emission is plotted as a function of wavelength, however, certain compounds that are suitable for use as energy transfer donor molecules or energy transfer acceptor molecules may have broad peaks, such that energy may be detectably transferred between certain paired energy transfer donor and energy transfer acceptor molecules having a larger difference between D(em) and A(ex) than that just described. For example, certain donor-acceptor pairs may be suitable for energy transfer methodologies as provided herein even where energy transfer between them is highly inefficient (i.e., where one or both of the energy transfer donor and acceptor may be used with light having a wavelength that is far from the excitation peak wavelength and/or the emission peak wavelength for the energy transfer molecule), so long as the energy transfer donor and the energy transfer acceptor are within sufficient proximity of one another for detectable energy transfer to occur. Those having ordinary skill in the art can readily determine without undue experimentation when fluorescence resonance energy transfer is present, such that selection of appropriate (i.e., suitable) energy transfer donor-acceptor pairs may be accomplished according to established criteria and the teachings provided herein.

For example, routine screening may be employed by combining in a test solution (e.g., in the absence of a host cell as provided herein) at least a candidate energy transfer donor molecule and a candidate energy transfer acceptor molecule (for example, donor and acceptor energy transfer molecule polypeptides as disclosed herein), for purposes of determining whether a detectable FRET signal can be generated. For certain energy transfer donor-acceptor polypeptide combinations, specific generation of a FRET signal may depend on binding of the functional domains to which each of the donor and the acceptor polypeptides are fused, for example, binding interactions between ANT and CypD polypeptides as provided herein. Screening of certain such donor-acceptor pairs for their facilitation of a detectable FRET signal in solution may further include adding to the test solution at least one suitable biomolecule such as a protein- or peptide-, a lipid-, a nucleic acid- or a carbohydrate-containing species that will be selected by the person having ordinary skill in the art based upon familiarity with the nature of the functional domains (e.g., co-factors or other conditions favoring ANT-CypD binding). Without wishing to be bound by theory, in order to detect a FRET signal the concentrations of the energy transfer donor and acceptor molecules used in such a pilot experiment may in certain such instances exceed those to be used in the subject invention methods as provided herein. However, similarly detectable concentrations of such energy transfer molecules may accumulate in a host cell as described herein, for example in a subcellular compartment of such host cell such as a mitochondrion, following induction of the promoter(s) which regulate expression of the fusion proteins comprising energy transfer molecule polypeptides. Those familiar with the art will also readily appreciate that the fluorescence spectral properties of energy transfer donor and energy transfer acceptor molecules (e.g., energy transfer molecule polypeptides) may vary as a function of solution and sample conditions employed (e.g., solvent selected, solvent and ionic strength, pH, nature of the sample, etc.).

Another criterion useful in selecting a suitable energy transfer donor-acceptor pair (such as paired energy transfer molecule donor and acceptor polypeptides) for use according to the present invention is that the emission signal generated by the excited energy transfer acceptor must be capable of being distinguished from the emission signal generated by the excited energy transfer donor. An emission signal from an excited donor can be so distinguished if, for example, (1) the wavelength of the emission signal from the excited acceptor is sufficiently distinct from the wavelength of the emission signal from the excited donor, or (2) the acceptor quenches the emission signal from the excited donor.

Examples of proteins that can serve as energy transfer donor and acceptor molecule polypeptides include fusion proteins comprising a "FLASH" (fluorescein arsenical helix binder) sequence (Griffin et al., *Science* 281:269–272, 1998), or an aequorin protein or a green fluorescent protein (GFP) sequence (Kendall et al., *Trends in Biotechnology* 16:216–224, 1998, and references cited therein). As used herein, the term "green fluorescent protein" encompasses the wildtype green fluorescent protein (wildtype GFP), as well as blue-shifted, cyan-shifted, red-shifted and yellow-shifted derivatives of wildtype GFP (designated, respectively, BFP, CFP, RFP and YFP; see published PCT application WO 98/06737). Table 2 (see Example 17, infra) provides examples of representative GFP energy transfer molecule polypeptide donor-acceptor pairs and includes descriptions of amino acid substitutions at indicated numbered amino acid sequence positions in various GFP derivatives using the single-letter code for amino acids. Table 2 also shows the respective excitation and emission peak wavelengths of these GFPs.

In order to generate an expression construct that encodes a fusion protein comprising an ANT polypeptide or a CypD polypeptide fused to an energy transfer molecule polypeptide such as an aequorin, GFP or FLASH polypeptide, an expression vector comprising a polynucleotide appropriate for gene expression can be manipulated to comprise (1) a first nucleic acid encoding an ANT polypeptide or a CypD polypeptide as provided herein, and (2) a second nucleic acid encoding an aequorin polypeptide, a GFP derivative or a FLASH polypeptide, wherein the first and second nucleic acids are linked so as to have a common reading frame that comprises both nucleic acids.

As discussed below, such polypeptides may he used within FRET assays to detect protein-protein interactions, including binding events (see Mahajan et al., *Nature Biotechnology* 16:547–562, 1998) or protein cleavage (see Xu et al., *Nucl. Acids Res.* 26:2034–2035, 1998). Such assays employ two fluorescent energy transfer molecules (e.g., energy transfer molecule polypeptides), selected, for example, so that the emission spectrum of one energy transfer molecule (the energy donor fluorophore) overlaps with the excitation spectrum of the other energy transfer molecule (the energy acceptor fluorophore), as provided herein. Accordingly, the FRET-based screening methods provided herein generally employ two energy transfer molecules that have overlapping excitation/emission spectra, such that they interact in the host cell by transferring fluorescence energy. In preferred embodiments, the energy transfer molecule may be a fluorescent, phosphorescent, bioluminescent, or chemiluminescent protein, polypeptide or peptide, and more preferably a fluorescent protein, polypeptide or peptide. An energy transfer molecule, for example, an energy transfer molecule polypeptide sequence, such as may be fused to an ANT and/or a CypD polypeptide to form a detectable ANT or CypD fusion protein as described herein, may be detected when it is exposed to an excitation energy that may be physical (e.g., photons or electrons) or chemical (e.g., an enzyme or inducer). In a preferred embodiment, the excitation energy is chemical, more preferably the excitation energy is physical, and most preferably the excitation energy is light with a wavelength ranging from about 300 nm to about 650 nm.

As described herein, the invention provides ANT and CypD fusion proteins comprising ANT or CypD polypeptides fused to an additional functional or non-functional polypeptide sequence that permits, for example by way of illustration and not limitation, detection, isolation and/or purification of the ANT and CypD fusion proteins. For instance, an additional functional polypeptide sequence may be an energy transfer molecule polypeptide as provided herein. ANT and CypD fusion proteins described herein may be detected by FRET, fluorescence, phosphorescence, bioluminescence, or chemiluminescence, and include fusion proteins that may in certain embodiments be detected, isolated and/or purified by protein-protein affinity (e.g., receptor-ligand), metal affinity or charge affinity methods. In certain other embodiments the subject invention fusion proteins may be detected by specific protease cleavage of a fusion protein having a sequence that comprises a protease recognition sequence, such that the ANT and CypD polypeptides may be separable from the additional polypeptide sequence. In particularly preferred embodiments, for example, each ANT and/or CypD polypeptide sequence is fused in-frame to an energy transfer molecule polypeptide sequence. Other polypeptide sequences present in ANT and CypD fusion proteins may facilitate affinity detection and isolation of ANT and CypD polypeptides and may include, for example, poly-His or the defined antigenic peptide epitopes described in U.S. Pat. No. 5,011,912 and in Hopp et al., (1988 *Bio/Technology* 6:1204) (e.g., FLAG® epitope tag DYKDDDDK, SEQ ID NO: 55), or the XPRESS™ epitope tag (DLYDDDDK, SEQ ID NO: 56; Invitrogen, Carlsbad, Calif.). The affinity sequence may be a hexa-histidine tag as supplied, for example, by a pBAD/His (Invitrogen) or a pQE-9 vector to provide for purification of the mature polypeptide fused to the marker in the case of a bacterial host. Alternatively, the affinity sequence may be a hemaglutinin (HA) tag when mammalian host cells, for example COS-7 cells, are used. The HA tag corresponds to an antibody defined epitope derived from the influenza hemaglutinin protein (Wilson et al., 1984, *Cell* 37:767).

ANT and CypD fusion proteins may further comprise immunoglobulin constant region polypeptides added to ANT and CypD to facilitate detection, isolation and/or localization of ANT and CypD. The immunoglobulin constant region polypeptide preferably is fused to the C-terminus of an ANT or CypD polypeptide. General preparation of fusion proteins comprising heterologous polypeptides fused to various portions of antibody-derived polypeptides (including the Fc domain) has been described, e.g., by Ashkenazi et al. (1991 *Proc. Nat. Acad. Sci. USA*, 88:10535) and Byrn et al. (1990 *Nature*, 344:677). A gene fusion encoding the ANT:Fc or the CypD:Fc fusion protein is inserted into an appropriate expression vector. In certain embodiments of the invention, ANT:Fc and CypD:Fc fusion proteins may be allowed to assemble much like antibody molecules, whereupon interchain disulfide bonds form between Fc polypeptides, yielding dimeric ANT fusion proteins and dimeric CypD fusion proteins.

ANT and CypD fusion proteins having specific binding affinities for pre-selected antigens by virtue of fusion polypeptides comprising immunoglobutin V-region domains encoded by DNA sequences linked in-frame to sequences encoding ANT and CypD are also within the scope of the invention, including variants and fragments thereof, as provided herein. General strategies for the construction of fusion proteins having immunoglobulin V-region fusion polypeptides are disclosed, for example, in EP 031 8554; U.S. Pat. Nos. 5,132,405; 5,091,513; and 5,476,786.

Fusion proteins may in certain embodiments comprise an ANT or CypD polypeptide fused to one or more other polypeptides having desirable affinity properties (e.g., receptor-ligand). Some specific examples of polypeptides having affinity properties include, without limitation, enzymes such as glutathione-S-transferase (GST) and *Staphylococcus aureus* protein A polypeptide. Protein A encoding nucleic acids and their use in constructing fusion proteins having affinity for immunoglobulin constant regions are disclosed generally, for example, in U.S. Pat. No. 5,100, 788. Other useful affinity polypeptides for construction of ANT and CypD fusion proteins may include streptavidin fusion proteins, as disclosed, for example, in WO 89/03422; U.S. Pat. Nos. 5,489,528; 5,672,691; WO 93/24631; U.S. Pat. Nos. 5,168,049; 5,272,254 and elsewhere, and avidin fusion proteins (see, e.g., EP 511,747). As provided herein and in the cited references, ANT and CypD polypeptide sequences may be fused to fusion polypeptide sequences that may be full length fusion polypeptides and that may alternatively be variants or fragments thereof.

Nucleic Acid Expression Constructs

The nucleic acid constructs of the present invention may be in the form of RNA or in the form of DNA, such as cDNA, genomic DNA or synthetic DNA. DNA may be double-stranded or single-stranded, and if single stranded may be the coding strand or non-coding (anti-sense) strand. Coding sequences for mitochondrial pore components as provided herein are known in the art (see, e.g., Table 1, infra). For example by way of illustration and not limitation, a coding sequence that encodes an ANT or a CypD polypeptide for use according to the invention may be identical to the coding sequence known in the art for any given ANT or Cyp such as CypA or CypD, as described above and, for example, as shown for human ANT1 (SEQ ID:NO: 1), human ANT2 (SEQ ID NO: 2) human ANT3 (SEQ ID NO: 3), human CypA (SEQ ID NO: 26) and human CypD (SEQ ID NO: 39) in FIGS. 1, 7 and 8, or may be a different coding sequence, which, as a result of the redundancy or degeneracy of the genetic code, encodes the same ANT or Cyp polypeptide, as, for example, the cDNAs of FIG. 1, 7 or 8.

The nucleic acid sequences that encode ANT or CypD polypeptides include, but are not limited to, sequences comprising: only the coding sequence for an ANT or CypD polypeptide; a coding sequence for an ANT or CypD polypeptide and additional coding sequence; a coding sequence for an ANT or CypD polypeptide (and optionally additional coding sequence) and a non-coding sequence, such as an intron or non-coding sequence 5' and/or 3' of the coding sequence for the ANT or CypD polypeptide (e.g., a regulatory nucleic acid sequence that may be a regulated, externally regulated or regulatable promoter, enhancer, other transcription regulatory sequence, a repressor binding sequence, a translation regulatory sequence or any other regulatory nucleic acid sequence). Thus, the terms "polynucleotide encoding an ANT polypeptide" and "polynucleotide encoding a CypD polypeptide" encompass polynucleotides that include only coding sequence for the respective polypeptide as well as polynucleotides that include additional coding and/or non-coding sequence(s).

The present invention further relates to variants of the herein described polynucleotides, which may encode fragments, analogs or derivatives of native ANT and CypD polypeptides. For example, the human ANT1, ANT2 and ANT3 polypeptides and the human CypD polypeptide having the deduced amino acid sequences of FIGS. 2 and 8 (SEQ ID NOS: 47–49, 27 and 40) or any ANT and CypD polypeptides may be used. The variants of the nucleic acid sequences encoding ANTs and CypDs may be naturally occurring allelic variants of the nucleic acids or non-naturally occurring variants. As is known in the art, an allelic variant is an alternate form of a nucleic acid sequence which may have at least one substitution, deletion or addition of one or more nucleotides, any of which does not substantially alter the function of the encoded ANT and CypD polypeptides. Thus, the present invention includes, for example, nucleic acids encoding the same ANT and CypD polypeptides as shown in FIGS. 2 and 8 (SEQ ID NOS: 47–49, 27 and 40), as well as variants of such nucleic acids, which variants encode a fragment, derivative or analog of any of the polypeptides of FIGS. 2 and 8 (SEQ ID NOS: 47–49, 27 and 40).

Variants and derivatives of ANT and CypD may be obtained by mutations of nuclcotide sequences encoding ANT and CypD polypeptides, respectively. Alterations of the native amino acid sequence may be accomplished by any of a number of conventional methods. Mutations can be introduced at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion.

Alternatively, oligonucleotide-directed site-specific mutagenesis procedures can be employed to provide an altered gene wherein predetermined codons can be altered by substitution, deletion or insertion. Exemplary methods of making such alterations are disclosed by Walder et al. (*Gene* 42:133, 1986); Bauer et al. (*Gene* 37:73, 1985); Craik (*BioTechniques,* January 1985, 12–19); Smith et al. (*Genetic Engineering: Principles and Methods,* Plenum Press, 1981); Kunkel (*Proc. Natl. Acad. Sci. USA* 82:488, 1985); Kunkel et al. (*Methods in Enzymol.* 154:367, 1987); and U.S. Pat. Nos. 4,518,584 and 4,737,462.

Equivalent DNA constructs that encode various additions or substitutions of amino acid residues or sequences, or deletions of terminal or internal residues or sequences not needed for biological activity are also encompassed by the invention. For example, sequences encoding Cys residues that are not essential for biological activity can be altered to cause the Cys residues to be deleted or replaced with other amino acids, preventing formation of incorrect or undesirable intramolecular disulfide bridges upon renaturation. Other equivalents can be prepared by modification of adjacent dibasic amino acid residues to enhance expression in yeast systems in which KEX2 protease activity is present. EP 212,914 discloses the use of site-specific mutagenesis to inactivate KEX2 protease processing sites in a protein. KEX2 protease processing sites are inactivated by deleting, adding or substituting residues to alter Arg-Arg, Arg-Lys, and Lys-Arg pairs to eliminate the occurrence of these adjacent basic residues. Lys-Lys pairings are considerably less susceptible to KEX2 cleavage, and conversion of Arg-Lys or Lys-Arg to Lys-Lys represents a conservative and preferred approach to inactivating KEX2 sites.

A truncated molecule, for example a truncated ANT or CypD polypeptide or nucleic acid, may be any molecule that comprises less than a full length version of the molecule. In certain preferred embodiments, the present invention provides truncated ANT and CypD polypeptides, and in certain embodiments the invention provides nucleic acids encoding such truncated polypeptides. Truncated nucleic acid molecules have less than the full length nucleotide sequence of a known or described nucleic acid molecule, where such a known or described nucleic acid molecule may be a naturally occurring, a synthetic or a recombinant nucleic acid molecule, so long as one skilled in the art would regard it as a full length molecule.

Thus, for example, truncated nucleic acid molecules that correspond to a gene sequence contain less than the full length gene where the gene comprises coding and non-coding sequences, promoters, enhancers and other regulatory sequences, flanking sequences and the like, and other functional and non-functional sequences that are recognized as part of the gene. In another example, truncated nucleic acid molecules that correspond to a mRNA sequence contain less than the full length mRNA transcript, which may include various translated and non-translated regions as well as other functional and non-functional sequences. In other preferred embodiments, truncated molecules are polypeptides that comprise less than the full length amino acid sequence of a particular protein. As used herein "deletion" has its common meaning as understood by those familiar with the art, and may refer to molecules that lack one or more portions of a sequence from either terminus or from a non-terminal region, relative to a corresponding full length molecule, for example, as in the case of truncated molecules provided herein. Truncated molecules that are linear biological polymers such as nucleic acid molecules or polypeptides may have one or more of a deletion from either terminus of the molecule or a deletion from a non-terminal region of the molecule, where such deletions may be deletions of 1–1500 contiguous nucleotide or amino acid residues, preferably 1–500 contiguous nucleotide or amino acid residues and more preferably 1–300 contiguous nucleotide or amino acid residues.

Analysis of ANT and CypD truncation deletion mutants as provided herein permits identification of ANT and CypD structural domains that are responsible for particular functional properties, including, for example, the polypeptide regions that may mediate CypD binding to ANT, to cyclosporin A and/or to VDAC (Crompton et al., 1998 *Eur. J. Biochem.* 258:729). Thus, the use of ANT and CypD truncation deletion mutants permits molecular fine regulation of binding interactions among mitochondrial molecular components in vitro and/or of mitochondrial function in vivo. Accordingly, in certain embodiments of the invention, detectably altered (e.g., increased or decreased) cellular responses to inducers of MPT in cells transfected with ANT and/or CypD truncation deletion mutants permits correlation of the presence of a particular ANT or CypD structural domain with a particular mitochondrial function (e.g., ETC activity, oxygen consumption, ATP production, altered mitochondrial membrane potential, altered mitochondrial permeability, induction of apoptosis, etc.). In certain other embodiments, detectably altered binding in vitro between isolated recombinant truncated forms of ANT and CypD permits identification of particular ANT and CypD structural domains that contribute to molecular interactions such as recognition and binding and the like. As also described in greater detail herein, truncated ANT and/or CypD polypeptides and nucleic acids provide molecular targets for use in screening assays designed to identify agents that alter ANT and/or CypD functional activities.

The present invention further relates to nucleic acid sequences that hybridize to ANT- or CypD-encoding polynucleotide sequences as provided herein. Preferably, such sequences display at least 70%, preferably at least 90%, and more preferably at least 95% identity to a native ANT or CypD sequence. More preferably, such nucleic acid sequences hybridize under stringent conditions to a native ANT- or CypD-encoding nucleic acid sequence. As used herein; the term "stringent conditions" means hybridization will occur only if there is at least 95% and preferably at least 97% identity between the sequences. The nucleic acid sequences that hybridize to ANT- or CypD-encoding polynucleotides, in preferred embodiments, encode polypeptides that substantially retain a biological function or activity of an ANT or CypD polypeptide encoded by a cDNA of FIG. 1 or 8 (SEQ ID NOS: 1, 57, 3, 26 and 39).

As used herein, two nucleotide sequences are said to "hybridize" under conditions of a specified stringency if stable hybrids are formed. Stringency of hybridization is typically expressed in conditions of ionic strength and temperature at which such hybrids are annealed and washed. Typically "high," "medium" and "low" stringency encompass the following conditions or equivalent conditions thereto: high stringency: 0.1×SSPE or SSC, 0.1% SDS, 65° C.; medium stringency: 0.2×SSPE or SSC, 0.1% SDS, 50° C.; and low stringency: 1.0×SSPE or SSC, 0.1% SDS, 50° C.

The present invention also relates to nucleic acid vectors and constructs that include nucleic acid sequences of the present invention, and in particular to "nucleic acid expression constructs" that include any polynucleotides encoding an ANT or CypD polypeptide as provided above; to host cells that are genetically engineered with vectors and/or constructs of the invention and to the production and use in screens of ANT and CypD polypeptides by biochemical and genetic techniques. ANT and CypD polypeptides may be expressed in mammalian cells, yeast, bacteria or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described, for example, by Sambrook, et al., *Molecular Cloning: A Laboratory Manual,* Second Edition, Cold Spring Harbor, N.Y., (1989), and may include plasmids, cosmids, shuttle vectors, viral vectors and vectors comprising a chromosomal origin of replication as disclosed therein.

The nucleic acid expression constructs of the present invention may encode ANT and/or CypD polypeptides, such as fusion proteins useful in screening for agents that alter MPT, as described herein. Accordingly, nucleic acid expression constructs may comprise a promoter operably linked to a polynucleotide encoding an ANT or CypD polypeptide fused to an energy transfer molecule polypeptide. A host cell, as described below, that expresses both an ANT polypeptide fused to a first energy transfer molecule polypeptide and a CypD polypeptide fused to a second energy transfer molecule polypeptide (and wherein suitable first and second energy transfer molecule polypeptides are selected as described herein) may be used, for example, in a FRET assay to identify agents that alter MPT. Generally, nucleic acid expression vectors include origins of replication and selectable markers permitting detectable transformation of the host cell, e.g., the ampicillin resistance gene of *E. coli* and *S. cerevisiae* TRP1 gene, and a promoter derived from a highly-expressed gene to direct transcription of a downstream structural sequence. Such promoters can be derived from operons encoding glycolytic enzymes such as 3-phosphoglycerate kinase (PGK), α-factor, acid phosphatase, or heat shock proteins, among others. The heterologous structural sequence is assembled in appropriate phase with translation initiation and termination sequences. Optionally, the heterologous sequence can encode a fusion protein including an N-terminal (or a C-terminal) identification peptide imparting desired characteristics, e.g., stabilization or simplified purification of expressed recombinant product.

Expression constructs for bacterial use may be constructed by inserting into an expression vector a structural DNA sequence encoding a desired protein together with suitable translation initiation and termination signals in operable reading phase with a functional promoter. The construct may comprise one or more phenotypic selectable markers and an origin of replication to ensure maintenance of the vector construct and, if desirable, to provide amplification within the host. Suitable prokaryotic hosts for transformation include *E. coli, Bacillus subtilis, Salmonella typhimurium* and various species within the genera Pseudomonas, Streptomyces, and Staphylococcus, although others may also be employed as a matter of choice. Any other plasmid or vector may be used as long as they are replicable and viable in the host.

As a representative but non-limiting example, expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and pGEM1 (Promega Corp., Madison, Wis., USA). These pBR322 "backbone" sections may be combined with an appropriate promoter and the structural sequence to be expressed.

Other vectors and constructs include chromosomal, non-chromosomal and synthetic DNA sequences, e.g., derivatives of SV40; bacterial plasmids; phage DNA; baculovirus; yeast plasmids; yeast artificial chromosomes (YACs); vectors derived from combinations of plasmids and phage DNA; shuttle vectors derived from combinations of plasmids and viral DNA; viral DNA, such as vaccinia, adenovirus, fowl pox virus, and pseudorabies. However, any other vector may be used for preparation of a nucleic acid expression construct as long as it is replicable and viable in the host cell of interest. Further, in some preferred embodiments, nucleic acid expression constructs containing the polynucleotide coding sequence for ANT and CypD polypeptides and fusion proteins may remain extrachromosomal, and in another preferred embodiments the expression constructs may integrate into at least one host cell chromosome.

The appropriate DNA sequence(s) may be inserted into the vector by a variety of procedures. In general, a DNA sequence may be inserted into an appropriate restriction endonuclease site(s) by procedures known in the art. Standard techniques for cloning, DNA isolation, amplification and purification, for enzymatic reactions involving DNA ligase, DNA polymerase, restriction endonucleases and the like, and various separation techniques are those known and commonly employed by those skilled in the art. A number of standard techniques are described, for example, in Ausubel et al. (1993 *Current Protocols in Molecular Biology,* Greene Publ. Assoc. Inc. & John Wiley & Sons, Inc., Boston, Mass.); Sambrook et al. (1989 *Molecular Cloning,* Second Ed., Cold Spring Harbor Laboratory, Plainview, N.Y.); Maniatis et al. (1982 *Molecular Cloning,* Cold Spring Harbor Laboratory, Plainview, N.Y.); and elsewhere.

The coding sequence in the expression vector is operatively linked to at least one appropriate expression control sequences (e.g., a promoter, a regulated promoter and/or an externally regulated promoter) to direct mRNA synthesis. Representative examples of such expression control sequences include LTR or SV40 promoter, the *E. coli* lac or trp, the phage lambda $P_L$ promoter and other promoters known to control expression of genes in prokaryotic or eukaryotic cells or their viruses. Promoter regions can be selected from any desired gene using CAT (chloramphenicol transferase) vectors or other vectors with selectable markers. Two appropriate vectors are pKK232-8 and pCM7. Particular named bacterial promoters include lacd, lacZ, T3, T7, gpt, lambda $P_R$, lambda $P_L$ and trp. Eukaryotic promoters include CMV immediate early, such as is provided in the shuttle vectors pEYFP-C1 and pECFP-N1 (Clontech Laboratories Inc., Palo Alto, Calif.), HSV thymidine kinase, early and late SV40, LTRs from retrovirus, and mouse metallothionein-I. Selection of the appropriate vector and promoter is well within the level of ordinary skill in the art, and preparation of certain particularly preferred nucleic acid expression constructs comprising at least one promoter or regulated promoter operably linked to a polynucleotide encoding an ANT and/or CypD polypeptide is described herein.

In certain preferred embodiments the expression control sequence is an "externally regulated promoter," which includes functional promoter sequences having activity that may be altered (e.g., increased or decreased) by an additional element, agent, molecule, component, co-factor or the like. An externally regulated promoter may comprise, for example, a repressor binding site, an activator binding site or any other regulatory sequence that controls expression of a polynucleotide sequence as provided herein. In certain particularly preferred embodiments, the externally regulated promoter is a tightly regulated promoter that is specifically inducible and that permits little or no transcription of polynucleotide sequences under its control in the absence of an induction signal, as is known to those familiar with the art and described, for example, in Guzman et al. (*J. Bacteriol.,* 1995, 177:4121), Carra et al. (*EMBO J.,* 1993, 12:35), Mayer (*Gene,* 1995, 163:41), Haldimann et al. (*J. Bacteriol.,* 1998, 180:1277), Lutz et al. (*Nuc. Ac. Res.,* 1997, 25:1203), Allgood et al. (*Curr. Opin. Biotechnol.,* 1997, 8:474) and Makrides (*Microbiol. Rev.,* 1996, 60:512). In other preferred embodiments of the invention, an externally regulated promoter is present that is inducible but that may not be tightly regulated. In certain other preferred embodiments a promoter is present in the recombinant expression construct of the invention that is not a regulated promoter; such a promoter may include, for example, a constitutive promoter such as an insect polyhedrin promoter or a yeast phosphoglycerate kinase promoter (see, e.g., Giraud et al., 1998 *J. Mol. Biol.* 281:409). A nucleic acid expression construct may also contain a ribosome binding site for translation initiation and a transcription terminator. A vector may also include appropriate sequences for amplifying expression.

Transcription of a DNA sequence encoding a polypeptide of the present invention by higher eukaryotes may be increased by inserting an enhancer sequence into the vector. Enhancers are cis-acting elements of DNA, usually about from 10 to 300 bp that act on a promoter to increase its transcription. Examples including the SV40 enhancer on the late side of the replication origin bp 100 to 270, a cytomegalovirus early promoter enhancer, the polyoma enhancer on the late side of the replication origin, and adenovirus enhancers.

As noted above, in certain embodiments the vector may be a viral vector such as a retroviral vector. For example, retroviruses from which a retroviral plasmid vector may be derived include, but are not limited to, Moloney Murine Leukemia Virus, spleen necrosis virus, retroviruses such as Rous Sarcoma Virus, Harvey Sarcoma virus, avian leukosis virus, gibbon ape leukemia virus, human immunodeficiency virus, adenovirus, Myeloproliferative Sarcoma Virus, and mammary tumor virus.

A viral vector generally includes one or more promoters. Suitable promoters include, but are not limited to, the retroviral LTR; the SV40 promoter, and the human cytomegalovirus (CMV) promoter described in Miller, et al., *Biotechniques* 7:980–990 (1989), or any other promoter (e.g., cellular promoters such as eukaryotic cellular promoters including, but not limited to, the histone, pol III, and β-actin promoters). Other viral promoters include, but are not limited to, adenovirus promoters, thymidine kinase (TK) promoters, and B19 parvovirus promoters. The selection of a suitable promoter will be apparent to those skilled in the art from the teachings contained herein, and may be from among either regulated promoters or promoters as described above.

A retroviral plasmid vector may be employed to transduce packaging cell lines to form producer cell lines. Examples of packaging cells which may be transfected include, but are not limited to, the PE501, PA317, ψ-2, ψ-AM, PA12, T19-14X, VT-19-17-H2, ψCRE, ψCRIP, GP+E-86, GP+envAm12, and DAN cell lines as described in Miller, *Human Gene Therapy,* 1:5–14 (1990), which is incorporated herein by reference in its entirety. The vector may transduce the packaging cells through any means known in the art. Such means include, but are not limited to, electroporation, the use of liposomes, and $CaPO_4$ precipitation. In one alternative, the retroviral plasmid vector may be encapsulated into a liposome, or coupled to a lipid, and then administered to a host.

A producer cell line generates infectious retroviral vector particles that include a polynucleotide sequence(s) encoding an ANT and/or CypD polypeptide. Such retroviral vector particles then may be employed to transduce eukaryotic cells either in vitro or in vivo. The transduced eukaryotic cells generally express the polynucleotide sequence(s) encoding the ANT and/or CypD polypeptides. Eukaryotic cells that may be transduced include, but are not limited to, embryonic stem cells, embryonic carcinoma cells, as well as hematopoetic stem cells, hepatocytes, fibroblasts, myoblasts, keratinocytes, endothelial cells, and bronchial epithelial cells.

As another example of an embodiment of the invention in which a viral vector is used to prepare nucleic acid expression constructs of ANT and CypD, host cells transduced by a recombinant viral construct directing the expression of ANT or CypD polypeptides may produce viral particles containing expressed ANT and/or CypD polypeptides that are derived from portions of a host cell membrane incorporated by the viral particles during viral budding. In another preferred embodiment, ANT- or CypD-encoding polynucleotide sequences may be cloned into a baculovirus shuttle vector, which is then recombined with a baculovirus to generate a recombinant baculovirus expression construct that is used to infect, for example, Sf9 host cells, as described in *Baculovirus Expression Protocols, Methods in Molecular Biology* Vol. 39, Christopher D. Richardson, Editor, Human Press, Totowa, N.J., 1995; Piwnica-Worms, "Expression of Proteins in Insect Cells Using Baculoviral Vectors," Section II in Chapter 16 in: *Short Protocols in Molecular Biology,* $2^{nd}$ Ed., Ausubel et al., eds., John Wiley & Sons, New York, N.Y., 1992, pages 16–32 to 16–48.

Following transformation of a suitable host strain and growth of the host strain to an appropriate cell density, the selected promoter, if it is an externally regulated promoter, is induced by appropriate means (e.g., temperature shift or chemical induction) and cells are cultured for an additional period. Cells are typically harvested by centrifugation, disrupted by physical or chemical means, and the resulting crude extract retained for further purification. Microbial cells employed in expression of proteins can be disrupted by any convenient method, including freeze-thaw cycling, sonication, mechanical disruption, or use of cell lysing agents; such methods are well known to those skilled in the art.

Host Cells

As noted above, host cells containing the above described ANT and CypD expression constructs as well as methods of preparing the ANT and CypD polypeptides, are also encompassed by the present invention. Host cells are genetically engineered (transduced, transformed or transfected) with one or more vectors and/or expression constructs as described above. Engineered host cells may be cultured in conventional nutrient media modified as appropriate for activating promoters, selecting tansformants or amplifying particular genes such as genes encoding ANT and CypD polypeptides or fusion proteins. Suitable culture conditions for particular host cells will be readily apparent to the ordinarily skilled artisan. To prepare ANT and CypD polypeptides as provided herein, including ANT and/or CypD fusion proteins, host cells containing a nucleic acid expression construct that encodes an ANT or a CypD polypeptide are cultured under conditions to permit expression of the polypeptides. ANT or CypD polypeptide is then recovered from the culture.

Host cells may further be used within assays to detect interactions between ANT and CypD polypeptide. Such host cells generally express ANT and CypD fusion proteins, each comprising an energy transfer molecule. Preferably, the energy transfer molecules have excitation and emission maxima at different wavelengths. In the most preferred embodiments, the energy transfer molecules fused to ANT and CypD polypeptides may be green fluorescent protein (GFP) and color-shifted derivatives thereof, such as YFP, BFP, CFP, and RFP (see published PCT application WO 98/06737). In certain aspects, the energy transfer molecules present within the expressed ANT and CypD polypeptides have an excitation maximum at a wavelength ranging from about 300 nm to 650 nm and an emission maximum ranging from about 350 nm to about 675 nm. In preferred embodiments, one energy transfer molecule has an excitation maximum ranging from about 400 nm to 500 nm and the emission maximum ranging from about 450 nm to 525 nm, and the second energy transfer molecule has an excitation maximum ranging from about 450 nm to 525 nm and an emission maximum ranging from about 500 nm to about 550 nm. In more preferred embodiments, one energy transfer molecule has an excitation maximum at a wavelength of about 433 nm and an emission maximum at a wavelength of about 475 nm and the second energy transfer molecule has an excitation maximum at a wavelength of about 513 nm and an emission maximum at a wavelength of about 527 nm. Preferably, the excitation/emission spectra of the two energy transfer molecules overlap such that binding of the ANT polypeptide to the CypD polypeptide results in detectable energy transfer between the energy transfer molecules.

For example, a host cell for identifying agents that alter MPT may comprise a first nucleic acid expression construct having a promoter operably linked to a polynucleotide encoding human CypD polypeptide fused to a polynucleotide encoding the cyan-shifted derivative of wild-type GFP (CFP, i.e., a first energy transfer molecule polypeptide) and a second nucleic acid expression construct having a promoter operably linked to a polynucleotide encoding human ANT3 (huANT3) polypeptide fused to a polynucleotide encoding the yellow-shifted derivative of wild-type GFP (YFP, i.e., a second energy transfer molecule polypeptide). The CFP energy transfer molecule has an excitation maximum of 433 nm and an emission maximum of 475 nm, while the YFP has an emission maximum of 527 nm. Although light at a wavelength of 433 nm is sufficient to excite CFP, it is not sufficient to excite YFP, but the light emitted by CFP at 475 nm is sufficient to excite YFP to emit light at 527 nm. Thus, a host cell expressing such huANT3 and CypD fusion proteins may be exposed to an appropriate excitation energy (i.e., light at 433 nm) and if the fusion proteins are in close proximity or are interacting, the emission spectrum CFP (donor fluorophor) will overlap the excitation spectrum YFP (acceptor fluorophor), which results in a detectable energy transfer (ie., emission at 527 nm). If the huANT3 and CypD fusion proteins are not in close proximity or are not interacting due to, for example, an agent that disrupts the interaction, then there will be emission at 475 nm, indicating a lack of detectable energy transfer. Either increased or decreased (i.e., quenching) emission may be detected.

A host cell can be a higher eukaryotic cell, such as a mammalian cell, or a lower eukaryotic cell, such as a yeast cell, or the host cell can be a prokaryotic cell, such as a bacterial cell. Representative examples of appropriate host cells according to the present invention include, but need not be limited to, bacterial cells, such as *E. coli,* Streptomyces, *Salmonella typhimurium;* fungal cells, such as yeast; insect cells, such as Drosophila S2 and Spodoptera Sf9; animal cells, such as MDCK, Hep-2, CHO or COS (e.g., COS-7); human cells such as Jurkat or 293 cells; adenoviruses; plant cells, or any suitable cell already adapted to in vitro propagation or so established de novo. The selection of an appropriate host is deemed to be within the scope of those skilled in the art from the teachings herein.

Various mammalian cell culture systems can also be employed to express recombinant protein. Examples of mammalian expression systems include the COS-7 lines of monkey kidney fibroblasts, described by Gluzman, *Cell* 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking non-transcribed sequences, for example as described herein regarding the preparation of ANT and CypD expression constructs. DNA sequences derived from the SV40 splice, and polyadenylation sites may be used to provide the required nontranscribed genetic elements. Introduction of the construct into the host cell can be effected by a variety of methods with which those skilled in the art will be familiar, including but not limited to, for example, calcium phosphate transfection, liposome-mediated transfection, transfection with naked DNA, biolistic particle-mediated transfection, DEAE-Dextran mediated transfection, or electroporation (e.g., Davis et al., 1986 *Basic Methods in Molecular Biology*). According to the present disclosure, and as will be appreciated by those having ordinary skill in the art, in certain embodiments at least one nucleic acid expression construct in a host cell may be extrachromosomal, while in certain embodiments at least one nucleic acid expression construct in a host cell may be integrated into a host cell chromosome. In certain embodiments the host cell chromosome comprises a nuclear chromosome and in certain other embodiments the host cell chromosome comprises a mitochondrial chromosome, as described above.

In some preferred embodiments, host cells may be cybrids (e.g., cytoplasmic hybrid cells comprising a common nuclear component but having mitochondria derived from different individuals). Methods for preparing and using cybrids are described in U.S. Pat. No. 5,888,438, published PCT applications WO 95/26973 and WO 98/17826, King and Attardi (*Science* 246:500–503, 1989), Chomyn et al. (*Mol. Cell. Biol.* 11:2236–2244, 1991), Miller et al. (*J. Neurochem.* 67:1897–1907, 1996), Swerdlow et al. (*Annals of Neurology* 40:663–671, 1996), Cassarino et al. (*Biochim. Biophys. Acta* 1362:77–86, 1997), Swerdlow et al. (*Neurology* 49:918–925, 1997), Sheehan et al. (*J. Neurochem.* 68:1221–1233, 1997) and Sheehan et al. (*J. Neurosci.* 17:4612–4622, 1997).

As will be appreciated by those of ordinary skill in the art, in certain situations it may be desirable to use host cells in which endogenous ANT and/or CypD expression is compromised. For example, detection of particular ANT- and/or CypD-encoding nucleic acid sequences or ANT and/or CypD polypeptides that are highly similar to those encoded by the host cell genome may be facilitated by inhibiting host cell ANT and/or CypD gene expression. As another example, where functional activity of an exogenously introduced recombinant ANT and CypD polypeptides is to be determined in a host cell, it may also be advantageous to inhibit endogenous host cell ANT and/or CypD gene expression.

Thus, in certain preferred embodiments of the invention, host cells may lack at least one isoform of an endogenous ANT and/or CypD, and in certain preferred embodiments the host cells may lack all endogenous ANT and/or CypD isoforms. For example, in the yeast system described by Giraud et al. (1998 J. Mol. Biol. 281:409) a *S. cerevisiae* triple null mutant is described that lacks all three yeast ANT isoforms and is unable to grow under anaerobic conditions. In other preferred embodiments, expression in host cells of at least one gene encoding an endogenous ANT and/or CypD isoform is substantially impaired. Substantial impairment of endogenous ANT and CypD isoform expression may be achieved by any of a variety of methods that are well known in the art for blocking specific gene expression, including site-specific or site-directed mutagenesis as described above, antisense inhibition of gene expression, ribozyme mediated inhibition of gene expression and generation of mitochondrial DNA depleted ($\rho^0$) cells.

Identification of oligonucleotides and ribozymes for use as antisense agents and DNA encoding genes for targeted delivery for genetic therapy involve methods well known in the art. For example, the desirable properties, lengths and other characteristics of such oligonucleotides are well known. Antisense oligonucleotides are typically designed to resist degradation by endogenous nucleolytic enzymes by using such linkages as: phosphorothioate, methylphosphonate, sulfone, sulfate, ketyl, phosphorodithioate, phosphoramidate, phosphate esters, and other such linkages (see, e.g., Agrwal et al., *Tetrehedron Lett.* 28:3539–3542 (1987); Miller et al., *J. Am. Chem. Soc.* 93:6657–6665 (1971); Stec et al., *Tetrehedron Lett.* 26:2191–2194 (1985); Moody et al., *Nucl. Acids Res.* 12:4769–4782 (1989); Uznanski et al., *Nucl. Acids Res.* (1989); Letsinger et al., *Tetrahedron* 40:137–143 (1984); Eckstein, *Annu. Rev. Biochem.* 54:367–402 (1985); Eckstein, *Trends Biol. Sci.* 14:97–100 (1989); Stein In: *Oligodeoxynuleotides, Antisense Inhibitors of Gene Expression,* Cohen, Ed, Macmillan Press, London, pp. 97–117 (1989); Jager et al., *Biochemistry* 27:7237–7246 (1988)).

Antisense nucleotides are oligonucleotides that bind in a sequence-specific manner to nucleic acids, such as mRNA or DNA. When bound to mRNA that has complementary sequences, antisense prevents translation of the mRNA (see, e.g., U.S. Pat. No. 5,168,053 to Altman et al.; U.S. Pat. No. 5,190,931 to Inouye, U.S. Pat. No. 5,135,917 to Burch; U.S. Pat. No. 5,087,617 to Smith and Clusel et al. (1993) *Nucl. Acids Res.* 21:3405–3411, which describes dumbbell antisense oligonucleotides). Triplex molecules refer to single DNA strands that bind duplex DNA forming a colinear triplex molecule, thereby preventing transcription (see, e.g., U.S. Pat. No. 5,176,996 to Hogan et al., which describes methods for making synthetic oligonucleotides that bind to target sites on duplex DNA).

According to this embodiment of the invention, particularly useful antisense nucleotides and triplex molecules are molecules that are complementary to or bind the sense strand of DNA or mRNA that encodes an ANT or CypD polypeptide, or a protein mediating any other process related to expression of endogenous ANT and/or CypD genes, such that inhibition of translation of mRNA encoding the ANT and/or CypD polypeptide is effected.

A ribozyme is an RNA molecule that specifically cleaves RNA substrates, such as mRNA, resulting in specific inhibition or interference with cellular gene expression. There are at least five known classes of ribozymes involved in the cleavage and/or ligation of RNA chains. Ribozymes can be targeted to any RNA transcript and can catalytically cleave such transcripts (see, e.g., U.S. Pat. Nos. 5,272,262; 5,144,019; and 5,168,053, 5,180,818, 5,116,742 and 5,093,246 to Cech et al.). According to certain embodiments of the invention, any such ANT or CypD mRNA-specific ribozyme, or a nucleic acid encoding such a ribozyme, may be delivered to a host cell to effect inhibition of ANT and/or CypD gene expression. Ribozymes, and the like may therefore be delivered to the host cells by DNA encoding the ribozyme linked to a eukaryotic promoter, such as a eukaryotic viral promoter, such that upon introduction into the nucleus, the ribozyme will be directly transcribed.

As used herein, expression of a gene encoding an endogenous ANT or CypD isoform is substantially impaired by any of the above methods for inhibiting when cells are substantially but not necessarily completely depleted of functional DNA or functional mRNA encoding the endogenous ANT and CypD isoform, or of the relevant ANT and CypD polypeptide. ANT and CypD isoform expression is substantially impaired when cells are preferably at least 50% depleted of DNA or mRNA encoding the endogenous ANT and CypD (as measured using high stringency hybridization as described above) or depleted of ANT and CypD polypeptide (as measured by Western immunoblot as described herein, see also, e.g., Giraud et al. 1998 *J. Mol Biol.* 281:409); and more preferably at least 75% depleted of endogenous ANT and CypD DNA, mRNA or polypeptide. Most preferably, ANT and CypD isoform expression is substantially impaired when cells are depleted of >90% of their endogenous ANT and CypD DNA, mRNA, or polypeptide.

Alternatively, expression of a gene encoding an endogenous ANT and/or CypD isoform may be substantially impaired through the use of mitochondrial DNA depleted $\rho^0$ cells, which are incapable of mitochondrial replication and so may not continue to express functional ANT and CypD polypeptides. Methods for producing $\rho^0$ cells are known and can be found, for example in PCT/US95/04063, which is hereby incorporated by reference.

Screening Assays and Kits

The present invention provides compositions, methods and kits for use in identifying agents that alter mitochondrial permeability transition (MPT). Such screens and assays are designed to detect an effect of a candidate agent on binding between ANT and CypD polypeptides, such as fusion proteins. Without wishing to be bound by theory, in view of an apparent interaction between ANT and CypD that may in part regulate MPT as described above, assays based on ANT-CypD binding in vivo (e.g., in an intact host cell) and in vitro (e.g., direct binding of isolated ANT and CypD) may provide a measure of MPT.

As used herein, the term "screening" refers to the use of assays designed to identify agents that alter (e.g., increase or decrease) MPT. Briefly, ANT and CypD polypeptides are contacted with a candidate agent, and the effect of the agent on the interaction between ANT and CypD is determined. Such assays may be performed within host cells expressing ANT and CypD polypeptides, or using isolated ANT and CypD polypeptides. The effect on ANT-CypD binding or interaction is then monitored and compared to a control assay in the absence of the candidate agent (e.g., that has been treated with the vehicle used to deliver the agent). Detection may be direct (e.g., by a competitive binding assay) or indirect (e.g., by detection of mitochondrial function or ANT polypeptide binding to CypD polypeptide).

A candidate agent may alter MPT directly (e.g., by physical contact with ANT, CypD, and/or ANT-CypD complexes) or indirectly (e.g., by interaction with one or more additional molecular components, such as mitochondrial molecular components present in a host cell, where such additional components alter ANT-CypD interaction in response to contact with the agent). In some embodiments, the candidate agent may be a peptide, polypeptide, protein or small molecules. Typically, and in more preferred embodiments such as for high throughput screening, candidate agents are provided as "libraries" or collections of compounds, compositions or molecules. Such molecules typically include compounds known in the art as "small molecules" and having molecular weights less than $10^5$ daltons, preferably less than $10^4$ daltons and still more preferably less than $10^3$ daltons. For example, members of a library of test compounds can be administered to a plurality of samples, each containing at least one ANT polypeptide or fusion protein and at least one CypD polypeptide or fusion protein, as provided herein, and then assayed for their ability to alter MPT in a cell-based assay or to enhance or inhibit ANT-CypD binding in a noncell based (e.g., in vitro) assay.

Candidate agents further may be provided as members of a combinatorial library, which preferably includes synthetic agents prepared according to a plurality of predetermined chemical reactions performed in a plurality of reaction vessels. For example, various starting compounds may be prepared employing one or more of solid-phase synthesis, recorded random mix methodologies and recorded reaction split techniques that permit a given constituent to traceably undergo a plurality of permutations and/or combinations of reaction conditions. The resulting products comprise a library that can be screened followed by iterative selection and synthesis procedures, such as a synthetic combinatorial library of peptides (see e.g., PCT/US91/08694 and PCT/US91/04666) or other compositions that may include small molecules as provided herein (see e.g., PCT/US94/08542, EP 0774464, U.S. Pat. Nos. 5,798,035, 5,789,172, 5,751, 629). Those having ordinary skill in the art will appreciate that a diverse assortment of such libraries may be prepared according to established procedures, and tested using a CSP target such as a p95.6/YN52 polypeptide or homolog according to the present disclosure.

In certain aspects, screening methods comprise contacting ANT and CypD polypeptides under conditions and for a time sufficient to permit detectable binding of ANT to CypD. The assay is performed in the presence and absence of a candidate agent, and the effect of the candidate agent on ANT-CypD binding is evaluated by comparing the level of binding of CypD to ANT in the presence and absence of the agent.

There are a variety of assay formats known to those of ordinary skill in the art for detecting binding interactions between polypeptides. See, e.g., Harlow and Lane, *Antibodies: A Laboratory Manual,* Cold Spring Harbor Laboratory, 1988. Within one embodiment, one polypeptide is provided as a component of a particle such as a bead, a matrix, a cell, an organelle (e.g., a mitochondrion or a submitochondrial particle as described in greater detail below) or a membranous vesicle such as a liposome, a proteoliposome, a natural or artificial unilamellar or multilamellar membrane vesicle or the like. Thus, in certain preferred embodiments one polypeptide involved in such binding interactions is associated with a mitochondrion or a submitochondrial particle, and in certain other preferred embodiments such a polypeptide is associated with a liposome or proteoliposome. In other preferred embodiments such a polypeptide is associated with a solid-phase matrix. For example, in one embodiment at least one polypeptide is provided immobilized on a solid support prior to contact with the other polypeptide. Polypeptide binding may then be detected using a detection reagent that specifically binds to one or both of the interacting polypeptides (e.g., an antibody or fragment thereof) or using detectable portions of one or both of the polypeptides (e.g., direct detection of a dye, or detection of energy transfer between the two molecules).

A solid support may be any material known to those of ordinary skill in the art. For example, the solid support may be a test well in a microtiter plate or a nitrocellulose or other suitable membrane. Alternatively, the support may be a bead or disc, such as glass, fiberglass, latex or a plastic material such as polystyrene or polyvinylchloride. A polypeptide may be immobilized on the solid support using a variety of techniques known to those of skill in the art, which are amply described in the patent and scientific literature. In the context of the present invention, the term "immobilization" refers to both noncovalent association, such as adsorption, and covalent attachment (which may be a direct linkage between the agent and functional groups on the support or may be a linkage by way of a cross-linking agent). Immobilization by adsorption to a well in a microtiter plate or to a membrane is preferred. In such cases, adsorption may be achieved by contacting the binding agent, in a suitable buffer, with the solid support for a suitable amount of time.

Binding is generally allowed to occur for an amount of time sufficient to detect the bound polypeptide. An appropriate amount of time may generally be determined by assaying the level of binding that occurs over a period of time. After incubating under conditions and for a time sufficient to permit interaction of CypD, ANT, and candidate agent, the level of CypD-ANT binding is detected and compared to the level of binding in the absence of the agent. In some preferred embodiments, ANT and CypD polypeptides are fused to additional polypeptide sequence as provided herein, such as GST, hexa-histidine, and FLAG® polypeptides. Thus, in preferred embodiments additional polypeptide fused to ANT and CypD would be a ligand (e.g., antigen or biotin) that is bound by a receptor (e.g., antibody or streptavidin/avidin), as described herein. In other embodiments, the ANT and CypD fusion proteins may include a protease recognition sequence such that the ANT and CypD polypeptides may be proteolytically separated from the additional polypeptide sequence, as described herein. In yet other embodiments, ANT and CypD may be fused to GFP, or a related mutated GFP (WO 98/06737) such as a YFP, BFP, CFP, or RFP, which may be used, for example, to verify subcellular localization to mitochondria or to detect altered MPT of expressed ANT or CypD fusion proteins encoded by nucleic acid expression constructs according to the invention. Such embodiments of the invention are useful as high throughput screening assays.

Unbound polypeptide is then removed and bound polypeptide is detected using a linked reporter group or a separate detectable marker comprising a reporter group. The method employed for detecting binding depends upon the nature of the reporter group employed. When energy transfer is detected, FRET techniques as described herein may be used. For radioactive groups, scintillation counting or autoradiographic methods are generally appropriate. Spectroscopic methods may be used to detect dyes, luminescent groups and fluorescent groups. Biotin may be detected using avidin, coupled to a different reporter group (commonly a radioactive or fluorescent group or an enzyme). Enzyme reporter groups may generally be detected by the addition of substrate (generally for a specific period of time), followed by spectroscopic or other analysis of the reaction products.

An agent that binds to ANT, CypD, and/or to ANT-CypD complexes may result in a detectable decrease or increase in ANT-CypD binding. Such altered levels of ANT-CypD binding pertain to readily detectable increases or decreases that may vary quantitatively depending on the polypeptides or fusion proteins being monitored and on the particular reagents, instrumentation and methodology selected. Preferably an altered level of ANT-CypD binding refers to a statistically significant increase or decrease.

Other methods for screening for an agent that alters MPT involve FRET in host cells having mitochondria, and that express an ANT fusion protein and a CypD fusion protein, wherein each fusion protein comprises a suitable energy transfer molecule polypeptide. Briefly, such cells are contacted with a candidate agent and an inducer of MPT. The cell is then exposed to an excitation energy and a level of energy transfer between the energy transfer molecules is detected and compared to a reference level such as a reference signal as provided herein, which reference level may be generated in the absence of the candidate agent. By way of non-limiting theory, an agent that binds to ANT, to CypD, to ANT-CypD complexes and/or that otherwise interferes with ANT-CypD interactions may result in a detectable alteration (e.g., decrease or increase) in a FRET signal, for example, by altering ANT-CypD binding as described herein.

Within such assays, the host cells are generally contacted with an inducer of MPT. Such inducers are used in an amount and for a time sufficient to induce MPT, as determined, for example, by measuring a level of energy transfer between an ANT fusion protein and a CypD fusion protein as described herein, or by any other suitable method known in the art. An "inducer of MPT" may be any compound that is known to enhance mitochondrial membrane permeability. Inducers of MPT include, for example, compounds that increase the $Ca^{+2}$ concentration in mitochondria, such as atractyloside, bongkrekic acid, thapsigargin, amino acid neurotransmitters, glutamate, N-methyl-D-aspartic acid, carbachol, ionophores, ionomycin, inducers of potassium depolarization, and "apoptogens" that induce programmed cell death, or "apoptosis" (Green et al., 1998 Science 281:1309). An agent that alters MPT may exert an effect on ANT-CypD binding in the presence and/or absence of an inducer of MPT. In another embodiment, the host cell is further contacted with a second inducer of MPT, preferably an inducer of oxidative stress, most preferably the inducer is selected from ethacrynic acid, buthionine sulfoximine, diamide, menadione, t-butyl hydroperoxide, phenyl-arsine oxide and nitric oxide. An artisan of ordinary skill may be able to determine, without undue experimentation, which combination of inducers of MPT would produce the most detectable signal from the ANT and CypD fusion proteins.

In certain preferred embodiments it may be desirable to compare the signal detected according to the method of the invention with at least one reference signal. In some embodiments the reference signal or signals may be one or more levels of energy transfer that are detectable between suitable energy transfer molecules (e.g., energy transfer molecule polypeptides as provided herein) under specific conditions. Selection of such a suitable reference signal will according to criteria with which those having ordinary skill in the art will be familiar, and may vary depending on the particular assay conditions (e.g., host cell, inducer of MPT, kinetics, inhibitor of MPT, excitation energy, candidate agent) and upon the particular energy transfer molecule donor-acceptor pair employed. For example, a reference signal may be generated by a reference compound such as an energy transfer molecule donor polypeptide or energy transfer molecule acceptor polypeptide or a distinct reporter molecule that is an indicator as provided herein, and may further be generated in the absence or presence of a sample. Such reporter molecules or indicators may include a detectable compound that can be detected as indicative of one or more of a quantity of a detectable component or a location of a detectable component, or the like. For example, by way of illustration and not limitation, a reference signal may be generated by a reporter molecule that permits normalization of a detected energy transfer signal according to the number of cells present (e.g., the reporter may be any of numerous known indicators of cell number, such as selective stains for cell nuclei, for example, propidium iodide or ethidium bromide).

In certain other embodiments, the reference signal is generated by an indicator of the mitochondrial mass, the mitochondrial number or the mitochondrial volume present. For example, where an indicator of mitochondrial mass is selected, a reporter molecule such as nonylacridine orange may be employed. Methods for quantifying mitochondrial mass, volume and/or mitochondrial number are known in the art, and may include, for example, quantitative staining of a representative biological sample. Typically, quantitative staining of mitochondrial may be performed using organelle-selective probes or dyes, including but not limited to mitochondrion selective reagents such as fluorescent dyes that bind to mitochondrial molecular components (e.g., nonylacridine orange, MitoTrackers™) or potentiometric dyes that accumulate in mitochondria as a function of mitochondrial inner membrane electrochemical potential (see, e.g., Haugland, 1996 Handbook of Fluorescent Probes and Research Chemicals—Sixth Ed., Molecular Probes, Eugene, Oreg.). As another example, mitochondrial mass, volume and/or number may be quantified by morphometric analysis (e.g., Cruz-Orive et al., 1990 Am. J. Physiol. 258:L148; Schwerzmann et al., 1986 J. Cell Biol. 102:97). These or any other means known in the art for quantifying mitochondrial mass, volume and/or mitochondrial number in a sample are within the contemplated scope of the invention. For example, the use of such quantitative determinations for purposes of calculating mitoebondrial density is contemplated and is not intended to be limiting. In certain highly preferred embodiments, mitochondrial protein mass in a sample is determined using well known procedures. For example, a person having ordinary skill in the art can readily prepare an isolated mitochondrial fraction from a biological sample using established cell fractionation techniques, and therefrom determine protein content using any of a number of protein quantification methodologies well known in the art.

In other embodiments, a reference signal may be generated by a reporter molecule that permits normalization of a detected energy transfer signal according to the amount of protein present (e.g., coomassie blue, fluorescamine, bicinchoninic acid) or to the amount of nucleic acid present (e.g., ethidium bromide, acridine orange, methylene blue). As another example, a reference signal may be generated by a detectable reporter molecule that is soluble in a liquid medium containing the sample, but that cannot traverse cellular membranes and so serves as a marker of extracellular medium, for example as an indicator of fluid volume. For example, where extraordinarily sensitive instrumentation (e.g., see infra) may be used to detect FRET signals, such an indicator may permit improved quantitative precision by calibration/normalization of sample volumes. Many compounds that are suitable for use as such reference signals will be known to those familiar with the art, who may select such compounds as sources of a reference signal in a manner dependent on, inter alia, the particular assay conditions (e.g., host cell, inducer of MPT, kinetics, inhibitor of MPT, excitation energy, candidate agent) and upon the particular energy transfer molecule donor-acceptor pair employed.

As used herein, detecting a "relative amount" of a signal may include but is not limited to detecting a signal for purposes of comparing it to a reference signal as provided above. Thus, detecting a relative amount of a signal may refer to detecting only a portion of a signal (e.g., detecting a signal at less than 100% efficiency), or to detecting a signal only a portion of which is generated by energy transfer, or to detecting a portion of a signal relative to a signal detected from another sample such as a control sample, regardless of whether any of such other signals detected are reference signals as provided herein. Detection of a signal according to the methods disclosed herein may include quantification of energy transfer by conventional or arbitrarily assigned units of measure. In certain embodiments, a signal may be detected over a period of time such that one or more behaviors of the signal may be analyzed as a function of time. For instance, in some embodiments described herein, a signal may be detected over a period of time, which refers to any method of detecting a sample in a manner that provides more than a single detection event, such that a correlation of a detected signal with a discrete point in time can be established. Thus, for example, in certain embodiments a change in an amount of a signal may be detected over two or more time points, and a rate of change in the level of signal is determined (e.g., a slope or a rate-of-change of a slope such as a first order derivative is determined, when the signal level is plotted as a function of time). As another example, in certain other embodiments an amount of a signal may be cumulatively determined over a discrete time interval, to provide a summed signal (e.g., an integrated signal). These and other techniques known in the art for analyzing quantitative data, and in particular for analyzing such data having a temporal component, are within the contemplated invention.

Thus, any of the methods provided by the invention can be modified so as to also include a reference signal that correlates with a reference parameter of interest for the purpose of, e.g., standardizing for cell number, quantity of cellular protein or cellular nucleic acids, mitochondrial mass, quantity of mitochondrial protein or mitochondrial nucleic acids, indicator of fluid volume or the like. The reference signal, which can be used as an internal standard, need not result from energy transfer and can involve any signal that can be correlated with the desired reference parameter but which does not interfere with detection of the test/assay signal. In the context of the invention, a reference compound can interfere with the test/assay signal if it generates a signal that cannot be resolved from the test/assay signal, or if it localizes to the same subcellular compartment as the energy transfer donor and acceptor molecule polypeptides and itself acts as an energy transfer acceptor or donor.

An instrument such as FLIPR™ can be set to alternate between reading signals at two different wavelengths with a cycling time of about one second; in this manner, the reference signal and the test/assay signal (e.g., FRET, $\Delta\psi$) can be read over the same time course. However, the reference need not be read at the same time as the test/assay signal. For example, in some aspects of the invention, it is necessary to disrupt the cells in order to detect the reference signal, and this typically necessitates that the reference signal be read after the test or assay has been completed.

Some non-limiting examples of reference signals include the following. After the test or assay, as is known in the art, cellular protein (including mitochondrial protein) can be measured using methods such as the Bradford or Lowry assays, and nucleic acid can be measured via the use of fluorescent dyes such as propidium iodide (PI). Nucleic acids can also be measured in living cells. For example, in digitonin-permeabilized cells, propidium iodide (PI; peak excitation, 536 nm, peak emission, 617 nm when bound to a nucleic acid) binds nuclear and cytoplasmic nucleic acids but cannot access the mitochondrial matrix and the mitochondrial nucleic acids contained therein; PI thus provides a reference signal for quantity of cellular nucleic acids. The permeant compound acridine orange (AO) can be used in living cells to distinguish RNA and DNA as it has distinct excitation/emission spectra depending on the type of nucleic acid to which it is bound (AO:DNA, peak excitation, 500 nm; peak emission, 526 nm; AO:RNA, peak excitation, 460 nm; peak emission, 650 nm). The SYTO stains can also be used to detect nucleic acids in living cells; the manufacturer (Molecular Probes, Inc., Eugene, Oreg.) of the SYTO stains indicates that all of the SYTO stains can access nuclear and cellular nucleic acids and some can also access mitochondrial nucleic acids; one skilled in the art will be able to apply techniques such as, e.g., fluorescent microscopy to determine what types of nucleic acids are detected by the use of a particular SYTO stain. JC-1 green fluorescence and NAO fluorescence can be used to measure mitochondrial mass in living cells (Mancini et al., *Ann. Surg. Oncol.* 5:287–295, 1998; Vayssiere et al., *In Vitro Cell. Dev. Biol.* 28A:763–772, 1992, respectively).

In other embodiments of this assay, the MPT pore may be selectively inhibited by cyclosporin A, which may block MPT by inhibiting cyclophilin D peptidyl-prolyl isomnerase activity (Murphy et al., 1998 in *Mitochondria & Free Radicals in Neurodegenerative Diseases,* Beal, Howell and Bodis-Wollner, Eds., Wiley-Liss, New York, pp. 159–186; White and Reynolds, 1996 *J. Neurosci.* 16:5688) and, therefore, its interaction with ANT. Preferably, the invention provides adding an inhibitor of MPT as a way of generating a second reference level; other inhibitors of MPT include low pH and inducers of high mitochondrial membrane potential.

The ability of an agent to modulate apoptosis may also be assessed. In general, a cell is treated with an apoptogen in the presence and absence of candidate agent, and the effect on apoptosis is evaluated. A variety of apoptogens are known to those familiar with the art and may include by way of illustration and not limitation apoptogens that, when added to cells under appropriate conditions with which those skilled in the art will be familiar, require specific receptors such as the tumor necrosis factor, FasL, glutamate, NMDA, IL-3, corticosterone, mineralcorticoid or glucocorticoid receptor(s). Apoptogens may further include herbimycin A (Mancini et al., 1997 *J. Cell. Biol.* 138:449–469); paraquat (Costantini et al., 1995 *Toxicology* 99:1–2); ethylene glycols; protein kinase inhibitors such as, e.g.: staurosporine, calphostin C, caffeic acid phenethyl ester, chelerythrine chloride, genistein; 1-(5-isoquinolinesulfonyl)-2-methylpiperazine; N-[2-(p-bromocinnamyl)amino)ethyl]-5-5-isoquinolinesulfonamide; KN-93; quercitin; d-erythro-sphingosine derivatives; UV radiation; ionophores such as, e.g., ionomycin, valinomycin and other ionophores known in the art; MAP kinase inducers such as, e.g., anisomycin and anandamine; cell cycle blockers such as, e.g. aphidicolin, colcemid, 5-fluorouracil and homoharringtonine; acetylcholineesterase inhibitors such as, e.g., berberine; anti-estrogens such as, e.g. tamoxifen; pro-oxidants, such as, e.g., tert-butyl peroxide and hydrogen peroxide; free radicals such as, e.g., nitrous oxide; inorganic metal ions, such as, e.g., cadmium; DNA synthesis inhibitors such as, e.g., actinomycin D; DNA intercalators such as, e.g., doxorubicin, bleomycin sulfate, hydroxyurea, methotrexate, mitomycin C, camptothecin, and daunorubicin; protein synthesis inhibitors such as, e.g., cycloheximide, puromycin, and rapamycin; agents that effect microtubule formation or stability such as, e.g.: vinblastine, vincristine, colchicine, 4-hydroxyphenylretinamide, and paclitaxel; and other MPT inducers such as, e.g., Bax protein (Jurgenmeier et al., 1998

PNAS 95:4997–5002), calcium and inorganic phosphate. (Kroemer et al., 1998 *Ann. Rev. Physiol.* 60:619.)

The ability of a candidate agent to inhibit or delay the onset of apoptosis may be assessed using any method known in the art. For example, cells may be examined for morphological, permeability or other changes that are indicative of an apoptotic state. Such changes include, but are not limited to, altered morphological appearance (such as plasma membrane blebbing, cell shape change, loss of substrate adhesion properties or other morphological changes that can be readily detected by those skilled in the art using light microscopy); fragmentation and disintegration of chromosomes (which may be apparent by microscopy and/or through the use of DNA specific or chromatin specific dyes that are known in the art, including fluorescent dyes); and/or altered plasma membrane permeability properties, as may be readily detected through the use of vital dyes (e.g., propidium iodide, trypan blue) or by the detection of lactate dehydrogenase leakage into the extracellular milieu. Within another apoptosis assay, translocation of cell membrane phosphatidylserine (PS) from the inner to the outer leaflet of the plasma membrane may be evaluated by measuring outer leaflet binding by the PS-specific protein annexin (Martin et al., *J. Exp. Med.* 182:1545, 1995; Fadok et al., *J. Immunol.* 148:2207, 1992).

In yet another apoptosis assay, induction of specific protease activity in a family of apoptosis-activated proteases known as the caspases may be measured, for example by determination of caspase-mediated cleavage of specifically recognized protein substrates. Such substrates may include, for example, poly-(ADP-ribose) polymerase (PARP) or other naturally occurring or synthetic peptides and proteins cleaved by caspases that are known in the art (see, e.g., Ellerby et al., 1997 *J. Neurosci.* 17:6165). The synthetic peptide Z-Tyr-Val-Ala-Asp-AFC            (SEQ ID NO: 50), wherein "Z" indicates a benzoyl carbonyl moiety and AFC indicates 7-amino-4-trifluoromethylcoumarin (Kluck et al., 1997 *Science* 275:1132; Nicholson et al., 1995 *Nature* 376:37), is one such substrate. Other substrates include nuclear proteins such as U1-70 kDa and DNA-PKcs (Rosen and Casciola-Rosen, 1997 *J. Cell. Biochem.* 64:50; Cohen, 1997 *Biochem. J.* 326:1).

A further apoptosis assay is based on detection of the mitochondrial protein cytochrome c that has been released by mitochondria in an apoptotic cell (Liu et al., *Cell* 86:147, 1996). Such detection of cytochrome c may be performed spectrophotometrically, immunochemically or by other well established methods for determining the presence of a specific protein. Matrix-assisted laser desorption ionization time-of-flight (MALDI-TOF) mass spectrometry coupled with affinity capture is particularly suitable for such analysis since apo-cytochrome c and holo-cytochrome c can be distinguished on the basis of their unique molecular weights. For example, the Surface-Enhanced Laser Desorption/Ionization (SELDI™) system (Ciphergen, Palo Alto, Calif.) may be used to determined the effect of an agent on cytochrome c release from mitochondria in cells treated with an apoptotic stimulus (e.g., ionomycin, a well known calcium ionophore). In this approach, a cytochrome c specific antibody immobilized on a solid support is used to capture released cytochrome c present in a soluble cell extract. The captured protein is then encased in a matrix of an energy absorption molecule (EAM) and is desorbed from the solid support surface using pulsed laser excitation. The molecular mass of the protein is determined by its time of flight to the detector of the SELDI™ mass spectrometer.

The present invention further provides kits for screening for agents that alter MPT. Such a kit generally comprises an isolated CypD polypeptide, an isolated ANT polypeptide and, optionally, a detection reagent that specifically binds to at least one of CypD or ANT. Preferably, CypD or ANT polypeptides are immobilized on a solid support and the optional detection reagent is an antibody or antigen-binding fragment thereof.

The present invention also provides kits for screening for agents that alter MPT in a cell-based assay. The kits may comprise a host cell, a first nucleic acid expression construct having a promoter operably linked to a polynucleotide encoding an ANT polypeptide fused to a first energy transfer molecule, and a second nucleic acid expression construct having a promoter operably linked to a polynucleotide encoding a CypD polypeptide fused to a second energy transfer molecule, as described herein. The host cell may be a prokaryotic cell or a eukaryotic cell. The first and second energy transfer molecules are preferably GFP, BFP, CFP, RFP or YFP, as described herein.

Therapeutic Methods

Agents that alter MPT, and that preferably also inhibit or delay the onset of apoptosis, may be used for a variety of purposes. For example, such agents may be used to alter MPT in a mitochondrion. The mitochondrion may be isolated or may be present within a cell. Briefly, a mitochondrion is contacted with an agent as described above under conditions and for a time sufficient to alter MPT, Any of a variety of standard techniques may be used to detect changes in MPT in the mitochondrion.

Typically, mitochondrial membrane potential may be determined according to methods with which those skilled in the art will be readily familiar, including but not limited to detection and/or measurement of detectable compounds such as fluorescent indicators, optical probes and/or sensitive pH and ion-selective electrodes (See, e.g., Ernster et al., 1981 *J. Cell Biol.* 91:227s and references cited; see also Haugland, 1996 *Handbook of Fluorescent Probes and Research Chemicals—Sixth Ed.*, Molecular Probes, Eugene, Oreg., pp. 266–274 and 589–594.). For example, by way of illustration and not limitation, the fluorescent probes 2-,4-dimethylaminostyryl-N-methyl pyridinium (DASPMI) and tetramethylrhodamine esters (such as, e.g., tetramethylrhodamine methyl ester, TMRM; tetramethylrhodamine ethyl ester, TMRE) or related compounds (see, e.g., Haugland, 1996, supra) may be quantified following accumulation in mitochondria, a process that is dependent on, and proportional to, mitochondrial membrane potential (see, e.g., Murphy et al., 1998 in *Mitochondria & Free Radicals in Neurodegenerative Diseases,* Beal, Howell and Bodis-Wollner, Eds., Wiley-Liss, New York, pp. 159–186 and references cited therein; and *Molecular Probes On-line Handbook of Fluorescent Probes and Research Chemicals,* at http://www.probes.com/handbook/toc.html). Other fluorescent detectable compounds that may be used in the invention include but are not limited to rhodamine 123, rhodamine B hexyl ester, $DiOC_6(3)$, JC-1 [5,5',6,6'-Tetrachloro-1,1',3,3'-Tetraethylbezimidazolcarbocyanine Iodide] (see Cossarizza, et al., 1993 *Biochem. Biophys. Res. Comm.* 197:40; Reers et al., 1995 *Meth. Enzymol.* 260:406), rhod-2 (see U.S. Pat. No. 5,049,673; all of the preceding compounds are available from Molecular Probes, Eugene, Oreg.) and rhodamine 800 (Lambda Physik, GmbH, Göttingen, Germany; see Sakanoue et al., 1997 *J. Biochem.* 121:29).

Mitochondrial membrane potential can also be measured by non-fluorescent means, for example by using TTP (tetraphenylphosphoniun ion) and a TTP-sensitive electrode (Kamo et al., 1979 *J. Membrane Biol.* 49:105; Porter and Brand, 1995 *Am. J. Physiol.* 269:R1213). Those skilled in the art will be able to select appropriate detectable compounds or other appropriate means for measuring $\Delta\Psi m$. By way of example and not limitation, TMRM is somewhat preferable to TMRE because, following efflux from mitochondria, TMRE yields slightly more residual signal in the endoplasmic reticulum and cytoplasm than TMRM.

As another non-limiting example, membrane potential may be additionally or alternatively calculated from indirect measurements of mitochondrial permeability to detectable charged solutes, using matrix volume and/or pyridine nucleotide redox determination combined with spectrophotometric or fluorimetric quantification. Measurement of membrane potential dependent substrate exchange-diffusion across the inner mitochondrial membrane may also provide an indirect measurement of membrane potential. (See, e.g, Quinn, 1976, *The Molecular Biology of Cell Membranes*, University Park Press, Baltimore, Md., pp. 200–217 and references cited therein.)

Thus, as provided herein, any experimentally measurable consequence for cells containing mitochondria undergoing MPT may be used, including, for example, measurement of the dissipation of $\Delta\Psi$, detection of the loss of mitochondrial intermembrane space proteins such as cytochrome c to the cytoplasm, activation of one or more caspases as a downstream event in the apoptotic signaling cascade (see above), cell death and any other phenotypic, biochemical, biophysical, metabolic, respiratory or other useful parameter the alteration of which may depend on MPT. Agents identified according to the methods of the present invention that are suitable for treatment of a disease associated with altered mitochondrial function may potentiate, impair or alter the frequency and/or occurrence of MPT and/or MPT-related regulatory mechanisms. Particularly preferred are agents that inhibit the appearance of one or more of the above indicators of MPT.

Such agents may also be used to alter survival of a cell. Briefly, a cell is contacted with an agent under conditions and for a time sufficient to modulate cell survival. Cell survival may then be assayed using standard techniques with which those having ordinary skill in the art will be familiar. For example, cell viability and/or cell entry into apoptosis may be used as indicators of cell survival, which may further reflect one or more indicators of altered mitochondrial function such as MPT (Green and Reed, *Science* 281:1309–1312, 1998; Susin et al., *Biochim. et Biophys. Acta* 1366:151–165, 1998). Cells that are suspected of undergoing apoptosis may be examined for morphological, permeability or other changes that are indicative of an apoptotic state. For example by way of illustration and not limitation, apoptosis in many cell types may cause altered morphological appearance such as plasma membrane blebbing, cell shape change, loss of substrate adhesion properties or other morphological changes that can be readily detected by those skilled in the art using light microscopy. As another example, cells undergoing apoptosis may exhibit fragmentation and disintegration of chromosomes, which may be apparent by microscopy and/or through the use of DNA specific or chromatin specific dyes that are known in the art, including fluorescent dyes. Such cells may also exhibit altered membrane permeability properties as may be readily detected through the use of vital dyes (e.g., propidium iodide, trypan blue) or the detection of lactate dehydrogenase leakage into the extracellular milieu. Damage to DNA may also be assayed using electrophoretic techniques (see, for example, Morris et al., *BioTechniques* 26:282–289, 1999). These and other means for detecting apoptotic cells by morphologic, permeability and related changes will be apparent to those familiar with the art.

In another aspect of the apoptosis assays, translocation of cell membrane phosphatidylserine (PS) from the inner to the outer leaflet of the plasma membrane is quantified by measuring outer leaflet binding by the PS-specific protein annexin (Martin et al, *J. Exp. Med.* 182:1545, 1995; Fadok et al., *J. Immunol.* 148:2207, 1992.). In a preferred format, exteriorization of plasma membrane PS is assessed in 96 well plates using a labeled annexin derivative such as an annexin-fluorescein isothiocyanate conjugate (annexin-FITC, Oncogene Research Products, Cambridge, Mass.).

In another aspect of the apoptosis assays, quantification of the mitochondrial protein cytochrome c that has leaked out of mitochondria in apoptofic cells may provide an apoptosis indicator that can be readily determined (Liu et al., *Cell* 86:147–157, 1996). Such quantification of cytochrome c may be performed spectrophotometrically, immunochemically or by other well established methods for detecting the presence of a specific protein. Release of cytochrome c from mitochondria in cells challenged with apoptotic stimuli (e.g., ionomycin, a well known calcium ionophore) can be followed by a variety of immunological methods. Matrix-assisted laser desorption ionization time of flight mass (MALDI-TOF) spectrometry coupled with affinity capture is particularly suitable for such analysis since apo-cytochrome c and holo cytochrome c can be distinguished on the basis of their unique molecular weights. For example, the SELDI system (Ciphergen, Palo Alto, USA) may be utilized to follow the inhibition by mitochondria protecting agents of cytochrome c release from mitochondria in ionomycin treated cells. In this approach, a cytochrome c specific antibody immobilized on a solid support is used to capture released cytochrome c present in a soluble cell extract. The captured protein is then encased in a matrix of an energy absorption molecule (EAM) and is desorbed from the solid support surface using pulsed laser excitation. The molecular weight of the protein is determined by its time of flight to the detector of the SELDI mass spectrometer.

In another aspect of the apoptosis assays, induction of specific protease activity in a family of apoptosis-activated proteases known as the caspases (Thornberry and Lazebnik, *Science* 281:1312–1316, 1998) is measured, for example by determination of caspase-mediated cleavage of specifically recognized protein substrates. These substrates may include, for example, poly-(ADP-ribose) polymerase (PARP) or other naturally occuring or synthetic peptides and proteins cleaved by caspases that are known in the art (see, e.g., Ellerby et al., 1997 *J. Neurosci.* 17:6165). The labeled synthetic peptide Z-Tyr-Val-Ala-Asp-AFC, wherein "Z" indicates a benzoyl carbonyl moiety and AFC indicates 7-amino-4-trifluoromethylcourmarin (Kluck et al., 1997 *Science* 275:1132; Nicholson et al., 1995 *Nature* 376:37), is one such substrate. Another labeled synthetic peptide substrate for caspase-3 consists of two fluorescent proteins linked to each other via a peptide linker comprising the recognition/cleavage site for the protease (Xu et al., *Nucleic Acids Res.* 26:2034–2035, 1998). Other substrates include nuclear proteins such as U1-70 kDa and DNA-PKcs (Rosen and Casciola-Rosen, 1997 *J. Cell. Biochem.* 64:50; Cohen, 1997 *Biochem. J.* 326:1).

In another aspect of the apoptosis assays, the ratio of living to dead cells, or the proportion of dead cells, in a population of cells exposed to an apoptogen is determined as a measure of the ultimate consequence of apoptosis. Living cells can be distinguished from dead cells using any of a number of techniques known to those skilled in the art. By way of non-limiting example, vital dyes such as propidium iodide or trypan blue may be used to determine the proportion of dead cells in a population of cells that have been treated with an apoptogen and a compound according to the invention (see Example 7).

The person having ordinary skill in the art will readily appreciate that there may be other suitable techniques for quantifying cell survival and/or apoptosis, and such techniques for purposes of determining the effects of agents that alter MPT on cell survival, or on the induction and kinetics of apoptosis, are within the scope of the assays disclosed here.

Within other aspects, an agent may be administered to a patient for treatment or prevention of diseases associated with altered mitochondrial function. Preferred agents for such uses inhibit the loss of MPT. Diseases associated with altered mitochondrial function include, but are not limited to, AD, diabetes mellitus; Parkinson's Disease; Huntington's disease; dystonia; Leber's hereditary optic neuropathy; schizophrenia; mitochondrial encephalopathy, lactic acidosis, and stroke (MELAS); cancer; psoriasis; hyperproliferative disorders; mitochondrial diabetes and deafness (MIDD) and myoclonic epilepsy ragged red fiber syndrome. Such diseases may be diagnosed using standard clinical criteria, which are well known in the art.

MPT-altering agents are generally valuable for therapeutic purposes, since they permit treatment of diseases associated with binding or activity of ANT and CypD polypeptides. The agents that alter MPT, by directly enhancing or impairing ANT-CypD binding or by indirectly affecting a mitochondrial molecular component that affect ANT-CypD binding, are preferably part of a pharmaceutical composition when used in the methods of the present invention. The pharmaceutical composition will include at least one of a pharmaceutically acceptable carrier, diluent or excipient, in addition to one or more MPT-altering agents and, optionally, other components.

"Pharmaceutically acceptable carriers" for therapeutic use are well known in the pharmaceutical art, and are described, for example, in *Remingtons Pharmaceutical Sciences,* Mack Publishing Co. (A. R. Gennaro edit. 1985). For example, sterile saline and phosphate-buffered saline at physiological pH may be used. Preservatives, stabilizers, dyes and even flavoring agents may be provided in the pharmaceutical composition. For example, sodium benzoate, sorbic acid and esters of p-hydroxybenzoic acid may be added as preservatives. In addition, antioxidants and suspending agents may be used.

"Pharmaceutically acceptable salt" refers to salts of the compounds of the present invention derived from the combination of such compounds and an organic or inorganic acid (acid addition salts) or an organic or inorganic base (base addition salts). The compounds of the present invention may be used in either the free base or salt forms, with both forms being considered as being within the scope of the present invention.

The pharmaceutical compositions that contain one or more MPT-altering agents may be in any form which allows for the composition to be administered to a patient. For example, the composition may be in the form of a solid, liquid or gas (aerosol). Typical routes of administration include, without limitation, oral, topical, parenteral (e.g., sublingually or buccally), sublingual, rectal, vaginal, and intranasal. The term parenteral as used herein includes subcutaneous injections, intravenous, intramuscular, intrasternal, intrathecal, intracavernous, intrameatal, intraurethral injection or infusion techniques. The pharmaceutical composition is formulated so as to allow the active ingredients contained therein to be bioavailable upon administration of the composition to a patient. Compositions that will be administered to a patient take the form of one or more dosage units, where for example, a tablet may be a single dosage unit, and a container of one or more compounds of the invention in aerosol form may hold a plurality of dosage units.

For oral administration, an excipient and/or binder may be present. Examples are sucrose, kaolin, glycerin, starch dextrins, sodium alginate, carboxymethylcellulose and ethyl cellulose. Coloring and/or flavoring agents may be present. A coating shell may be employed.

The composition may be in the form of a liquid, e.g., an elixir, syrup, solution, emulsion or suspension. The liquid may be for oral administration or for delivery by injection, as two examples. When intended for oral administration, preferred compositions contain, in addition to one or more MPT-altering agents, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

A liquid pharmaceutical composition as used herein, whether in the form of a solution, suspension or other like form, may include one or more of the following adjuvants: sterile diluents such as water for injection, saline solution, preferably physiological saline, Ringer's solution, isotonic sodium chloride, fixed oils such as synthetic mono or digylcerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition is preferably sterile.

A liquid composition intended for either parenteral or oral administration should contain an amount of MPT-altering agent such that a suitable dosage will be obtained. Typically, this amount is at least 0.01 wt % of an MPT-altering agent in the composition. When intended for oral administration, this amount may be varied to be between 0.1 and about 70% of the weight of the composition. Preferred oral compositions contain between about 4% and about 50% of MPT-altering agent(s). Preferred compositions and preparations are prepared so that a parenteral dosage unit contains between 0.01 to 1% by weight of active compound.

The pharmaceutical composition may be intended for topical administration, in which case the carrier may suitably comprise a solution, emulsion, ointment or gel base. The base, for example, may comprise one or more of the following: petrolatum, lanolin, polyethylene glycols, beeswax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device. Topical formulations may contain a concentration of the MPT-altering agent of from about 0.1 to about 10% w/v (weight per unit volume).

The composition may be intended for rectal administration, in the form, e.g., of a suppository which will melt in the rectum and release the drug. The composition for rectal administration may contain an oleaginous base as a suitable nonirritating excipient. Such bases include, without limitation, lanolin, cocoa butter and polyethylene glycol.

In the methods of the invention, the MPT-altering agent(s) may be administered through use of insert(s), bead(s), timed-release formulation(s), patch(es) or fast-release formulation(s). It will be evident to those of ordinary skill in the art that the optimal dosage of the MPT-altering agent(s) may depend on the weight and physical condition of the patient; on the severity and longevity of the physical condition being treated; on the particular form of the active ingredient, the manner of administration and the composition employed. It is to be understood that use of a MPT-altering agent in chemotherapy can involve such an agent being bound to another compound, for example, a monoclonal or polyclonal antibody, a protein or a liposome, which assist the delivery of said compound.

The following Examples are provided by way of illustration and not limitation.

EXAMPLES

Example 1

Cloning and Expression of His-Tagged Human ANT (6xHis-ANT) Proteins in Bacteria

A. PCR Amplification of ANT cDNAs

Total cellular RNA prepared from whole human brain was obtained from a commercial source (Clontech, Palo Alto, Calif.). The RNA was purified by treatment with RNase-free DNase I (Roche Molecular Biochemicals, formerly Boehringer Mannheim Biochemicals, Indianapolis, Ind.) using 1 µl of DNase I (10 U/µl) in a buffer containing 40 mM Trsi-HCl, pH 7.0, 6 mM magnesium chloride and 2 mM calcium chloride for 30 minutes at 37° C. This treatment was followed by two phenol/chloroform extractions, one chloroform extraction and an ethanol precipitation in the presence of sodium acetate. The RNA pellet was collected by centrifugation, washed with 70% ethanol, air dried, and resuspended in RNase-free sterile water. The RNA was reverse transcribed to generate cDNA using RNase H-deficient Reverse Transcriptase (SUPERSCRIPT™; Life Technologies, Rockville, Md.).

ANT cDNAs were amplified by polymerase chain reactions (PCR) in a thermal cycler using the following primers, AMPLITAQ™ DNA Polymerase (Perkin-Elmer, Foster City, Calif.), and reagents and buffers supplied in a GENE-AMP™ PCR Reagent Kit (Perkin-Elmer), according to the manufacturer's instructions. In the following representations of the PCR primers, underlined nucleotides indicate sequences complementary to the 5'-ends and 3'-ends of the ANT cDNAs, double-underlined nucleotides indicate recognition sequences for the restriction enzymes XhoI (recognition sequence: 5'-CTCGAG) and Asp718 (recognition sequence: 5'-GGTACC), and the ANT start codons (ATG) and the reverse complement of the ANT stop codons (TAA) are emboldened.

For human ANT1 (huANT1; SEQ ID NO:1:), primers having the following nucleotide sequence were used:
Forward (sense):

5'-TTATATCTCGAGT
ATGGGTGATCACGCTTGGAGCTTCCTAAAG,
and SEQ ID NO:4

Reverse (antisense):

5'-TATATAGGTACC
TTAGACATATTTTTTGATCTCATCATACAAC SEQ ID NO:5.

For human ANT2 (huANT2; SEQ ID NO:2), primers having the following nucleotide sequence were used:

Forward (sense):

5'-TTATATCTCGAGT
ATGACAGATGCCGCTGTGTCCTTCGCCAAG,
and SEQ ID NO:6

Reverse (antisense):

5'-TATATAGGTACC
TTATGTGTACTTCTTGATTTCATCATACAAG SEQ ID NO:7.

For human ANT3 (huANT3; SEQ ID NO:3), primers having the following nucleotide sequence were used:
Forward (sense):

5'-TTATATCTCGAGT
ATGACGGAACAGGCCATCTCCTTCGCCAAA,
and SEQ ID NO:8

Reverse (antisense):

5'-TATATAGGTACC
TTAGATCACCTTCTTGAGCTCGTCGTACAGG
SEQ ID NO:9.

B. Generation of ANT Expression Constructs

PCR products were digested with the restriction endonucleases XhoI and Asp718 (both enzymes from Roche Molecular Biochemicals) according to the manufacturer's recommendations using manufacturer-supplied reaction buffers. Restricted DNAs were purified by horizontal agarose gel electrophoresis and band extraction using the Ultra-Clean™ GelSpin kit (Mo Bio Laboratories, Inc., Solana Beach, Calif.).

The expression vector pBAD/His ("B" derivative; Invitrogen, Carlsbad, Calif.) was used. This vector contains the following elements operably linked in a 5' to 3' orientation: the inducible, but tightly regulatable, araBAD promoter; optimized E. coli translation initiation signals; an amino terminal polyhistidine (6xHis)-encoding sequence (also referred to as a "His-Tag"); an XPRESS™ epitope-encoding sequence; an enterokinase cleavage site which can be used to remove the preceding N-terminal amino acids following protein purification, if so desired; a multiple cloning site; and an in-frame termination codon.

Plasmid pBAD/His DNA was prepared by digestion with the restriction endonucleases XhoI and Asp718 according to the manufacturer's instructions and subjected to horizontal agarose gel electrophoresis and band extraction using the UltraClean™ GelSpin kit (Mo Bio Laboratories). Restricted ANT cDNAs were ligated with restricted expression vector DNA using T4 DNA ligase (New England Biolabs, Beverly, Mass.) using the manufacturer's reaction buffer and following the manufacturer's instructions. Competent recA1 hsdR endA1E. coli cells (strain TOP10F'; Invitrogen) were transformed with ligation mixtures containing the prokaryotic vector construct according to the manufacturer's instructions. Single colonies were selected and grown in 3–5 ml of LB broth (Sambrook, J., Fritsch, E. F., and Maniatis, T., *Molecular Cloning: A Laboratory Manual,* Cold Spring Harbor Laboratory Press, Cold Spring Harbor, N.Y., 1989) containing 50 µg/ml ampicillin (Roche Molecular Biochemicals). Plasmid DNA was isolated from the bacterial cultures using the WIZARD™ Plus Series 9600 Miniprep Reagents System (Promega, Madison, Wis.).

The recombinant huANT nucleotide sequences present in the expression constructs were determined and their authenticity confirmed relative to the published ANT sequences (FIG. 1; See Neckelmann et al., *Proc. Natl. Acad. Sci. U.S.A.* 84:7580–7584 (1987) for huANT1; Battini et al., *J. Biol. Chem.* 262:4355–4359 (1987) for huANT2, and Cozens et al., *J. Mol. Biol.* 206:261–280 (1989) for huANT3.) by DNA sequencing using the PRISM™ Ready BIG DYE™ Terminator Cycle Sequencing Kit (The Perkin-Elmer Corp., Norwalk, Conn.) and the following sequencing primers:

5'-TATGCCATAGCATTTTTATCC                SEQ ID NO:10, and

5'-CGCCAAAACAGCCAAGCT                   SEQ ID NO:11.

For each human ANT sequence, both primers are located inside the vector sequence adjacent to the DNA insertion. Sequence data were analyzed using the SEQUENCE NAVIGATOR™ analysis software package (Perkin-Elmer). This huANT3 expression construct was named pMK3A-huANT3.

The expression plasmids encoding His-tagged human ANT1, ANT2 and ANT3 are referred to herein as follows: For human ANT1, "pMK1 (His-tagged huANT1)" or "pMK1"; for human ANT2, "pMK2 (His-tagged huANT2)" or "pMK2"; for human ANT3 "pMK3A (His-tagged huANT3" or "pMK3A"; for human ANT3 from which extraneous linker N-terminal amino acids were deleted as detailed below, "pMK3B (His-tagged hu ANT3, shortened epitope linker)" or "pMK3B". Plasmids pMK1, pMK2 and pMK3A have been deposited at the American Type Culture Collection (ATCC; Manassas, Va.) on Nov. 3, 1998, and given the accession numbers ATCC 98969, ATCC 98970 and ATCC 98971, respectively.

The expression constructs comprising nucleotide sequences encoding human ANT1 (pMK1-huANT1) and human ANT2 (pMK2-huANT2) were restriction mapped to confirm their structures. The nucleotide sequences of plasmids pMK1-huANT1 and pMK2-huANT2 are determined using the methods and primers (SEQ ID NOS:10 and 11) described above.

Treatment of the recombinant huANT3 protein expressed from pMK3A-huANT3 with enterokinase liberated the His-Tag/XPRESS™ epitope polypeptide from the huANT3 protein; however, the resultant huANT3 protein composed several extraneous N-terminal amino acids (i.e. Pro-Ser-Ser-Ser-Met (SEQ ID NO: 51), where "Met" indicates the amino acid encoded by the translation initiation codon of huANT3). Although the extraneous amino acids probably have little or no effect on the recombinant huANT3 protein, a derivative expression construct in which the nucleotide sequence encoding the extraneous amino acids were deleted was prepared in the following manner.

The QUIK-CHANGE™ Site-Directed Mutagenesis Kit (Stratagene, La Jolla, Calif.) essentially according to the manufacturer's instructions. Briefly, a reaction mixture comprising purified pMK3A-huANT3 DNA, the mutagenic oligonucleotide primers 5'-<u>GGAGATGGCCTGTTCCGTCAT</u>
        CTTATCGTCATCGTCGTACAGATC      SEQ ID NO:12

(the underlined sequence is the reverse complement of the 5' end of the huANT3 reading frame), and 5'-GATCTGTACGACGATGACGATAAG
        <u>ATGACGGAACAGGCCATCTCC</u>          SEQ ID NO:13

(the underlined sequence corresponds to the 5' end of the huANT3 reading frame), Pfu DNA polymerase and dNTPs in manufacturer-supplied reaction buffer was prepared. The mutagenic oligonucleotide primers were present in excess and cycles of DNA synthesis was carried out in a thermal cycler according to the manufacturer's protocol. The reaction products were treated with the restriction enzyme DpnI, which cleaves methylated and hemi-methylated DNAs but leaves unmethylated DNA (i.e., annealed products of the reaction) intact, and used to transform EPICUREAN COLI™ XL-1-Blue E. coli cells (Stratagene, Inc., La Jolla, Calif.). Plasmid DNA was prepared from twelve randomly selected transformants and the nucleotide sequence of the region containing the multiple cloning site cassette was determined according to the methods described above. Of the twelve plasmids, only one retained the original sequence found in pMK-huANT3, and three contained undesired point mutations. One of the eight "correct" plasmids was chosen and named pMK3B-huANT3.

C. Expression of His-Tagged huANT3

Cultures of E. coli cells containing pMK3A-huANT3 were grown in LB media containing 50 µg/ml ampicillin to mid-log phase ($OD_{600}$~0.5) and induced for 3–4 hours with increasing doses of L-arabinose (i.e., 0.00002%, 0.0002%, 0.002%, 0.02%, and 0.2%). One ml of each culture was centrifuged at 5,000×g for 10 minutes at 4° C. to pellet the cells. Cell pellets were resuspended, and the cells were lysed, by adding 100 µl of Phosphate Buffered Saline (PBS; pH 7.4) containing 1% cholate, 1% n-dodecyl maltoside, and 0.1% 2-mercaptoethanol (in the preceding text, and throughout the specification, unless specified otherwise, all chemicals are from Sigma, St. Louis, Mo.). Total protein content in the lysates was determined using the BCA (bicinchoninic acid; Smith et al., 1985, *Anal. Biochem.* 150;76–85) Protein Assay kit (Pierce Chemical Co., Rockford, Ill.). Ten µg of total protein was loaded per lane onto an SDS polyacrylamide gel, electrophoresed and transferred to a nitrocellulose membrane (HYBOND™ ECL Nitrocellulose Membrane, Amersham Pharmacia Biotech, formerly Amersham Life Sciences, Piscataway, N.J.). Human ANT3 fusion proteins were detected in a western blot using ANT1-XPRESS™ Antibody (Invitrogen) and horseradish peroxidase-conjugated anti-mouse secondary antibody (Amersham Pharmacia Biotech) according to the manufacturers' instructions.

The results are shown in FIG. 3. From left to right in the figure, the following samples are shown: lanes "M", molecular weight markers; lane "0", untransformed E. coli cells; lane "o/n", E. coli comprising pMK3A-huANT3 grown overnight without induction; lane "1"–"5", E. coli comprising pMK3A-huANT3 grown induced with increasing doses of L-arabinose (0.00002%, 0.0002%, 0.002%, 0.02% and 0.2%, respectively). As expected, untransformed (lane 0) and uninduced (lane o/n) E. coli showed no XPRESS™-huANT3 material. However, expression of recombinant ANT3 fusion protein with a molecular weight of 36.6 kD was observed in lanes 3 and 4 (0.002% and 0.02% L-arabinose, respectively). No XPRESS™-huANT3 material was detected in lanes 1 and 2 (0.00002% and 0.0002% L-arabinose, respectively) indicating that the degree of induction was insufficient under these conditions.

Cells that were grown in the presence of the highest concentration of L-arabinose (0.2%, lane 5) began to lyse and died before the time of harvest; consequently, no recombinant protein was detected. This indicated that very high expression of recombinant huANT in E. coli caused cell death, as is sometimes the case during overexpression of heterologous proteins in bacteria.

D. Recombinant huANT3 Localizes to the Bacterial Membrane

Figure 4:
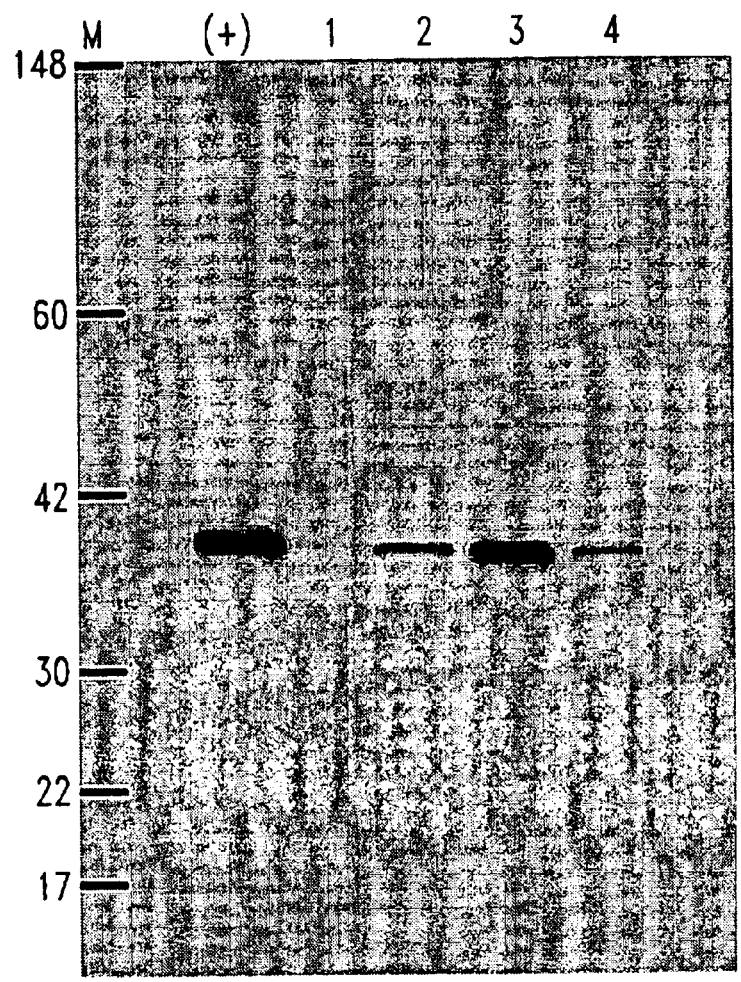
FIG. 4 shows the localization of His-Tagged, XPRESS™-epitope containing huANT3 protein in *E. coli* as determined by Western analysis.

In order to locate the expressed human ANT 3 within *E. coli* cells, cells were grown in culture and induced with L-arabinose as described above, and then fractionated into different compartments (e.g., membranes, inclusion bodies and cytosol). Bacteria were pelleted by centrifugation at 5,000×g for 10 minutes at 4° C. The cell pellets were resuspended in 1/10 volume of cell buffer A (50 mM Tris-HCl, pH 8.0, 2 mM EDTA, 100 ug/ml lysozyme, and 0.1% Triton X-100) and incubated for 15 minutes at 30° C. in an orbital shaker. The cell mixture was sonicated for 2 minutes and membranes were pelleted by centrifugation at 12,000×g for 15 minutes at 4° C. The supernatant, representing the cytosol, was removed for analysis (FIG. 4, lane 4), as was a portion of the pellet containing membranes and inclusion bodies (FIG. 4, lane 3). The remaining portion of the pellet was washed twice with cell buffer B (10 mM Tris-HCl, pH 7.0, 0.1 mM EDTA, and 1 mM DTT) and centrifuged at 12,000×g for 15 minutes at 4° C. The pellet was resuspended in cell buffer C (20 mM Tris-HCl, pH 8.0, 100 mM sodium chloride, and 6 M guanidinium hydrochloride) and incubated for 1 hour at room temperature. The solution was then centrifuged at 12,000×g for 15 minutes at 4° C. The supernatant (containing solubilized inclusion bodies; lane 1, FIG. 4) and the pellet (containing insoluble inclusion bodies; lane 2, FIG. 4) were analyzed by Western blotting as described above.

The results are shown in FIG. 4. Recombinant huANT 3 (molecular weight 36.6 kD) was detected in lanes 2, 3, and 4, as well as the positive control lane (+) (total cell lysate previously tested for presence of ANT3 protein by Western immunoblot analysis, as described above). The greatest amount of recombinant huATN3 was detected in lane 3, which represents the membrane fraction. This indicates that the majority of the huANT3 fusion protein integrated into the *E. coli* cellular membrane. Smaller protein signals were visible in lanes 2 and 4, representing the insoluble inclusion body fraction which might have contained some membranes with integrated ANT 3, and the cytosolic fraction where protein synthesis takes place. No protein was detectable in the soluble inclusion body fraction in lane 1, indicating that controlled expression of ANT3 in the bacteria did not result in the formation of inclusion bodies, which is an undesirable consequence of over-expression of some heterologous proteins in bacteria E. Purification of ANT Proteins ANT proteins, and ANT fusion proteins, produced by the expression systems described herein have been purified using a variety of methods. The purification of ANT proteins, particularly human ANT proteins, is described in this Example.

Regardless of which of following protein purification methods is used, or others that can be derived from the present disclosure, it is important to add sufficient amounts of DNase and RNase to eliminate the viscosity associated with some bacterial lysates (typically 10 µg/mL of each enzyme; both from Roche Biochemicals) when the bacterial cells are lysed (or immediately thereafter). An alternative or additional means by which viscosity has been minimized and ANT solubility has been optimized is vigorous sonication, as opposed to standard sonication, of the lysates. The term "vigorous sonication" refers to, for example, sonication with a Branson Sonifier (Model 450) 2× (30 seconds each time) at 50% duty cycle and 80% output using a tapered, flat-tipped probe (as opposed to sonication with a cup and horn apparatus). Although either type of sonication will suffice, better yields have typically been observed when vigorous sonication has been used.

Furthermore, in various ANT purification methods that have been used, it was often desirable to make the lysate at least 1% Triton-X, in order to solubilize the maximum possible amount of ANT protein, after which insoluble material is removed by a high-speed (i.e., about 100,000 g) centrifugation. Typically, protease inhibitors such as, for example, pepstatin, leupeptin, phenylmethylsulfonyl fluoride (PMSF) and/or aprotinin (all from Sigma) have been present at effective levels (typically 10 µg/mL) during the preparation. Depending on the particular ANT protein or ANT fusion protein being isolated, all four protease inhibitors or any effective combination thereof were used. For example, in preparations of GST-huANT3 fusion proteins, best results were seen when all four protease inhibitors were used, although acceptable results have been obtained when only leupeptin and pepstatin were used.

One method incorporates novel methods with several techniques previously used only for purifying ANT proteins from non-human mammals, i.e., bovine cardiac tissue and rats (Aquila et al., 1982, *Hoppe-Seyler's Z. Physiol. Chem.* 363:345–349; and Sterling, 1986, *Endocrinology* 119:292–295). In brief, bacterial cells expressing a GST-ANT3 fusion protein were lysed by lysozyme treatment, and $^{14}$C-palmityl-CoA (Sigma) was added at a concentration of 50 nmol per gram of *E. coli*. Because it associates with ANT proteins, $^{14}$C-palmityl-CoA acts as a radiolabeled tracer that can be used to follow the ANT protein in subsequent purification steps. The lysates were then sonicated and made 6% Triton X-100 (Sigma) and incubated at 4° C. for 1 hr to solubilize material. A high-speed spin was used to remove insoluble material, and the resulting solute was applied either (1) for small scale preparations, to hydroxyapatite beads (Bio-Rad Laboratories, Hercules, Calif.), or (2) in the case of larger preparations (i.e., ≧1 liter of bacterial culture), to a hydroxyapatite column (Bio-Rad) essentially according to the manufacturer's instructions. Unlike other intramembrane mitochondrial proteins, ANT has a low affinity for hydroxyapatite (Klingenberg et al., 1978, *Biochim. et Biophys. Acta* 503:193–210). The hydroxyapatite column was eluted with Column Buffer A (10 mM MOPS, pH 7.2, 100 Mm NaCl, 9.5% Triton X100) and washed with Column Buffer B (10 mM MOPS, pH 7.2, 100 mM NaCl, 400 mM sodium phosphate). Non-recombinant ANT proteins from non-human species are eluted in the void volume with Column Buffer A, and the GST-huANT3 fusion protein was expected to be present in the void volume as well; Column Buffer B was used to wash the column in the event that GST-huANT3 fusion protein behaves differently. Samples were collected in such a manner as to have a final concentration of 30 of mM octyl glucoside (Calbiochem), a non-ionic detergent that helps solubulize ANT proteins with minimal effect on activity (Sterling, 1986, *Endrocrinol.* 119:292–295). The bead-extracted supernatant or column eluent was collected, and Triton X-100 was removed therefrom using the EXTRACTI-GEL™ affinity matrix (Pierce) essentially according to the manufacturer's instructions (see also Berman et al., 1985, *Biochemistry* 24:7140–7147).

Varying amounts of GST-huANT3 prepared in the above manner were subject to PAGE and the gel was stained using a colloidal blue protein stain (Novex, San Diego, Calif.). The stained gel displayed a single band having a molecular weight corresponding to that predicted for the fusion protein. Based on the intensity of bands from samples of varying volumes, and the known volume of the preparation and minimal sensitivity of the stain, the yield from 100 mL of bacterial culture was estimated to be about 50 ug. In one of the lanes of the gel, approximately 500 ng of protein was loaded, and no contaminating bands were detected; this indicates that the GST-huANT3 protein was from at least about 90% pure to at least about 95% pure.

GST-huANT3 fusion proteins (see preceding Examples) have been purified by this method, and other ANT fusion proteins, including His-tagged huANT3 and other His-tagged ANT proteins, are purified in like fashion. Purified huANT fusion proteins are used to produce purified human ANT proteins as follows.

GST-huANT fusion proteins are further purified via glutathione-agarose beads (Sigma) essentially according to the manufacturer's instructions. In brief, a solution comprising GST-huANT fusion proteins is contacted with glutathione-agarose beads, and the beads are washed to release undesirable contaminants. Next, the [bead:GST-huANT] complexes are treated with an appropriate enzyme, i.e., one that separates the huANT polypeptide from the remainder of the fusion protein. In the case of the GST-huANT3 fusion protein described herein (i.e., that encoded by pMK3C), thrombin (Sigma) cleaves the fusion protein in such a manner so as to produce two polypeptides: a first polypeptide corresponding to the GST moiety, and a second polypeptide which corresponds to human ANT3 with an additional six amino acids (ie., Gly-Ser-Pro-Gly-Ile-Leu, SEQ ID NO: 52) present at its N-terminus.

His-tagged huANT fusion proteins are further purified via Nickel-coated resins (such as, e.g., PROBOND™ $Ni^{2+}$ charged agarose resin; Invitrogen) essentially according to the manufacturer's instructions. In brief, a solution comprising His-tagged huANT fusion proteins is contacted with the Nickel-coated resin, and the resin is washed to release undesirable contaminants. Next, the [resin:His-tagged huANT] complexes are treated with an appropriate enzyme, ie., one that separates the huANT polypeptide from the remainder of the fusion protein. In the case of the His-tagged huANT3 fusion proteins described herein, enterokinase (Sigma, or EKMAX™ from Invitrogen may be used) cleaves the fusion protein in such a manner so as to produce two polypeptides: a first polypeptide comprising the His-tag and XPRESS™ epitope moieties, and a second polypeptide which corresponds to human ANT3. If the expression construct used is pMK3A, the resultant purified human ANT3 protein has an additional four amino acids (i.e., Pro-Ser-Ser-Ser, SEQ ID NO: 53) at its N-terminus. If pMK3B is the expression construct present in the cells from which His-tagged huANT3 is isolated, the resultant purified human ANT3 protein has the sequence of native huANT3, ie., SEQ ID NO:3.

In both of the preceding purification steps, an ANT fusion protein bound to a solid support is treated with an enzyme (i.e., thrombin or enterokinase) that liberates an ANT protein from the remainder of the fusion protein, which remains bound to the solid support. ANT protein is released into the liquid phase which is then collected to generate a solution comprising the ANT protein and some amount of the liberating enzyme. The amount of liberating enzyme needed is minimal because the treatment is catalytic in nature; nevertheless, some enzyme remains in the preparation. If desired, enzyme molecules may be removed from the preparation using any of a variety of means known in the art. For example, an enzyme may be removed from a solution by contacting the solution with a resin conjugated to a ligand having a high affinity for the enzyme. In the case of enterokinases, one such resin is the EK-AWAY™ resin (Invitrogen) which comprises the soybean trypsin inhibitor having a high affinity for enterokinases. Methods of treating GST fusion proteins with thrombin and purifying the desired recombinant protein have been described previously (see, for example, Smith and Corcoran, Unit 16.7 in Chapter 16 in *Short Protocols in Molecular Biology* $2^{nd}$ Ed., Ausubel et al., eds, John Wiley & Sons, New York, N.Y., 1992, pages 16–28 to 16–31. In general, however, any suitable means for separating the liberating enzyme from any given ANT protein may be used.

Example 2

Expression of GST-HuANT3 Fusion Proteins

A. Generation of GST-huANT3 Expression Constructs

Human ANT3 cDNA was amplified from pMK3A-huANT3 by PCR as in Example 1 but using the following primers. In the following representations of PCR primers, underlined nucleotides indicate sequences complementary to the 5'-ends and 3'-ends of the ANT cDNAs and double-underlined nucleotides indicate recognition sequences for the restriction enzymes XhoI (recognition sequence: 5'-CTCGAG) or EcoRI (recognition sequence: 5'-GAATTC).

The primers used for PCR amplification were:
Forward (sense):

5'-CCCGGGG<u>AATTCTG</u><u><u>ATACGGAACAGGCCATCTCC</u></u>,
and                                     SEQ ID NO:14

Reverse (antisense):

5'-CCCGGGCT<u>CGAG</u><u><u>TTAGAGTCACCTTCTTGAGCTC</u></u>
                                     SEQ ID NO:15.

The expression vector pGEX-4T-2 (Amersham Pharmacia Biotech) was used to generate huANT3 fusion proteins comprising an enzymatic polypeptide and an ANT polypeptide. This vector comprises a $lacI^q$ (repressor) gene a tac promoter operably linked to a glutathione S-transferase (GST) gene from *Schistosoma japonicum*. (Smith et al., 1988, *Gene* 67:31–40), the coding sequence of which has been modified to comprise a thrombin cleavage site-encoding nucleotide sequence immediately 5' from a multiple cloning site. GST fusion proteins can be detected by Western blots with anti-GST or by using a colorimetric assay; the latter assay utilizes glutathione and 1-chloro-2-4-dinitrobenzene (CDNB) as substrates for GST and yields a yellow product detectable at 340 nm (Habig et al., 1974, *J. Biol. Chem.* 249:7130–7139). GST fusion proteins produced from expression constructs derived from this expression vector can be purified by, e.g., glutathione affinity chromatography, and the desired polypeptide released from the fusion product by thrombin. Thus, this expression vector provides for the rapid purification of fusion proteins, and release of proteins with relatively few extraneous N-terminal amino acids, although the resulting recombinantly produced protein contains two additional amino acids at the amino terminus (Gly-Ser). The tac promoter may be induced by the addition to cultured cells of, e.g, 1–5 mM isopropyl-beta-D-thiogalactopyranoside (IPTG; Fluka, Milwaukee, Wis.) and provides for high-level expression.

Plasmid pGEX-4T-2 was prepared by digestion with the restriction endonucleases EcoRI and XhoI according to the manufacturer's instructions and subjected to horizontal agarose gel electrophoresis and band extraction using the Ultra-Clean GelSpin kit (Mo Bio Laboratories). Restricted ANT cDNAs were ligated with the restricted expression vector DNA as described in the preceding Example. Single colonies were selected for grown in 3–5 ml of LB broth containing 50 ug/ml ampicillin (Roche Molecular Biochemicals), and plasmid DNA was isolated from the bacterial cultures using the WIZARD™ Plus Series 9600 Miniprep Reagents System (Promega). To confirm their authenticity, the recombinant huANT nucleotide sequences present in the pGEX derivative plasmid were determined as described in the preceding Example using the previously described oligonucleotide primers and 5' and 3' pGEX Sequencing Primers (Amersham Pharmacia Biotech).

The resultant GST-huANT3 expression construct was named pMK3C-GST-huANT3 (also referred to herein as pMK3C). Plasmid pMK3C has been deposited at the American Type Culture Collection (ATCC; Manassas, Va.) on Nov. 3, 1998, and given the accession number ATCC 98973. Thrombin treated recombinant huANT3 protein produced from the pMK3C-GST-huANT3 expression construct includes several extraneous N-terminal amino acids, i.e., Gly-Ser-Pro-Gly-Ile-Leu-Met, (SEQ ID NO: 54), where "Met" indicates the amino acid encoded by the translation initiation codon of huANT3. There is, however, no evidence that the extraneous six amino terminal amino acids have any effect on the resultant recombinant huANT3 protein.

In order to confirm expression of the GST-huANT3 fusion protein, the following experiments were carried out. Eight independently isolated pMK3C-GST-huANT3 transformants and one control (vector-transformed) isolate were grown overnight in LB-ampicillin and then diluted 1:20 in 2 ml of fresh media. After 3 hours of growth at 37° C., IPTG was added to a final concentration of 0.1 mM. Cell growth was continued for 2 hours, after which 1.5 of cells were transferred to microfuge tubes, pelleted, resuspended in 300 uL of cold PBS containing 1% Triton X-100, and sonicated twice for 8 seconds. The sonicates were spun for 5 min. at 4° C., the supernatant was transferred to fresh microfuge tubes and 50 uL of glutathione-agarose beads (Sigma) were added to produce a 50% slurry. After a 5 min. incubation at ambient temperature, the beads were spun and washed with 1 ml of PBS three times. The washed pellet was resuspended in SDS spl buffer (62.5 mM Tris, pH 6.8, 2% SDS, 10% glycerol, 5% beta-mercaptoethanol and sufficient bromophenol blue to provide visible coloration), and 30 uL of each preparation (equivalent to 15 uL of culture) was subjected to SDS-PAGE. The gel was stained using a Colloidal Coomassie (G-250) Staining Kit (Novex, San Diego, Calif.). A band of the predicted molecular weight of the GST-huANT3 fusion protein was readily apparent, with the same intensity, in each of the 8 preparations from pMK3C-GST-huANT3 transformants; this band was absent in the control preparation.

B. Western Blot Analysis of Expression of huANT3 Fusion Proteins

E. coli transformed with either (1) pMK3A-huANT3 (the pBAD/His-huANT3 expression construct) or (2) pMK3C-GST-huANT3 (the pGEX/GST-huANT3 expression construct) were lysed by the addition of lysozyme (100 µg/µl; Sigma) for 20 min at room temperature, followed by one freeze/thaw cycle. The negative control for the former transformant was a parallel culture of the transformed cells that had not undergone arabinose induction. The control for the latter transformant was a parallel culture of E. coli that had been transformed with the pGEX-4T-2 vector only.

Total protein concentrations of each lysate were determined using the BCA Protein Assay kit (Pierce Chemical Co.), and equivalent amounts of total protein from each lysate preparation were mixed with equivalent volumes of 2× Laemmli electrophoresis buffer and subjected to SDS-PAGE. The proteins were electrophoretically transferred to nitrocellulose, which was then contacted with antibodies against the appropriate epitope included in each vector (i.e., ANT1-XPRESS™ from Invitrogen for pMK3A-huANT3 and polyclonal goat anti-GST from Amersham Pharmacia Biotech, formerly Nycomed Amersham plc and Pharmacia & UpJohn Inc. for pMK3C-GST-huANT3).

In a separate experiment, the bacterial lysate from the pMK3C-GST-huANT3 transformants was incubated with agarose-glutathione beads (Sigma) according to the manufacturer's instructions (see the preceding section and Smith et al., Expression and Purification of Glutathione S-Transferase Fusion Proteins, Unit 16.7 of Chapter 16 in: *Short Protocols in Molecular Biology*, 2nd Ed., Asubel et al., eds., John Wiley & Sons, New York, N.Y., 1992, pages 16–28 to 16–31). The beads were suspended in Laemmli sample buffer and subjected to SDS-PAGE and Western analysis as described above. Although the yield of GST-huANT3 was low, perhaps because the fusion protein is inserted into the bacterial membrane, a sufficient amount of material was recovered for the experiment.

Figure 5:
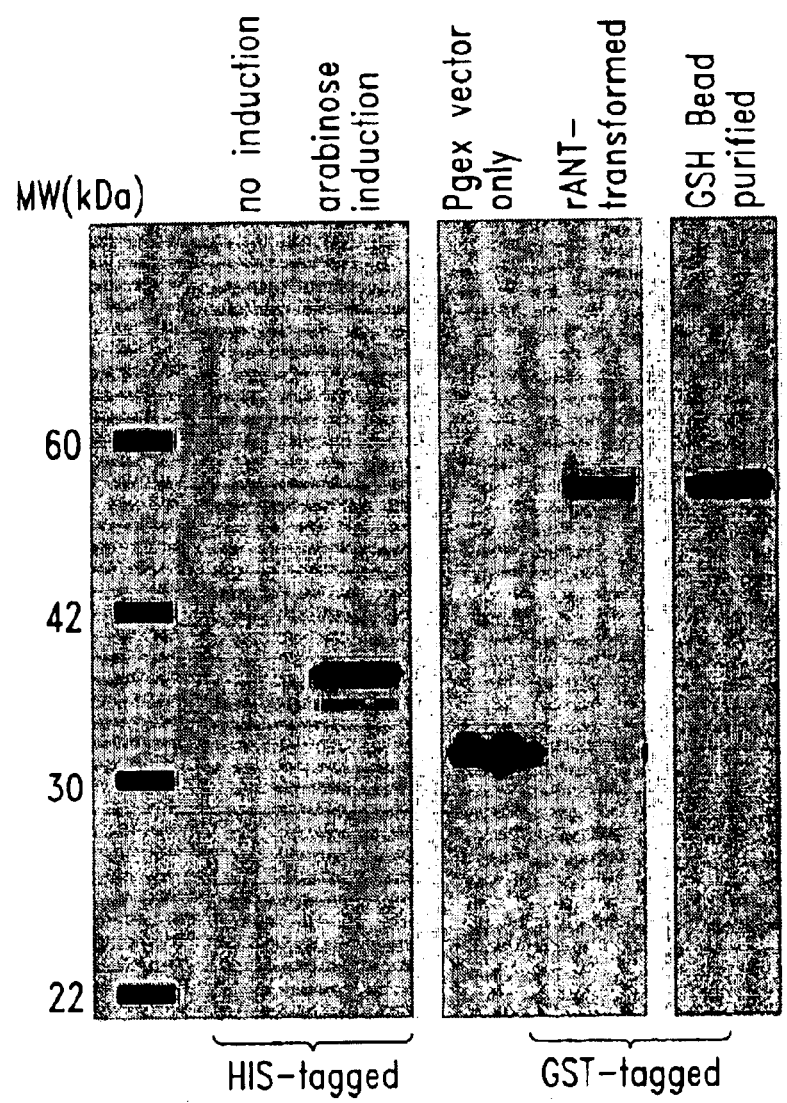
FIG. 5 shows the expression of human ANT3 (huANT3) in *E. coli* expression systems.

The results (FIG. 5) show that a specific band of the predicted molecular weight (His-Tag+enterokinase site+antigenic site+huANT3=38 kilodaltons) was observed in the arabinose induced E.coli that were transformed with the pBAD/his-huANT3 vector, but was absent in the non-induced control culture. Similarly, a band corresponding to GST-huANT3 was observed in the pMK3C-GST-huANT3-transformed E. coli, while only the unaltered GST band was observed in control E. coli transformed with the expression vector. Purification of the GST-huANT3 fusion protein using agarose-GSH beads produced a band of equivalent size to that observed in the crude lysate of pMK3C-GST-huANT-transformed bacteria.

Example 3

Expression of ANT3 in Insect Cells

A. Generation of Baculovirus Expression Constructs

DNA comprising nucleotide sequences encoding huANT3 was amplified by PCR from a whole human brain cDNA library (Clontech) using the following primers. In the following representations of PCR primers, underlined nucleotides indicate sequences complementary to the 5'-ends and 3'-ends of the ANT cDNAs and double-underlined nucleotides indicate recognition sequences for the restriction enzymes BamHI (recognition sequence: 5'-GGATCC) or EcoRI (recognition sequence: 5'-AATTC).

The PCR primers used were:

Forward (sense):

5'-TTATAGGATCC
       ATGACGGAACAGGCCATCTCCTTCGCCAAA,
       and                              SEQ ID NO:16

Reverse (antisense):

5'-TTAAAGAATTC
       TTAGATCACCTFCTTGAGCTCGTCGTACAG
                                      SEQ ID NO:17.

PCR products were digested with the restriction endonucleases BamHI (New England Biolabs) and EcoRI (New England Biolabs) according to the manufacturer's recommendations. Subsequent purification was carried out by horizontal agarose gel electrophoresis and band extraction using the UltraClean™ GelSpin kit (Mo Bio Laboratories, Inc.).

The Baculovirus transfer vector pBlueBacHis2 (B version, Invitrogen) comprises, in 5' to 3' orientation, a constitutive polyhedrin promoter operably linked to nucleotide sequences encoding (1) a translation initiation sequence, (2) an N-terminal polyhistidine sequence ("His tag"), (3) an XPRESS™ epitope tag for detection and purification of the recombinant protein and (4) an enterokinase cleavage site, followed by a multiple cloning site wherein cDNAs can be inserted.

The transfer vector pBlueBacHis2 was prepared by digestion with the restriction endonucleases BamHI and EcoRI according to the manufacturer's recommendation, and the restricted DNA was subject to horizontal agarose gel electrophoresis and band extraction using the UltraClean™ GelSpin kit (Mo Bio Laboratories, Inc.). The restricted PCR products were ligated with the restricted expression vector DNA as in the preceding Examples.

Competent E. coli TOP10F' cells (Invitrogen) were transformed with the ligation reaction following the manufacturer's instructions. Single colonies were selected for growth in 3–5 ml of LB broth containing 50 ug/ml ampicillin. Plasmid DNA was isolated from the bacterial cultures using the WIZARD™Plus Series 9600 Miniprep Reagents System (Promega).

The recombinant ANT gene sequences were determined and their authenticities confirmed (SEQ ID NOS:1, 2 and 3 correspond to human ANTs 1, 2 and 3, respectively) by DNA sequencing using the Prism Ready Dye Terminator Cycle Sequencing Kit (Perkin-Elmer, Catalog #402080) and the following primers: Polyhedrin Forward Sequencing Priming Site, 5'-AAATGATAACCATCTCGC (SEQ ID NO:18); Baculovirus Reverse Sequencing Priming Site, 5'-ACTTCAAGGAGAATTTCC (SEQ ID NO:19); primers internal to the ANT 3 coding sequence (sense strand), 5'-ACTTCGCCTTCACGGATA (SEQ ID NO:20); and 5'-TACGGCCAAGGGCATTCT (SEQ ID NO:21); primers internal to the ANT 3 coding sequence (antisense strand), 5'-TGAAGCGGAAGTTCCTAT (SEQ ID NO:22); and 5'-ATGCCGGTTCCCGTACGA (SEQ ID NO:23). Sequence data were analyzed using the SEQUENCE NAVIGATOR™ analysis software package (Perkin-Elmer). An isolated plasmid having the correct sequence was named pMK4A-huANT3.

Although pMK4A-huANT3 contains authentic huANT3-encoding sequences, the ANT3 reading frame is not synchronous with the reading frame of the His-Tag/XPRESS™ epitope of the expression vector. Accordingly, pMK4A-huANT3 is not expected to produce recombinant ANT protein, although cells harboring it may be used as controls.

In order to generate an in-frame derivative of pMK4A-huANT3, the plasmid was mutagenized using the QUIK-CHANGE™ Site-Directed Mutagenesis Kit (Stratagene) as in Example 1, except that the mutagenic oligonucleotide primers used were 5'-GGCCTGTTCCGTCATCTTATCGTCATCGTCG (SEQ ID NO:24; the underlined sequence is the reverse complement of the 5' end of the huANT3 reading frame), and 5'-CGACGATGACGATAAGATGACGGAACAGGCC (SEQ ID NO:25; the underlined sequence corresponds to the 5' end of the huANT3 reading frame). Several transformants were isolated, and plasmid DNA purified therefrom. The nucleotide sequences of the plasmid DNAs were determined and one having the "correct" sequence was identified and named pMK4B-huANT3.

The baculovirus expression plasmids encoding human ANT3 are referred to as "pMK4A (baculovirus shuttle, out-of-frame hu ANT3) or "pMK4A"; and "pMK4B (baculovirus shuttle, in-frame huANT3)" or "pMK4B". Plasmid pM4B has been deposited at the American Type Culture Collection (ATCC; Manassas, Va.) on Nov. 3, 1998, and given the accession number ATCC 98972.

In order to insert sequences encoding the huANT3 protein (and associated regulatory sequences) into the baculovirus genome, insect cells (MAXBAC™ Spodoptera frugiperda Sf9 cells, Invitrogen, Carlsbad, Calif.; or Trichoplusia ni cells, PharMingen, San Diego, Calif.) were co-transfected with the baculoviral transfer construct pMK4B-huANT3 and linear baculoviral (Autographa californica nuclear polyhedrosis virus, AcMNPV) DNA engineered to contain a promoterless 3' fragment of the lacZ gene (BAC-N-BLUE™, Invitrogen) using the BAC-N-BLUE™ Transfection Kit (Invitrogen) following the manufacturer's instructions. Recombinant baculovirus plaques express functional beta-galactosidase and were identified as blue plaques in the presence of X-gal (5-bromo-4-chloro-3-indoyl-beta-D-glactosidase). These recombinant viruses are expression constructs that express human ANT3 polypeptide in insect cells, as shown by the following experiments.

B. Western Blot Analysis of Baculovirus Expression Systems

High titer viral stock was produced, and recombinant protein was expressed in infected Sf9 (Invitrogen, Carlsbad, Calif.) or T. ni (PharMingen, San Diego, Calif.) cells according to the manufacturer's instructions (see also Piwnica-Worms, Expression of Proteins in Insect Cells Using Baculovirus Vectors, Section II of Chapter 16 in: Short Protocols in Molecular Biology, 2nd Ed., Asubel et al., eds., John Wiley & Sons, New York, N.Y., 1992, pages 16–32 to 16–48; Kitts, Chapter 7 in: Baculovirus Expression Protocols, Methods in Molecular Biology, Vol. 39, C. R. Richardson, Ed., Humana Press, Totawa, N.J., 1995, pages 129–142).

Transfected Sf9 cells were pelleted by centrifugation and lysed by adding 100 μl of MSB buffer (210 mM mannitol (Sigma), 70 mM sucrose (Fluka), 50 mM Tris-HCl, pH 7.4, 10 mM EDTA) and performing three freeze-thaw cycles. A total cellular fraction, a cytosolic fraction, a submitochondrial particle (SMP) fraction, a mitochondrial fraction and a plasma membrane fraction were prepared as follows. The cell lysate was centrifuged at 600 g for 10 minutes at 4° C. to prepare a plasma membrane pellet. The supernatant was removed and set aside. The plasma membrane pellet was washed with 100 ul of MSB, centrifuged at 600 g for 10 minutes at 4° C., and used for the analysis. The supernatant was removed, combined with the first supernatant and mixed. Half of the supernatant was used to prepare a mitochondrial fraction and a cytosolic fraction by centrifugation at 14,000 g for 15 minutes at 4° C.; the pellet represents the mitochondrial fraction and the supernatant represents the cytosol. The other half of the supernatant was centrifuged at 14,000 g for 15 minutes at 4° C. to produce a mitochondria containing pellet that was resuspended in MSB, incubated with 0.25 mg/ml digitonin (Roche Molecular Biochemicals, formerly Boehringer Mannheim, Indianapolis, Ind.) for 2 min and sonicated for 3 min at 50% duty cycle in a cup-horn sonicator to produce submitochondrial particles (SMPs).

The protein content for each fraction was determined using the BCA Protein Assay kit (Pierce Chemical Co.), and 8 ug of total protein were loaded per lane onto an SDS polyacrylamide gel, electrophoresed and transferred to a HYBOND™ ECL Nitrocellulose Membrane (Amersham Life Science). Fusion proteins were detected in a western blot using ANTI-XPRESS™ Antibody (Invitrogen, Catalog #R910-25) and horseradish peroxidase-conjugated anti-mouse secondary antibody (Amersham Life Science) following the manufacturers' instructions.

Figure 6:
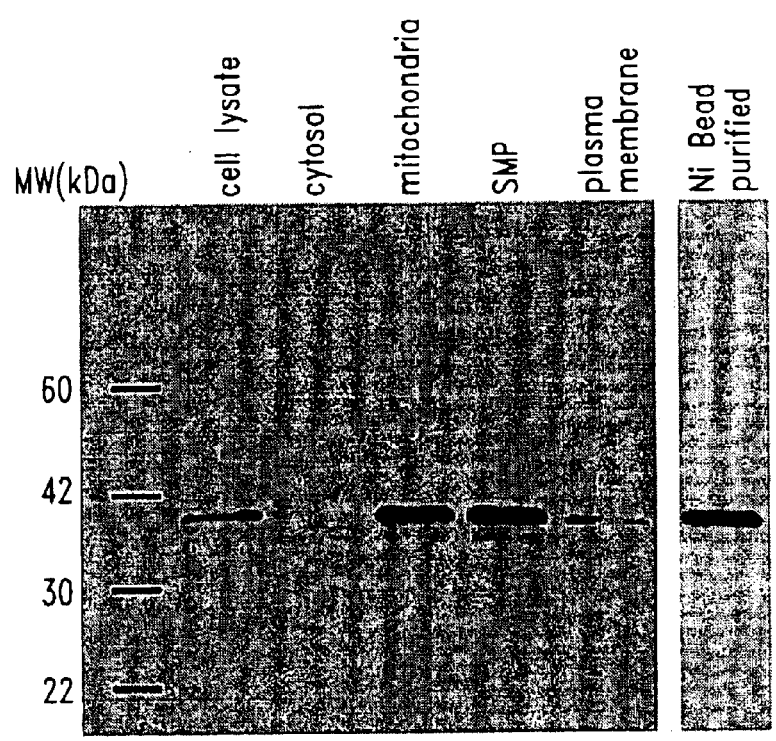
FIG. 6 shows the expression of huANT3 in baculovirus-infected Sf9 cells.

The results of the Western analysis are shown in FIG. 6. Recombinant GST-huANT3 fusion protein (molecular weight 36.6 kD) was detected in total cells, mitochondria, submitochondrial particles and the plasma membrane. The signal was most intense in mitochondria and submitochondrial particles, whereas no band was detectable in the cytosolic fraction. These data suggest that the human recombinant huANT3 fusion protein integrated into the mitochondrial membranes much more efficiently than into the plasma membranes. Furthermore, all of the recombinant protein integrated into membranes since no signal was detected in the cytosolic fraction. The final lane of the autoradiogram shows His-tagged huANT3 isolated from cell lysates using magnetic agarose beads coupled to Ni according to the manufacturers instructions (Qiagen; Hilden, Germany).

Thus, as in *E. coli,* huANT3 is expressed in the baculovirus/Sf9 system. Furthermore, recombinantly produced 6xHis- and epitope-tagged huANT3 fusion protein is appropriately localized to the mitochondria in Sf9 cells despite the presence of over 35 extraneous N-terminal amino acids, and can be isolated from cellular fractions by means that take advantage of the His-Tag moiety's affinity for metals such as, e.g., nickel.

Example 4

Expression of ANT3 in Yeast

A. Expression Constructs and Host Cells

Human ANT3 cDNA was amplified by PCR as in Example 1 but using the following primers. In the following representations of PCR primers, underlined nucleotides indicate sequences complementary to the 5'-ends and 3'-ends of the ANT cDNAs and double-underlined nucleotides indicate recognition sequences for the restriction enzymes XhoI (recognition sequence: 5'-CTCGAG) or Asp718 (recognition sequence. 5'-GGTACC).

The primers used for PCR amplification were:
Forward (sense):

5'-TTAATGGGTACC
ATGACGGAACAGGCCATCTCCTTCGCCAAA,
and                                    SEQ ID NO:28

Reverse (antisense):

5'-TTATACTCGAG
TTAGATCACCTTCTTGAGCTCGTCGTACAGG
                                       SEQ ID NO:29.

PCR products, and expression vector DNAs, were digested with the restriction endonucleases XhoI and Asp718 both enzymes from Roche Molecular Biochemicals) according to the manufacturer's recommendations using manufacturer-supplied reaction buffers. The expression vector pYES2 (Invitrogen) was used. This vector contains a multiple cloning site located immediately downstream from an inducible GAL1 promoter, as well as the 2u origin of replication and the *S. cerevisiae* URA3 gene for high-copy maintenance and selection in ura3 yeast cells, respectively.

The restricted DNAs were purified by horizontal agarose gel electrophoresis and band extraction using the UltraClean GelSpin kit (Mo Bio Laboratories), ligated to each other, and used to transform *E. coli* cells, as in the preceding Examples. Plasmid DNA was isolated from several transformants, and the nucleotide sequence of the insert DNA was determined and confirmed to be that of huANT3. One confirmed plasmid was chosen to be used for further study and was designated pMK5A (huANT3).

A second yeast huANT3 expression vector, pMK5B, was constructed as follows. Plasmids pMK5A and pYESTrp2 (Invitrogen) were digested with restriction enzymes BglI and PvuII (both from New England Biolabs) and gel purified, ligated and used to transform *E. coli* as above. The expression vector pYES2Trp is similar to pYES2 but comprises a TRP1 selectable marker. Plasmid DNA was isolated from several transformants and restriction mapped to confirm the structure of the expected expression construct. One confirmed plasmid was chosen to be used for further study and was designated pMK5B (huANT3).

A third yeast huANT3 expression vector, pMK5C, was constructed using the expression vector pYPGE2, which comprises a TRP1 selectable marker and the strong PGK promoter upstream from a multiple cloning site (Brunelli and Pall, 1993 *Yeast* 9:1299–1308). Plasmid pYPGE2 DNA was digested with XhoI and Asp718, gel-purified and ligated with the XhoI- and Asp718-restricted huANT3 PCR product of Example 1. The ligation mixture was used to transform *E. coli,* and plasmid DNA was isolated from several transformants and restriction mapped to confirm the structure of the expected expression construct. One confirmed plasmid was chosen to be used for further study and was designated pMK5C (huANT3).

In order to generate yeast expression systems, the *S. cerevisiae* strain INVSc1 (MATα, his3Δ1, leu2, trp1-289, ura3-52) was transformed with purified pMK5A, pMK5B and pMK5C DNAs using the S.c. EASYCOMP™ Transformation Kit (Invitrogen). A second *S. cerevisiae* strain, JΔ1Δ3 (MATα, ade2-1, leu2-3, leu2-112, his3-11, his3-15, trp1-1, ura3-1, can1-100, AAC1::LEU2, AAC2::HIS3, AAC3::URA3) was also transformed with the expression constructs. The AAC genes encode the three isoforms of the mitochondrial ADP/ATP translocator in *S. cerevisiae* and are interrupted in strain JΔ1Δ3 (Giraud et al., *J. Mol. Biol.* 281:409–418 (1998)). It is thus expected that transformants of JΔ1Δ3, which are incapable of expressing endogenous ANT (AAC) proteins, will only express the human ANT protein encoded by the expression construct with which they have been transformed.

B. Northern Blot Analyses of Yeast Expression Systems

In order to examine levels of huANT3 mRNA production in strain JΔ1Δ3, Northern analyses of cells transformed with pMK5B and pMK5C were performed according to methods known in the art. In brief, transformed cells and control (untransformed) cells grown to mid-log phase, harvested and lysed. RNA was extracted from the lysates, electrophoresed and transferred to a nitrocellulose filter (see Treco, Preparation of Yeast RNA, Unit 13.12 of Chapter 13 in *Short Protocols in Molecular Biology,* 2nd Ed., Asubel et al., eds., John Wiley & Sons, New York, N.Y. (1992), 13:44–46 and Seldon, Analysis of RNA by Northern Hybridization, Unit 4.9 of Chapter 4, Id., 4:23–25). The XhoI- and Asp718-restricted huANT3 PCR product of Example 1 was radiolabelled and used as a probe, and an RNA preparation from human spleen tissue was used as a positive control.

Figure 10:
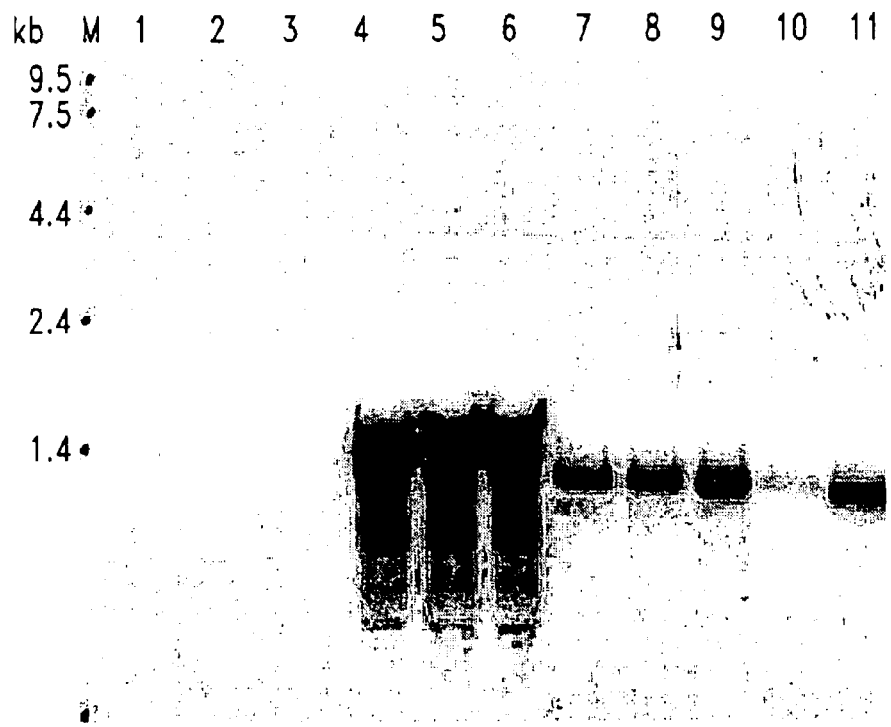
FIG. 10 shows Northern blot analysis of huANT3 transcripts detected in yeast expression systems. Lane contents: lane "M," molecular weight markers (positions of 1.4, 2.4, 4.4, 7.5 and 9.5 kilobase markers indicated); lanes 1–3, 10 ug of RNA from three independent isolates of mock transformed AAC⁻ yeast; lanes 4–6, 10 ug of RNA from three independent isolates of AAC⁻ yeast transformed with pMK5C (pYPGE2-buANT3); lanes 7–9, 10 ug of RNA from three independent isolates of AAC⁻ yeast transformed with pMK5B (pYESTrp2-huANT3); lanes 10 and 11, 0.2 (lane 10) and 0.8 (lane 11) ug of RNA prepared from samples of human spleen.

The results (FIG. 10) demonstrate the appropriately-sized ANT3-specific RNA is produced in human spleen and in yeast cells transformed with either expression vector, but not in untransformed yeast cells. The pYPGE2-derived expression construct pMK5C, which directs ANT3 expression from the PGK promoter, clearly results in more ANT3 RNA than the pYES2Trp-derived construct pMK5B, in which ANT3 expression is driven by the GAL1 promoter. In either case, however, significant levels of huANT3-specific RNA were produced in a yeast background that lacks any endogenous adenosine nucleotide translocator proteins.

Example 5

Expression of ANT3 in Mammalian Cells

The preceding Examples describe a variety of means by which ANT and ANT fusion proteins can be recombinantly produced in various systems. Although such ANT proteins can be used in a variety of assays (see infra), it may be desirable to isolate large amounts of the native ANT protein from mammalian cells. In particular, as described in this Example, it may be desirable to produce recombinant viral particles in which ANT proteins are displayed in the viral envelope. Such ANT-displaying viral particles are expected to be very stable and useful in a variety of assays including, for example, those in which compounds binding to ANT proteins are screened and identified.

Another useful outcome of mammalian expression systems is the generation and isolation of human mitochondria in which a particular ANT isoform is over-represented in order to determine the specific biological role(s) of such isoforms. For example, ANT3 is apparently ubiquitously expressed in human tissues, whereas ANT1 is primarily expressed in heart and skeletal muscle (Stepien et al., 1992, *J. Biol. Chem.* 267:14592–14597). Directed overexpression of huANT1 in cultured heart or muscle cells is expected to result in mitochondria that contain mostly the ANT1 isoform. Such "ANT isoform-enriched" mitochondria can be isolated and tested for various mitochondrial functions.

Constructs for expressing ANT proteins in mammalian cells are prepared in a stepwise process. First, expression cassettes that comprise a promoter (and associated regulatory sequences) operably linked to nucleotide sequences encoding an ANT protein are constructed in bacterial plasmid-based systems; these expression cassette-comprising constructs are evaluated and optimized for their ANT-producing ability in mammalian cells that are transiently transfected therewith. Second, the ANT expression cassettes are transferred to viral systems that produce recombinant proteins during lytic growth of the virus (e.g., SV40, BPV, EBV, adenovirus; see below) or from a virus that can stably integrate into and transduce a mammalian cellular genome (e.g., a retroviral expression construct).

A. Transient Expression

With regards to the first step, commercially available "shuttle" (i.e., capable of replication in both *E. coli* and mammalian cells) vectors that comprise promoters that function in mammalian cells and can be operably linked to an ANT-encoding sequence include, but are not limited to, SV40 late promoter expression vectors (e.g., pSVL, Pharmacia), glucocorticoid-inducible promoter expression vectors (e.g., pMSG, Pharmacia), Rous sarcoma enhancer-promoter expression vectors (e.g., pRc/RSV, Invitrogen) and CMV early promoter expression vectors, including derivatives thereof having selectable markers to agents such as Neomycin, Hygromycin or ZEOCIN™ (e.g, pRc/CMV2, pCDM8, pcDNA1.1, pcDNA1.1/Amp, pcDNA3.1, pcDNA3.1/Zeo and pcDNA3.1/Hygro, Invitrogen) In general, preferred shuttle vectors for ANT genes are those having selectable markers (for ease of isolation and maintenance of transformed cells) and inducible, and thus regulatable, promoters (as overexpression of ANT genes may have toxic effects).

Methods for transfecting mammalian cells are known in the art (see, Kingston et al., "Transfection of DNA into Eukaryotic Cells," Section I of Chapter 9 in: *Short Protocols in Molecular Biology*, 2nd Ed., Asubel et al., eds., John Wiley & Sons, New York, N.Y., 1992, pages 9-3 to 9-16). A control plasmid, such as pCH110 (Pharmacia), may be cotransfected with the ANT expression construct being examined so that levels of ANT can be normalized to a gene product expressed from the control plasmid.

Western analyses of mammalian expression systems are performed essentially as described in the preceding Examples, except that different methods are used to prepare protein preparations from mammalian cells as opposed to bacterial, insect or yeast cells. Such methods of isolating proteins from yeast are known in the art (see, for example, Kingston and Sheen, Unit 9.6A and Brasier, Unit 9.6B of Chapter 9 in: *Short Protocols in Molecular Biology*, 2nd Ed., Asubel et al., eds., John Wiley & Sons, New York, N.Y., 1992, pages 9-17 to 9-23). Preferred expression cassettes, consisting essentially of a promoter and associated regulatory sequences operably linked to an ANT gene of interest, are identified by the ability of cells transiently transformed with a vector comprising a given ANT expression cassette to express high levels of ANT protein when induced to do so; these expression cassettes are incorporated into viral expression vectors.

B. Viral Expression

Nucleic acids, preferably DNA, comprising preferred expression cassettes are isolated from the transient expression constructs in which they were prepared, characterized and optimized (see preceding section). A preferred method of isolating such expression cassettes is by amplification by PCR, although other methods (e.g., digestion with appropriate restriction enzymes) can be used. Preferred expression cassettes are introduced into viral expression vectors, preferably retroviral expression vectors, in the following manner.

A DNA molecule comprising a preferred expression cassette is introduced into a retroviral transfer vector by ligation (see preceding Examples). Two types of retroviral transfer vectors are known in the art: replication-incompetent and replication-competent. Replication-incompetent vectors lack viral genes necessary to produce infectious particles but retain cis-acting viral sequences necessary for viral transmission. Such cis-acting sequences include the Ψ packaging sequence, signals for reverse transcription and integration, and viral promoter, enhancer, polyadenylation and other regulatory sequences. Replication-competent vectors retain all these elements as well as genes encoding virion structural proteins (typically, those encoded by genes designated gag, pol and env) and can thus form infectious particles in a variety of cell lines. In contrast, these functions are supplied in trans to replication-incompetent vectors in a packaging cell line, i.e, a cell line that produces mRNAs encoding gag, pol and env genes but lacking the Ψ packaging sequence. See, generally, Cepko, Unit 9.10 of Chapter 9 in: *Short Protocols in Molecular Biology*, 2nd Ed., Asubel et al., eds., John Wiley & Sons, New York, N.Y., 1992, pages 9-30 to 9-35.

A retroviral construct comprising an ANT expression cassette produces RNA molecules comprising the cassette sequences and the Ψ packaging sequence. These RNA molecules correspond to viral genomes that arc encapsidated by viral structural proteins in an appropriate cell line (by "appropriate" it is meant that, for example, a packaging cell line must be used for constructs based on replication-incompetent retroviral vectors). Infectious viral particles are then produced, and released into the culture supernatant, by budding from the cellular membrane. The infectious particles, which comprise a viral RNA genome that includes the ANT expression cassette, are prepared and concentrated according to known methods. It may be desirable to monitor undesirable helper virus, i.e., viral particles which do not comprise an ANT expression cassette. See, generally, Cepko, Units 9.11, 9.12 and 9.13 of Chapter 9 in: *Short Protocols in Molecular Biology*, 2nd Ed., Asubel et al., eds., John Wiley & Sons, New York, N.Y., 1992, pages 9-36 to 9-45.

Viral particles comprising an ANT expression cassette are used to infect in vitro (e.g., cultured cells) or in vivo (e.g., cells of a rodent, or of an avian species, which are part of a whole animal). Tissue explants or cultured embryos may also be infected according to methods known in the art. See, generally, Cepko, Unit 9.14 of Chapter 9 in: *Short Protocols in Molecular Biology,* 2nd Ed., Asubel et al., eds., John Wiley & Sons, New York, N.Y., 1992, pages 9-45 to 9-48. Regardless of the type of cell used, production of ANT protein is directed by the recombinant viral genome.

In a preferred embodiment, recombinantly produced ANT proteins are inserted into the cell membrane of cultured cells. Because the retroviral expression construct produces viral particles by budding of the cell membrane, the resultant viral particles delivered to the culture supernatant have ANT protein incorporated into their capsules, preferably on the surface of the particles. Such ANT-displaying viral particles are expected to provide a stable format for ANT proteins and to thus be useful in assays using ANT proteins, either directly or as a source material from which ANT can be further purified. If it is desired to minimize the amount of ANT protein inserted into mitochondrial membranes, $\rho^0$ cells, which have been treated in such a manner as to be nearly or completely devoid of mitochondria, are used as host cells.

C. Preparation and Expression of pCDNA-ANT3 Expression Constructs

ANT3 cDNA was amplified by polymerase chain reactions (PCR) in a thermal cycler using the following primers, AMPLITAQ™ DNA Polymerase (Perkin-Elmer), and reagents and buffers supplied in a GENEAMP™ PCR Reagent Kit (Perkin-Elmer), according to the manufacturer's instructions. In the following representations of the PCR primers, underlined nucleotides indicate sequences complementary to the 5'-ends and 3'-ends of the ANT3 cDNAs, double-underlined nucleotides indicate recognition sequences for the restriction enzymes XhoI (recognition sequence: 5'-CTCGAG) and Asp718 (recognition sequence 5'-GGTACC), and the ANT3 start codon (ATC) and the reverse complement of the stop codon (TAA) are emboldened.

The primers used to amplify human ANT3 (huANT3; SEQ ID NO:3) from an ANT3 expression construct (pMK3A-huANT3, a.k.a. pBAD/His-ANT3) were:

Forward (sense):

5'-TTAATGGTACC
ATGACGGAACAGGCCATCTCCTTCGCCAAA,
and                                SEQ ID NO:31

Reverse (antisense):

5'-TTATACTCGAG
TTAGATCACCTTCTTGAGCTCGTCGTACAGG
                                   SEQ ID NO:32.

PCR products were digested with the restriction endonucleases XhoI and Asp718 (both enzymes from Roche Molecular Biochemicals) according to the manufacturer's recommendations using manufacturer-supplied reaction buffers. Restricted DNAs were purified by horizontal agarose gel electrophoresis and band extraction using the Ultra-Clean™ GelSpin kit (Mo Bio Laboratories, Inc., Solana Beach, Calif.).

The expression vector pcDNA3 (Invitrogen, Carlsbad, Calif.) was used. This vector contains the following elements operably linked in a 5' to 3' orientation: the cytomegalovirus (CMV) enhancer/promoter ($P_{CMV}$); a multiple cloning site (MCS) containing recognition sequences for several restriction enzymes; and the bovine growth hormone (BGH) polyadenylation signal and transcription termination sequence to enhance mRNA stability. The expression vector also contains an ampicillin resistance gene for positive selection of transformants in prokaryotes (e.g., *E. coli*), as well as a neomycin resistance gene for positive selection of transformants in mammalian cells, and origins of replication for bacterial and mammalian cells (ColE1- and SV40-derived, respectively). The SV40 origin of replication allows for episomal replication of the expression construct as well as simple vector rescue in cells expressing the large T antigen of SV40 (i.e., COS-1 or COS-7 cells, ATCC accession numbers CRL-1650 and CRL-1651, respectively).

Plasmid pcDNA3 was prepared by digestion with the restriction endonucleases XhoI and Asp718 according to the manufacturer's instructions and subjected to horizontal agarose gel electrophoresis and band extraction using the Ultra-Clean™ GelSpin kit (Mo Bio Laboratories). Restriction enzyme digested ANT cDNAs were ligated into the similarly-digested pcDNA3 expression vector DNA using T4 DNA ligase (New England Biolabs, Beverly, Mass.) using the manufacturer's reaction buffer and following the manufacturer's instructions. Competent *E. coli* cells (strain DH5α; Life Technologies, Inc. {Gibco BRL}, Gaithersburg, Md.) were transformed with ligation mixtures according to the manufacturer's instructions. Single colonies were selected and grown in 3–5 ml of LB broth (Sambrook, J., Fritsch, E. F., and Maniatis, T., *Molecular Cloning: A Laboratory Manual,* Cold Spring Harbor Laboratory Press, Cold Spring Harbor, N.Y., 1989) containing 50 µg/ml ampicillin (Roche Molecular Biochemicals). Plasmid DNA was isolated from the bacterial cultures using the WIZARD™ Plus Series 9600 Miniprep Reagents System (Promega, Madison, Wis.). Several isolates of pcDNA3-derived ANT3 expression constructs were restriction mapped to confirm their structures. One isolate of a pcDNA3-ANT3 expression construct having the predicted restriction map was selected for further experiments and designated "pMK6-ANT3."

Example 6

Cloning and Expression of ANT-Green Fluorescent Protein (ANT-GFP) Fusion Proteins In this Example, the preparation and structures of two different ANT-GFP fusion protein expression constructs are described. Green fluorescent protein (GFP) is a naturally-occurring fluorescent protein that has been extensively genetically engineered in order to produce GFP derivatives having shifted emission spectra and/or the capacity to fluoresce more intensely than the native protein (for a review of GFP, see Kendall et al., *Trends in Biotechnology* 16:216–224, 1998, and references cited therein; for a treatise on GFP, see Chalfie, M., and Kain, S., eds., *Green Fluorescent Protein: Properties, Applications, and Protocols,* John Wiley & Sons, Inc., New York, 1998, and references cited therein). As used herein, the term "green fluorescent protein" encompasses the wildtype green fluorescent protein (wildtype GFP), as well as blue-shifted, cyan-shifted, red-shifted and yellow-shifted derivatives of wildtype GFP (designated, respectively, BFP, CFP, RFP and YFP; see published PCT application WO 98/06737), as well as other GFP derivatives comprising additional functional polypeptide sequences.

A. Preparation of Amino Terminal Fusion (EYFP-ANT) Protein

As described in detail in Example 2, pMK3C-GST-huANT3 (also referred to herein as pMK3C) is an expression construct derived from pGEX-4T-2 that comprises sequences encoding, and directs the expression of, a GST-huANT3 fusion protein (GST, glutathione S-transferase). Plasmid pMK3C was digested with the restriction enzymes BamHI and XhoI in order to liberate a restriction fragment that contains the ANT3-coding sequences but which lacks sequences encoding GST or the thrombin cleavage site that links GST to ANT3 in pMK3C.

The expression vector pEYFP-C1 (Clontech Laboratories, Inc., Palo Alto, Calif.) was restriction enzyme digested with BglII and SalI. Although BglII (in the pEYFP-C1 vector) and BamHI (in the ANT3 fragment) do not have identical recognition sequences, these restriction enzymes generate compatible sticky ends having the sequence 5'-GATC. Similarly, although SalI (in the pEYFP-C1 vector) and XhoI (in the ANT3 fragment) do not have identical recognition sequences, these restriction enzymes generate compatible sticky ends having the sequence 5'-TCGA. In the desired ligation product formed from the preceding restriction fragments, the BglII site in pEYFP-C1 is linked to the BamHI site in the ANT3-encoding fragment, and the XhoI site in the ANT3-encoding fragment is linked to the SalI site in pEYFP-C1, and the resultant plasmid encodes a YFP-ANT3 fusion protein. The term "EYFP-ANT3 fusion protein" indicates a single contiguous polypeptide chain that has (1) an amino terminal polypeptide portion corresponding to enhanced yellow fluorescent protein (EYFP), having an excitation maximum at 513 nm and a peak emission at 527 nm, and (2) a carboxy terminal polypeptide portion corresponding to huANT3.

The restriction enzyme digested DNAs were ligated to one another using T4 DNA ligase under standard conditions known in the art. Competent recA1 hsdR endA1 *E. coli* cells (strain TOP10F'; Invitrogen, Carlsbad, Calif.) were transformed with the ligation mixtures according to the manufacturer's instructions. Single colonies were selected and grown in 3–5 ml of LB broth, and plasmid DNA was isolated from the bacterial cultures using the WIZARD™ Plus Series 9600 Miniprep Reagents System (Promega, Madison, Wis.) and restriction mapped. One isolate of a EYFP-ANT3 expression construct having the predicted restriction map was selected for further experiments and designated "pMK7-EYFP(N)-ANT3."

B. Preparation of Carboxy Terminal Fusion (ANT-EYFP) Protein

Plasmid pcDNA3-huANT3 (pMK6ANT3) was restriction enzyme digested with XhoI (at the 3' end of the huANT3 insert) and XbaI (3' from the XhoI site in the MCS). An in-frame XhoI-XbaI restriction fragment containing sequences encoding EYFP was prepared as follows. DNA was amplified by PCR in a thermal cycler using the following primers, plasmid pEYFP-C1 as a substrate, AMPLITAQ™ DNA Polymerase (Perkin-Elmer, Foster City, Calif.), and reagents and buffers supplied in a GENEAMP™ PCR Reagent Kit (Perkin-Elmer), according to the manufacturer's instructions. In the following representations of the PCR primers, singly underlined nucleotides indicate sequences complementary to the 5'-ends and 3'-ends of the EYFP-encoding DNA, double-underlined nucleotides indicate recognition sequences for the restriction enzymes XhoI (recognition sequence: 5'-CTCGAG) and XbaI (recognition sequence: 5'-TCTAGA), and the EYFP start codon (ATG) and the reverse complement of the YFP stop codon (TAG) are emboldened.

The primers used had the nucleotide sequences:

Forward (sense):

5'-GGGCCCCTCGAGATGGTGAGCAAGGGCGAG, and                                     SEQ ID NO:33

Reverse (antisense):

5'-GGGCCCTCTAGACTACTTGTACAGCTCGTCCAT

SEQ ID NO:34.

The restriction enzyme digested PCR and plasmid DNAs were purified by horizontal agarose gel electrophoresis and band extraction using the UltraClean™ GelSpin kit (Mo Bio Laboratories). The purified DNAs were ligated together using T4 DNA ligase and used to transform competent *E. coli* cells (strain DH5α; Life Technologies Inc., Gaithersburg, Md.) according to the manufacturer's instructions. Single colonies were selected and grown in 3–5 ml of LB broth containing 50 µg/ml ampicillin. Plasmid DNA was isolated from the bacterial cultures as in the preceding Examples and restriction mapped. One isolate of an ANT3-YFP expression construct having the predicted restriction map was selected for further experiments and designated "pMK8-ANT3-EYFP(C)." The nucleotide sequence of the ANT3-YFP encoding region in pMK8-ANT3-EYFP(C) was confirmed using standard methods. Due to the structure of pMK8-ANT3-EYFP(C), the expression construct directs the production of a protein that has (1) an amino terminal huANT3 polypeptide and (2) a carboxy terminal enhanced yellow fluorescent protein (EYFP) having an excitation maximum at 513 nm and a peak emission at 527 nm.

C. Expression and Intracellular Localization of ANT3-EYFP Fusion Proteins

The expression and intracellular localization of the two ANT-GFP fusion proteins described in the immediately preceding section was examined in several ways. First, fluorescent microscopy was used to visualize 293 cells transformed with either pMK7-EYFP(N)-ANT3 or pMK8-ANT3-EYFP(C). In the case of pMK7-EYFP(N)-ANT3, the observed immunofluorescence was diffuse and spread throughout the cytosol. In contrast, the immunofluorescence seen in cells transformed with pMK8-ANT3-EYFP(C) to be confined to mitochondria. Similar results were seen with other cell types, i.e., COS-1 and SH-SY5Y, transformed with the ANT3-GFP expression constructs.

In order to further examine the mitochondrial localization of the ANT3-EYFP fusion proteins, Western analysis of subcellular fractions was carried out as follows. Transfected 293 cells were pelleted by centrifugation and lysed by adding 100 µl of MSB buffer (210 mM mannitol (Sigma), 70 mM sucrose (Fluka), 50 mM Tris-HCl, pH 7.4, 10 mM EDTA) and performing three freeze-thaw cycles. A total cellular fraction, a cytosolic fraction, a submitochondrial particle fraction, a mitochondrial fraction and a plasma membrane fraction were prepared as follows. The cell lysate was centrifuged at 600 g for 10 minutes at 4° C. to prepare a plasma membrane pellet. The supernatant was removed and set aside. The plasma membrane pellet was washed with 100 ul of MSB, centrifuged at 600 g for 10 minutes at 4° C., and used for the analysis. The supernatant was removed, combined with the first supernatant and mixed, and was used to prepare a mitochondrial fraction and a cytosolic fraction by centrifugation at 12,000–14,000 g for 15 minutes at 4° C.; the pellet represents the mitochondrial fraction and the supernatant represents the cytosol.

The protein content for each fraction was determined using the BCA Protein Assay kit (Pierce Chemical Co., Rockford, Ill.), and an equivalent amount (10 ug) of total protein was loaded per lane onto an SDS polyacrylamide gel, electrophoresed and transferred to a HYBOND™ ECL Nitrocellulose Membrane (Amersham Life Science, Arlington Heights, Ill.). The ANT3-EYFP fusion proteins were detected in a western blot using an antibody that recognizes all GFP derivatives and is detectably labeled via conjugation to horseradish peroxidase (the Living Colors® peptide antibody, Clontech, Palo Alto, Calif.) essentially according to the manufacturer's instructions. The results of the Western analysis confirm that the protein expressed from pMK8-ANT3-EYFP(C), in which the YFP-encoding sequences are on the carboxy terminal side of the ANT3-GFP fusion protein, localizes exclusively to mitochondria.

Example 7
Cloning and Expression of His-Tagged Cyclophilin A (His6x-CypA) Fusion Proteins in Bacteria Unlike cyclophilin D (CypD), which interacts with ANT (Woodfield et al., *Biochem J.* 336:287–290, 1998), the structurally related protein cyclophilin A (CypA) does not appear to interact with ANT, at least under normal physiological conditions. CypA was thus prepared as a specificity control for assays of agents that affect CypD:ANT interactions. In order to produce large quantities of CypA proteins, including CypA fusion proteins, recombinant DNA techniques were used.

A. PCR Amplification of CypA cDNAs

A cDNA library derived from total cellular RNA prepared from human placenta was obtained from a commercial source (Clontech, Palo Alto, Calif.). The RNA was purified by treatment with RNase-free DNase I (Roche Molecular Biochemicals, formerly Boehringer Mannheim Biochemicals, Indianapolis, Ind.) using 1 ul of DNase I (10 u/ul) in a buffer containing 40 mM Trsi-HCl, pH 7.0, 6 mM magnesium chloride and 2 mM calcium chloride for 30 minutes at 37° C. This treatment was followed by two phenol/chloroform extractions, one chloroform extraction and an ethanol precipitation in the presence of sodium acetate. The RNA pellet was collected by centrifugation, washed with 70% ethanol, air dried, and resuspended in RNase-free sterile water. The RNA was reverse transcribed to generate cDNA using RNase H-deficient Reverse Transcriptase (SUPERSCRIPT™; Life Technologies, Rockville, Md.).

CypA cDNAs were amplified by polymerase chain reactions (PCR) in a thermal cycler using the following primers, AMPLITAQ™ DNA Polymerase (Perkin-Elmer), and reagents and buffers supplied in a GENEAMP™ PCR Reagent Kit (Perkin-Elmer), according to the manufacturer's instructions. In the following representations of the PCR primers, underlined nucleotides indicate sequences complementary to the 5'-ends and 3'-ends of the CypA cDNAs, double-underlined nucleotides indicate recognition sequences for the restriction enzymes XhoI (recognition sequence: 5'-CTCGAG) and Asp718 (recognition sequence: 5'-GGTACC), and the huCypA start codon (ATG) and the reverse complement of the stop codon (TAA) are emboldened.

For human CypA (huCypA; SEQ ID NO:26), primers having the following nucleotide sequence were used:
Forward (sense):

5'-TTTAAACTCGAGTATGGTCAACCCCACCGTGTTC,
and                                               SEQ ID NO:35

Reverse (antisense):

5'-TATATAGGTACCTTATCGAGTTGTCCACAGTCAG
                                              SEQ ID NO:36.

B. Generation of 6xHisCypA Expression Constructs

The expression vector pBAD/His ("B" derivative; Invitrogen) was used. This vector contains the following elements operably linked in a 5' to 3' orientation: the inducible, but tightly regulatable, araBAD promoter; optimized *E. coli* translation initiation signals; an amino terminal polyhistidine (6xHis)-encoding sequence (also referred to as a "His-Tag"); an XPRESS™ epitope-encoding sequence; an enterokinase cleavage site which can be used to remove the preceding N-terminal amino acids following protein purification, if so desired; a multiple cloning site; and an in-frame termination codon.

Plasmid pBAD/His DNA was prepared by digestion with the restriction endonucleases XhoI and Asp718 according to the manufacturer's instructions and subjected to horizontal agarose gel electrophoresis and band extraction using the UltraClean GelSpin kit (Mo Bio Laboratories). Restriction enzyme digested CypA cDNA was ligated with restricted expression vector DNA using T4 DNA ligase (New England Biolabs, Beverly, Mass.) using the manufacturer's reaction buffer and following the manufacturer's instructions. Competent *E. coli* cells (strain TOP10F'; Invitrogen) were transformed with ligation mixtures containing the prokaryotic vector construct according to the manufacturer's instructions. Single colonies were selected and grown in 3–5 ml of LB broth, and plasmid DNA was isolated from the bacterial cultures using the WIZARD™ Plus Series 9600 Miniprep Reagents System (Promega). One isolate of a 6xHis-huCypA expression construct having the predicted restriction map (based on the nucleotide sequences of the expression vector and human CypA, see FIG. 7, SEQ ID NO:26) was selected for further experiments and designated "pMK9-6xHis-huCypA."

Example 8
Cloning and Expression of Glutathione S-Transferase-Cyclophilin A (GST-CypA) Fusion Proteins in Bacteria A. PCR Amplification of CypA cDNAs CypA cDNA was amplified from pMK9-6xHis-huCypA by PCR in a thermal cycler using the following primers, AMPLITAQ™ DNA Polymerase (Perkin-Elmer), and reagents and buffers supplied in a GENEAMP™ PCR Reagent Kit (Perkin-Elmer), according to the manufacturer's instructions. In the following representations of the PCR primers, underlined nucleotides indicate sequences complementary to the 5'-ends and 3'-ends of the CypA cDNAs, double-underlined nucleotides indicate recognition sequences for the restriction enzymes XhoI (recognition sequence: 5'-CTCGAG) and BamHI (recognition sequence: 5'-GGATCC), and the huCypA start codon (ATG) and the reverse complement of the stop codon (TAA) are emboldened.

For huCypA, the following primers were used:
Forward (sense):

5'-TTAAGGATCCATGGTCAACCCCACCGTGTTC,
and                                               SEQ ID NO:37

Reverse (antisense):

5'-ATATCTCGAGTTATTCCAGTTGTCCACAGTCAG
                                              SEQ ID NO:38.

B. Generation of GST-CypA Expression Constructs

The CypA PCR products were digested with the restriction endonucleases XhoI and BamHI (both enzymes from Roche Molecular Biochemicals) according to the manufacturer's recommendations using manufacturer-supplied reaction buffers. Restricted DNAs were purified by horizontal agarose gel electrophoresis and band extraction using the UltraClean™ GelSpin kit (Mo Bio Laboratories, Inc.).

The expression vector pGEX-4T-2 (Amersham Pharmacia Biotech) was used to generate huCypA fusion proteins comprising an enzymatic polypeptide and an CypA polypeptide. This vector comprises a lacI$^q$ (repressor) gene a fac promoter operably linked to a glutathione S-transferase (GST) gene from *Schistosoma japonicum.* (Smith et al., 1988, *Gene* 67:31–40), the coding sequence of which has been modified to comprise a thrombin cleavage site-encoding nucleotide sequence immediately 5' from a multiple cloning site. GST fusion proteins can be detected by Western blots with anti-GST or by using a colorimetric assay; the latter assay utilizes glutathione and 1-chloro-2-4-dinitrobenzene (CDNB) as substrates for GST and yields a yellow product detectable at 340 nm (Habig et al., 1974, *J. Biol. Chem* 249:7130–7139). GST fusion proteins produced from expression constructs derived from this expression vector can be purified by, e.g., glutathione affinity chromatography, and the desired polypeptide released from the fusion product by thrombin. Thus, this expression vector provides for the rapid purification of fusion proteins, and release of proteins with relatively few extraneous N-terminal amino acids, although the resulting recombinantly produced protein contains two additional amino acids at the amino terminus (Gly-Ser). The tac promoter may be induced by the addition to cultured cells of, e.g., 1–5 mM isopropyl-beta-D-thiogalactopyranoside (IPTG; Fluka, Milwaukee, Wis.) and provides for high-level expression.

Plasmid pGEX-4T-2 was prepared by digestion with the restriction endonucleases BamHI and XhoI according to the manufacturer's instructions and subjected to horizontal agarose gel electrophoresis and band extraction using the UltraClean™ GelSpin kit (Mo Bio Laboratories). Restricted ANT cDNAs were ligated with the restricted expression vector DNA as described in the preceding Examples. Competent *E. coli* cells (strain TOP10F'; Invitrogen) were transformed with ligation mixtures containing the prokaryotic vector construct according to the manufacturer's instructions. Single colonies were selected for grown in 3–5 ml of LB broth containing 50 ug/ml ampicillin, and plasmid DNA was isolated from the bacterial cultures using the WIZARD™ Plus Series 9600 Miniprep Reagents System (Promega) and restriction mapped. One isolate of a GST-huCypA expression construct having the predicted restriction map (based on the nucleotide sequences of the expression vector and human CypA) was selected for further experiments and designated "pMK10-GST-huCypA."

Example 9
Cloning and Expression of His-Tagged Cyclophilin D (His6x-CypD) Fusion Proteins in Bacteria
A. PCR Amplification of CypD cDNAs A cDNA library prepared from total cellular mRNA prepared from human heart was obtained from a commercial source (Clontech, Palo Alto, Calif.). CypD cDNAs were amplified from the cDNA library by polymerase chain reactions (PCR) in a thermal cycler using the following primers, AMPLITAQ™ DNA Polymerase (Perkin-Elmer), and reagents and buffers supplied in a GENEAMP™ PCR Reagent Kit (Perkin-Elmer), according to the manufacturer's instructions. In the following representations of the PCR primers, underlined nucleotides indicate sequences complementary to the 5'-ends and 3'-ends of the CypD cDNAs, double-underlined nucleotides indicate recognition sequences for the restriction enzymes XhoI (recognition sequence: 5'-CTCGAG) and Asp718 (recognition sequence: 5'-GGTACC), and the huCypD start codon (ATG) and the reverse complement of the stop codon (TAA) are emboldened.

For human CypD (huCypD; SEQ ID NO:39), primers having the following nucleotide sequence were used:
Forward (sense):

5'-ATTAATCTCGAGTATGCTGGCGCTGCGCTGC, and                                                    SEQ ID NO:41

Reverse (antisense):

5'-TATTAAGGTACCTTAGCTCAACTGGCCACAGT

SEQ ID NO:42.

B. Generation of 6xHis-CypD Expression Constructs

The expression vector pBAD/His ("B" derivative; Invitrogen) was used. This vector contains the following elements operably linked in a 5' to 3' orientation: the inducible, but tightly regulatable, araBAD promoter; optimized *E. coli* translation initiation signals; an amino terminal polyhistidine (6×His)-encoding sequence (also referred to as a "His-Tag"); an XPRESS™ epitope-encoding sequence; an enterokinase cleavage site which can be used to remove the preceding N-terminal amino acids following protein purification, if so desired; a multiple cloning site; and an in-frame termination codon.

Plasmid pBAD/His DNA was prepared by digestion with the restriction endonucleases XhoI and Asp718 according to the manufacturer's instructions and subjected to horizontal agarose gel electrophoresis and band extraction using the UltraClean GelSpin kit (Mo Bio Laboratories). Restriction enzyme digested CypD cDNA was ligated with restricted expression vector DNA using T4 DNA ligase (New England Biolabs, Beverly, Mass.) using the manufacturer's reaction buffer and following the manufacturer's instructions. Competent *E. coli* cells (strain TOP10F'; Invitrogen) were transformed with ligation mixtures containing the prokaryotic vector construct according to the manufacturer's instructions. Single colonies were selected and grown in 3–5 ml of LB broth, and plasmid DNA was isolated from the bacterial cultures using the WIZARD™ Plus Series 9600 Miniprep Reagents System (Promega). One isolate of a 6×His-huCypA expression construct having the predicted restriction map (based on the nucleotide sequences of the expression vector and human CypD, SEQ ID NO:39) was selected for further experiments and designated "pMK11-6×His-huCypD."

Example 10
Cloning and Expression of Glutathione S-Transferase-Cyclophilin D (GST-CypD) Fusion Proteins in Bacteria
A. PCR Amplification of CypD cDNAs CypD cDNA was amplified from a cDNA library prepared from total cellular mRNA (Clontech, Palo Alto, Calif.) by PCR in a thermal cycler using the following primers, AMPLITAQ™ DNA Polymerase (Perkin-Elmer), and reagents and buffers supplied in a GENEAMP™ PCR Reagent Kit (Perkin-Elmer), according to the manufacturer's instructions. In the following representations of the PCR primers, underlined nucleotides indicate sequences complementary to the 5'-ends and 3'-ends of the CypD cDNAs, double-underlined nucleotides indicate recognition sequences for the restriction enzymes XhoI (recognition sequence: 5'-CTCGAG) and BamHI (recognition sequence: 5'-GGATCC), and the huCypA start codon (ATG) and the reverse complement of the stop codon (TAA) are emboldened.

For huCypD, primers having the following nucleotide sequence were used:
Forward (sense):

5'-TTATGGATCCATGCTGGCGCTGCGCTGC, and                                                    SEQ ID NO:43

Reverse (antisense):

5'-TAATCTCGAGTTAGCTCAACTGGCCACAGT

SEQ ID NO:44.

B. Generation of GST-CypD Expression Constructs

The CypD PCR products were digested with the restriction endonucleases XhoI and BamHI (both enzymes from Roche Molecular Biochemicals) according to the manufacturer's recommendations using manufacturer-supplied reaction buffers. Restricted DNAs were purified by horizontal agarose gel electrophoresis and band extraction using the UltraClean™ GelSpin kit (Mo Bio Laboratories, Inc.).

The expression vector pGEX-4T-2 (Amersham Pharmacia Biotech) was used to generate huCypD fusion proteins comprising an enzymatic polypeptide and an CypD polypeptide. This vector comprises a lacI$^q$ (repressor) gene a lac promoter operably linked to a glutathione S-transferase (GST) gene from *Schistosoma japonicum*. (Smith et al., 1988, *Gene* 67:31–40), the coding sequence of which has been modified to comprise a thrombin cleavage site-encoding nucleotide sequence immediately 5' from a multiple cloning site. GST fusion proteins can he detected by Western blots with anti-GST or by using a colorimetric assay; the latter assay utilizes glutathione and 1-chloro-2-4-dinitrobenzene (CDNB) as substrates for GST and yields a yellow product detectable at 340 nm (Habig et al., 1974, *J. Biol. Chem.* 249:7130–7139). GST fusion proteins produced from expression constructs derived from this expression vector can be purified by, e.g., glutathione affinity chromatography, and the desired polypeptide released from the fusion product by thrombin. Thus, this expression vector provides for the rapid purification of fusion proteins, and release of proteins with relatively few extraneous N-terminal amino acids, although the resulting recombinantly produced protein contains two additional amino acids at the amino terminus (Gly-Ser). The tac promoter may be induced by the addition to cultured cells of, e.g., 1–5 mM isopropyl-beta-D-thiogalactopyranoside (IPTG; Fluka, Milwaukee, Wis.) and provides for high-level expression.

Plasmid pGEX-4T-2 was prepared by digestion with the restriction endonucleases BamHI and XhoI according to the manufacturer's instructions and subjected to horizontal agarose gel electrophoresis and band extraction using the Ultra-Clean™ GelSpin kit (Mo Bio Laboratories). Restricted ANT cDNAs were ligated with the restricted expression vector DNA as described in the preceding Examples. Competent *E. coli* cells (strain TOP10F'; Invitrogen) were transformed with ligation mixtures containing the prokaryotic vector construct according to the manufacturer's instructions. Single colonies were selected for grown in 3–5 ml of LB broth containing 50 ug/ml ampicillin, and plasmid DNA was isolated from the bacterial cultures using the WIZARD™ Plus Series 9600 Miniprep Reagents System (Promega) and restriction mapped. One isolate of a GST-huCypD expression construct having the predicted restriction map (based on the nucleotide sequences of the expression vector and human CypD) was selected for further experiments and designated "pMK12-GST-huCypD."

Example 11

Cloning and Expression of Cyclophilin D-Green Fluorescent Protein (CypD-GFP) Fusion Proteins A. PCR Amplification of CypD cDNAs CypD cDNA was amplified from a cDNA library prepared from total cellular mRNA prepared from human heart (Clontech, Palo Alto, Calif.) by PCR in a thermal cycler using the following primers, AMPLITAQ™ DNA Polymerase (Perkin-Elmer), and reagents and buffers supplied in a GENEAMP™ PCR Reagent Kit (Perkin-Elmer), according to the manufacturer's instructions. In the following representations of the PCR primers, underlined nucleotides indicate sequences complementary to the reading frame of cypD, double-underlined nucleotides indicate recognition sequences for the restriction enzymes XhoI (recognition sequence: 5'-CTCGAG) and BamHI (recognition sequence: 5'-GGATCC), and the huCypD start codon (ATG) is emboldened.

Primers having the following nucleotide sequence were used:

Forward (sense):

5'-GGGCCCCTCGAGCCCGCG<u>ATGCTGGCGCTGCGCTGC</u>, and SEQ ID NO:45

Reverse (antisense):

5'-CCCGGTGGATCCGC-GCT-CAA-CTG-GCC-ACA-GTC SEQ ID NO:46.

The BamHI site in the immediately preceding primer is positioned such that the amplification product lacks the normal termination codon for cypD, and the cypD reading frame (indicated in the above representation by dashes between codons) is fused with that of the enhanced cyan fluorescent protein (ECFP) DNA in pECFP-N1 (infra).

B. Generation of CypD-ECFP Expression Constructs

The expression vector pECFP-N1 (Clontech Laboratories, Inc.) was restriction enzyme digested with BamHI and XhoI. In the desired ligation product formed from the preceding restriction fragments, the BamHI site in pECFP-N1 is linked to the BamHI site in the ANT3-encoding fragment, and the XhoI site in the CypD-encoding fragment is linked to the XhoI site in pECFP-N1, and the resultant plasmid encodes a CypD-CFP fusion protein. The term "CypD-ECFP fusion protein" indicates a single contiguous polypeptide chain that has (1) an amino terminal polypeptide portion polypeptide portion corresponding to human CypD, and (2) a carboxy terminal polypeptide portion corresponding to enhanced cyan fluorescent protein (ECFP), having an excitation maximum at 433 nm (minor peak at 453 nm) and a peak emission at 475 nm (minor peak at 501 nm).

The restriction enzyme digested DNAs were ligated to one another using T4 DNA ligase under standard conditions known in the art. Competent *E. coli* cells (strain DH5α; Life Technologies, Inc.) were transformed with the ligation mixtures according to the manufacturer's instructions. Single colonies were selected and grown in 3–5 ml of LB broth, and plasmid DNA was isolated from the bacterial cultures using the WIZARD™ Plus Series 9600 Miniprep Reagents System (Promega) and restriction mapped. One isolate of a huCypD-ECFP expression construct having the predicted restriction map (based on the nucleotide sequences of the expression vector and human CypD) was selected for further experiments and designated "pMK13-CypD-ECFP."

C. Expression and Intracellular Localization of CypD-ECFP Fusion Proteins

The expression and intracellular localization of the CypD-ECFP fusion protein described in the immediately preceding section was examined by fluorescent microscopy. COS-1 or 293 cells were grown to confluence and 1 ml of cells was mixed with 1 ml of Opti-MEM™ I reduced serum media (Life Technologies, Inc.) a solution comprising 0.2, 1.0 or 2.0 ug of DNA (pECFP-N1, pMK13-CypD-CFP, or no vector control) and 3–4 ul LipofectAMINE™ (Life Technologies, Inc.). After incubation for 5 hours, 1 ml of media with 20% fetal calf serum was added, and the cells were incubated for an additional period of time, with changes of media every 24 hours, such that the total period of incubation was approximately 48 hours.

The transformed COS-1 and 293 cells were then examined by fluorescent microscopy using a GFP filter (excitator, 450±25 nm; dichroic, 480 nm; emitter, 485 nm, long pass; Nikon, Inc., Melville, N.Y.). Cells transformed with 0.2 or 1.0 ug of pMK13-CypD-ECFP DNA showed punctate fluorescence indicative of mitochondrial delivery of the CypD- ECFP fusion protein. Cells transformed with a higher amount (2.0 ug) of pMK13-CypD-ECFP DNA had some low level cytosolic fluorescence, although most of the cells showed punctate fluorescence. The COS-1 cells generally fluoresced to a greater degree than the 293 cells, perhaps indicating a higher degree of transformation and/or expression. Cells transformed with the expression vector pECFP-N1 showed only low levels of cytosolic fluorescence, and control (mock transformed) cells exhibited no detectable fluorescence. The fluorescent microscopy results indicate that the CypD-ECFP fusion protein localizes exclusively to mitochondria.

Example 12
Purification of His-Tagged Human CypD Protein

The cyclophilin expression constructs described in the preceding Examples may be used to produce cyclophilin proteins and fusion proteins that are used as ligands in the assays described in subsequent Examples.

For example, the expression construct for (6xHis)—XPRESS™ epitope)—(human cyclophilin D) described in the Example 9 was used to produce His-tagged CypD fusion protein. $E.\ coli$ (strain DH5α) cells harboring pMK11-6× His-huCypD were cultured overnight in TB or LB media with ampicillin (00 ug/ml) at 37° C. with agitation. Overnight cultures were diluted in fresh media to $OD_{600}$ of 0.1 and were then incubated at 37° C. with agitation for about 2 hours, i.e., until the $OD_{600}$ was about 0.5. To induce expression, L-arabinose was added from a stock 20% solution to a final concentration of 0.01%. The cultures were then incubated as before for about 4 more hours in order to allow for maximal production of the His-tagged CypD fusion protein.

The bacterial cells were harvested by centrifugation (the dry pellets can be frozen and stored at −80° C. at this point if desired). The pellets were resuspended in an appropriate volume of PBS with imidazole (3 mM) and protease inhibitors (pepstatin, leupeptin, phenylmethylsulfonyl fluoride (PMSF) and/or aprotinin {all from Sigma} present at effective levels (typically 10 μg/mL). The resuspended cells were sonicated for 20 seconds and the lysate was cleared by centrifugation at 14,000×g for 20 minutes at 4° C.

The cleared lysate material is then used to prepare His-tagged huCypD in a variety of ways known to those skilled in the art. Typically, the lysate is added to Nickel beads (agarose or magnetic, although agarose Nickel beads appear to provide better specific yields of protein). About 50 ul of Nickel agarose beads (Qiagen) were added to 500 ul of lysate and incubated for 2 to 48 hours with agitation at 4° C. The beads were briefly washed and His-tagged huCypD was released therefrom by treatment with imidazole (50 to 500 mM, preferably 250 mM, pH from about 4 to about 6) or EDTA (10 to 500 mM, preferably 100 mM, pH from about 4 to about 8); in the experiment described, 100 mM EDTA was used.

The (6xHis)—(XPRESS™ epitope)—(human cyclophilin D) fusion protein is soluble and may be used directly in the assays described in the following Examples. However, if desired, the recombinant huCypD protein expressed from pMK11–6xHis-huCypD can be treated with enterokinase to liberate the His-Tag/XPRESS™ epitope polypeptide from the huCypD protein. This can be done after the (6xHis)—(XPRESS™ epitope)—(human cyclophilin D) fusion proteins have been bound to Nickel beads, in which case the His-Tag/XPRESS™ epitope polypeptides will be retained on the Nickel beads and the huCypD protein may be prepared by simply extracting the beads and recovering the extracted material.

Cyclophilin A, or CypA fusion proteins, are prepared in like fashion using cells harboring pMK9-6xHis-huCypA (Example 7), the expression construct for (6xHis)—(XPRESS™ epitope)—(human cyclophilin A). ANT-, CypA- and CypD-GFP fusion proteins (Examples, and, respectively) can be engineered to additionally comprise His tags or GST polypeptides for ease of purification, or can be purified from bacterial cells harboring the appropriate expression constructs (for one such protocol, see González and Ward, Protocol I.E, "Purification of GFP" in: *Green Fluorescent Protein: Properties, Applications, and Protocols,* Chalfie, M., and Kain, S., eds., John Wiley & Sons, Inc., New York, 1998, pages 289–294).

Example 13
Preparation of Expression Constructs for Fusion Proteins Derived from Other Mitochondrial Factors Using the teachings of the specification, one skilled in the art can prepare fusion protein derivatives of other mitochondrial factors, including proteins thought to be or suspected of being part of the mitochondrial permeability transition (MPT) pore and other proteins thought to or suspected of interacting with one or more components of the MPT pore. Such fusion proteins may include, by way of example and not limitation, His-tagged proteins, epitope-tagged proteins, GST fusion proteins and GFP fusion proteins.

Table 1 lists (1) mitochondrial factors thought to be or suspected of being part of the mitochondrial permeability transition (MPT) pore and (2) other proteins thought to or suspected of interacting with one or more components of the MPT pore. Table 1 further describes available nucleotide sequence information for the genes encoding these mitochondrial factors, from which one skilled in the art could design oligonucleotide primers to be used in PCR reactions to amplify DNA fragments having (a) protein-coding sequences for one of the factors described in Table 1 and (b) restriction enzyme sites at the ends of the amplified DNAs appropriate for cloning into a desired expression vector.

TABLE 1

Mitochondrial Pore Components and Sequences

| Abbreviation | Full Name/Source | Source of Nucleotide Sequence Information |
|---|---|---|
| ANT | Adenine Nucleotide Translocator | |
| ANT-1 | Homo sapiens | SEQ ID NO:1 |
| ANT-2 | H. sapiens | SEQ ID NO:2; GenBank Acc. No. AA874983 |
| ANT-3 | H. sapiens | SEQ ID NO:3 |
| ANT-4 | H. sapiens | WO 99/07845 (SEQ ID NOS:1, 3) |
| ANT | Solanum tuberosum | GenBank Acc. No. X62123 |
| ANT | Plasmodium falciparum | GenBank Acc. No. U04335 |
| PBzR | Peripheral Benzo-diazepine Receptor | |
| PBzR | H. sapiens | GenBank Acc. Nos. Z82214, L21951, M36035 |
| PBzR-related sequences | H. sapiens | GenBank Acc. Nos. L21950, AA490268 |
| PRAX | PBzR-Associated Protein | |
| PRAX-1 | H. sapiens | GenBank Acc. Nos. AI668824, NM_004758, AF039571 |
| Pap20 | Mus musculus | GenBank Acc. No. AF020338 |
| VDAC | Voltage Dependent | |

TABLE 1-continued

Mitochondrial Pore Components and Sequences

| Mitochondrial Pore Components | | Source of Nucleotide Sequence Information |
|---|---|---|
| Abbreviation | Full Name/Source | |
| *Anion Channel* | | |
| VDAC-1 | H. sapiens | GenBank Acc. Nos. NM_003374, L06132 |
| VDAC-2 | H. sapiens | GenBank Acc. Nos. NM_003375, L06328 |
| VDAC-3 | H. sapiens | GenBank Acc. No. NM_005662, S75494; |
| VDAC-4 | H. sapiens | GenBank Acc. No. S75651 |
| HACH (human anion channel) | H. sapiens | U.S. Pat. No. 5,780,235 (SEQ ID NO:2) |
| VDAC-1 | M. musculus | GenBank Acc. No. U89987 |
| VDAC-2 | M. musculus | GenBank Acc. No. U89988 |
| VDAC-3 | M. musculus | GenBank Acc. No. U89989 |
| VDAC | Drosophila melanogaster | GenBank Acc. No. U70314 |
| VDAC | Saccharomyces cerevisiae | GenBank Acc. No. M34907 |
| VDAC-1a | Zea mays | GenBank Acc. No. AF178950 |
| VDAC-1b | Z. mays | GenBank Acc. No. AF178951 |
| VDAC-2 | Z. mays | GenBank Acc. No. AF178952 |
| Cyp | *Cyclophilins* | |
| CypA | H. sapiens | SEQ ID NO:26 |
| CypC | H. sapiens | U.S. Pat. No. 5,447,852 (SEQ ID NO:4) |
| CypD | H. sapiens | SEQ ID NO:39; GenBank Acc. No. NM_005038 |
| Cyp-60 | H. sapiens | U.S. Pat. No. 5,968,802 (SEQ ID NO:3) |
| CypA | Schistosoma mansoni | GenBank Acc. No. U50388 |
| CypB | Schistosoma japonicum | GenBank Acc. No. U50389 |
| CypB | Orpinomyces sp. PC-2 | GenBank Acc. No. U17900 |
| cyclophilins | M. musculus | GenBank Acc. Nos. AI892042, AI875905 |
| CAML | *Calcium Modulating Cyclophilin Ligand* | |
| CAML | H. sapiens | U.S. Pat. No. 5,523,227 (SEQ ID NO:1) |
| CAML | M. musculus | GenBank Acc. No. AA955975 |

Example 14
Antibodies

Antibodies useful in the method assays of the invention may be prepared by those skilled in the art utilizing the teachings of the present disclosure in combination with known methods. The preparation of antibodies to human ANT3 is described in this Example, as is the commercial availability of some useful supplementary antibodies.

A. Preparation of an Antibody Specific for Human ANT3

A monospecific (antipeptide) antibody specific for huANT3 was prepared as follows. A synthetic polypeptide corresponding to a portion of huANT3 located near the carboxy terminus and predicted to have high antigenicity according to the Jameson-Wolf Index (Wolf et al., *Comput. Appl. Biosci.* 4:187–191 (1988) was synthesized using known means by Alpha Diagnostic International (San Antonio, Tex.) and determined to be at least about 70% pure, preferably at least about 90% pure, by HPLC and MS analyses. The sequence of the synthetic polypeptide (SEQ ID NO:30) is:

Cys-Trp-Arg-Lys-Ile-Phe-Arg-Asp-Glu-Gly-Gly-Lys-Ala-Phe-Phe

The synthetic polypeptide was conjugated to a carrier molecule, keyhole limpet hemocyanin (KLH), using MSB (m-maleimidobenzoyl-N-hydroxysuccinimnide ester; Pierce Chemical Co., Rockford, Ill.), and the conjugated material was used to immunize several rabbits, according to known means (Collawn and Paterson, Units 11.14 and 11.15 in Chapter 11 in: *Short Protocols in Molecular Biology*, 2nd Ed., Asubel et al., eds., John Wiley & Sons, New York, N.Y. (1992) 11:37–41. The rabbits were bled at 0 (preimmune, 2 mL), 7, 9, 11, 13 (15 mL for each bleed) or 15 (50 mL) weeks post-inoculation. Sodium azide (0.1%) was added to the bleeds as preservative.

B. Useful Commercially Available Primary Antibodies

Antibodies to glutathione-S-transferase (GSl), useful for detecting GST fusion proteins, or for linking GST fusion proteins to a solid support, have been described and are commercially available (BD Pharmingen, San Diego, Calif.; Clontech, Palo Alto, Calif.; Zymed Laboratories, Inc., South San Francisco, Calif.; Sigma Chemical Co., St. Louis, Mo.; and Oxis International, Inc., Portland, Oreg.).

Antibodies to amino or carboxy terminal 6xHis tags, useful for detecting His-tagged fusion proteins, or for linking His-tagged fusion proteins to a solid support, have been described and are commercially available (Invitrogen, Carlsbad, Calif.; Clontech; and Berkley Antibody Co., Richmond, Calif.). For ease of detection, anti-(His tag) is available as a conjugate linked to one of a variety of enzymes for which detectable substrates and/or products are available, including horseradish peroxidase (Clontech).

Antibodies to green fluorescent protein (GFP), useful for detecting GFP fusion proteins, or for linking GFP fusion proteins to a solid support, have been described and are commercially available (Clontech; Berkley Antibody Co.; Torrey Pines Biolabs, San Diego, Calif.; Aurora Biosciences Corp., San Diego, Calif.). For ease of detection, anti-GFP is available as a conjugate linked to one of a variety of enzymes for which detectable substrates and/or products are available, including horseradish peroxidase and alkaline phosphatase (both from Clontech).

Antibodies to the XPRESS™ epitope, useful for detecting fusion proteins comprising the XPRESS™ epitope, or for linking fusion proteins comprising the XPRESS™ epitope to a solid support, have been described and are commercially available (Invitrogen).

Example 15
Assay of huANT3-huCypD Interactions

The reagents described in the preceding Examples can be used in a variety of assays designed to measure interactions between components of the mitochondrial permeability transition pore (MNT). The present Example describes immunoassays designed to measure interactions between an isoform of the mitochondrial adenine nucleotide translocator (huANT3) and cyclophilin D (huCypD).

A Preparation of Nickel Beads: His-Tagged huANT3 Complexes

Pelleted mitochondria from noninfected *T. ni* cells, or *T. ni* cells infected with a baculovirus expressing His-tagged-huANT3 (see Example 3) were prepared as follows: *T. ni* cells were prepared by a subcontractor (PharMingen, San Diego, Calif.) as portions of about 250 mg of cells per tube. Each portion was suspended in 1 ml of MSB with protease inhibitors (leupeptin, final concentration 10 ug/ml; pepstatin, final concentration 10 ug/ml; aprotinin, final concentration, 2 ug/ml; phenylmethylsulfonyl fluoride {PMSF}, final concentration, 100 $\mu$M; all from Sigma Chemical Co., St Louis, Mo.). The resuspended cell suspensions were frozen and thawed twice, then homogenized using a rotating teflon-coated probe and a close-fitting glass container (10 passes). The cellular homogenate was centrifuged (3,700 rpm, approximately 1,500×g) at 4° C. for 5 minutes; this supernatant from the first spin was saved. The pellet was washed with about 500 μl of MSB with protease inhibitors, centrifuged (3,800 rpm, approximately 1,600×g) at 4° C. for 5 minutes, and supernatant from this spin was combined with the supernatant from the first spin. The combined supernatant was centrifuged (14,000 rpm, approximately 20,800×g) at 4° C. for 15 minutes, and the pellet was resuspended in 300 μl of a 1:1 solution of (a) 20 mM MOPS and (b) MSB, wherein both (a) and (b) contain the previously described protease inhibitors. The resultant suspension was frozen and thawed three times.

One hundred (100) μl of T. ni mitochondria (9.83 μg/ml) was thawed slowly on ice and then centrifuged at 4° C. for 15 minutes to pellet mitochondria. The pellet was solubilized in 100 μl Solubilization Buffer (20 mM KH2PO4, 0.3 M NaCl, 20 uM imidazole, 10 mM HEPES, pH 7.2, 3% Triton X-100) that had been freshly made to be 1 mM 2-mercaptoethanol, and to which the following protease inhibitors had been freshly added: pepstatin, leupeptin, phenylmethylsulfonyl fluoride and aprotinin (all from Sigma) to an effective level (typically 10 μg/mL) with for 2 minutes at ambient temperature, or 3 minutes at 4° C. The solution was then diluted to a final volume of 300 ul with Dilution Buffer (20 mM $KH_2PO_4$, 20 mM imidazole, 50 mM NaCl, 0.5% Triton X-100, pH 7.2).

B. Assays of huANT3: huCypD Interactions

Aliquots of 60 ul of T. ni mitochondria were added to 75 ul aliquots of a slurry of Nickel-plated agarose beads (Qiagen) that had been prewashed once in Washing Buffer (20 mM $KH_2PO_4$, 20 mM imidazole, 50 mM NaCl, 1.3% Triton X-100, pH 7.2). The beads were incubated for an appropriate period of time (typically, about 5 to 15 minutes, but incubations can proceed from 2 to 30 minutes with no visible change in the results) at ambient temperature in a rotating test tube stand in order to provide continual mixing. In some samples, a GST-CypD fusion protein (Example 10) was added (12 ug per tube) as a ligand for huANT3; in some of these samples, cyclosporin A (final concentration, 10 uM; from a 2 uM stock solution in ethanol), which specifically blocks the action of CypD, was also added.

The complexes formed in the incubations may be diagramed as follows (where "—" indicates a chemical bond and ":" indicates an interaction between two molecules):

(Bead)—Nickel:6xHis-ANT3:CypD—GST.

The incubations were stopped by adding an excess (1 ml) of cold (ie., kept on ice) Washing Buffer. The beads were pelleted by low speed centriflugation for 30 seconds, washed once with 1 ml cold Washing Buffer and immediately extracted by a number of methods. To determine total bound ligand (GST-CypD), 80 ul of 1×NuPAGE SDS Sample Buffer (Novex, San Diego, Calif.) was added to the beads which were then placed in a boiling water bath for about 5 to 10 minutes. To determine the amount of ligand (GST-CypD) bound to ANT, 60 ul of Elution Buffer (50 to 500 mM, preferably 250 mM imidazole, pH from about 4 to about 6; or 10 to 500 mM, preferably 100 mM, EDTA, pH from about 4 to about 8; in the experiment described, 100 mM EDTA was used) was added to a second set of otherwise identically treated beads. Because EDTA chelates the Nickel ions to which the His-tag (6xHis) portion of the His-tagged huANT3, the latter entity is displaced from the Nickel beads by the addition of EDTA. As the His-tagged ANT3 protein is eluted from the Nickel beads, GST-CypD protein specifically bound to the ANT3 polypeptide is also eluted. Without wishing to be bound by theory, it is thought that this occurs because (1) the CypD portion of the GST-CypD fusion protein remains bound to ANT polypeptide sequences and is carried along with the His-tagged ANT3 protein, or (2) the displacement of the His-tagged ANT3 proteins from the Nickel beads results in the destabilization and dissociation of the entire ANT3:CypD complex, or some combination of these and/or other mechanisms.

The extracts were evaluated by Western analysis. In brief, loading dye was added to the extracts as needed, the samples were placed in boiling water for about 5 to 10 minutes and were then electrophoresed on precast acrylamide gels (Novex) and electroblotted onto a nitrocellulose filter. An antibody specific for the GST portion of the CypD-GST fusion protein was used as a primary antibody in probing the filter and, as a result, endogenous cyclophilin D protein does not register in the assay. The filter was incubated first with murine anti-GST (BD Pharmingen) diluted 1:10,000 for 60 minutes, and then with sheep anti-mouse Ig antibody (Amersham Pharmacia Biotech, Arlington Heights, Ill.) conjugated with horseradish peroxidase diluted 1:5,000 for about 30 to about 60 minutes (both incubations took place at ambient temperature). The filter was developed by incubation with an acridan-based substrate for horseradish peroxidase, the product of which releases a high level, sustained output of light (ECL Plus Western blotting detection system, Amersham Pharmacia Biotech). The filter was exposed to film for an appropriate exposure time (typically, 1 or 2 minutes) and was then stripped and reprobed with an antibody specific for human ANT3 (Example 14).

Figure 9:
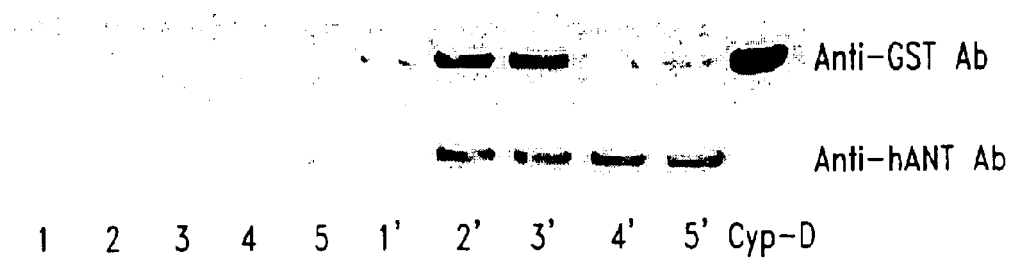
FIG. 9 shows the results of an assay that measures interactions between human ANT3 and human CypD.

Results of a typical experiment are shown in FIG. 9. At the far right, 0.5 ug of purified CypD-GST fusion protein is revealed via its reaction with the anti-GST. Proteins released by EDTA elution are visualized in lanes 1' through 5'. In lane 1', no His-tagged huANT3 was present in the samples, and only a slight amount of the CypD-GST bound to the Nickel-coated agarose beads in a non-specific fashion. In lanes 2' and 3', His-tagged huANT3 was present in the samples, and the amount of CypD-GST retained is visibly increased by roughly an order of magnitude.

In addition to the usual components, the sample in lane 3' (as well as that in lane 3) was made 0.5% ethanol as a control for the samples to which cyclosporin A (Sigma), which is prepared as an ethanol-based stock solution, was added. As can be seen by comparing lanes 2' and 3' in FIG. 7, the presence of 0.5% ethanol had no visible effect on the results of the assay. In lane 4', the CypD-GST fusion protein was preincubated with 10 uM cyclosporin A before being contacted with the Nickel beads:His-tagged ANT3 mixture; as expected, the presence of cyclosporin A eliminated ANT-mediated CypD-GST retention.

In lane 5', Nickel beads:His-tagged ANT3:CypD-GST complexes were preformed before the addition of 10 uM cyclosporin A. Under these conditions, the order of addition had no discernible impact on the results. The fact that the loading and recovery was consistent from tube to tube throughout the experiment is shown by the consistent recovery of ANT3 in lanes 2', 3', 4' and 5'.

Lanes 1 through 5 represent EDTA-eluted samples corresponding to those of lanes 1' through 5' which were stripped of bound protein (by addition of 1×NuPAGE SDS Sample Buffer and placing in a boiling water bath for 10 minutes) after the EDTA-mediated elution of bound proteins. As can be seen in FIG. 9, no detectable CypD-GST or His-tagged ANT3 remained bound to the Nickel-coated beads after elution with EDTA.

These results demonstrate that the assay reflects known parameters of human CypD and ANT. That is, the CypD-GST fusion protein specifically binds His-tagged ANT3 on a solid support, and this binding is inhibited by cyclosporin A.

Example 16
Other In Vitro Assays of ANT3-CypD Interactions

The reagents and systems described herein can be used in a variety of in vitro assays of interactions of MPT pore components with each other and/or with other mitochondrial factors. Using ANT and CypD as examples, this Example describes such other uses and embodiments of the compositions and methods disclosed herein.

For example, in one related embodiment, the CypD ligand that is added in the binding assays is an epitope-tagged CypD fusion protein, wherein the epitope is, for example, a 6×His "tag" or the an XPRESS™ epitope (Example 9). In this mode, the amount of CypD ligand present in each sample is measured using antibodies, or other detectable reagents, that specifically bind the epitope.

In another related embodiment, the CypD ligand that is added in the binding assays is a CypD-GFP fusion protein (Example 11). In this mode, the amount of CypD ligand present in each sample is measured using a flourometer.

In a further related embodiment, the ANT fusion protein used in the assay is an ANT-GST fusion protein (Example 2) that is attached to glutathione coated beads (Sigma), and the CypD ligand is, for example, an epitope-tagged CypD fussion protein, wherein the epitope is, for example, a 6×His "tag" or the an XPRESS™ epitope (Example 9), or a CypD-GFP fusion protein (Example 11). A variety of beads and other supports can be used; however, care must be taken to ensure that the CypD ligand used in such assays do not attach to the glutathione bead or other support of choice. In this mode, the amount of CypD ligand present in each sample is measured using antibodies, or other detectable reagents, that specifically bind the epitope, or a fluorometer, whichever is appropriate for the CypD ligand of choice.

In a further related embodiment, the ANT fusion protein used in the assay is an ANT-EYFP fusion protein (Example 5) that further includes a His tag, or other functional group such as a GST polypeptide, that serves as a linker for the purpose of attachment of the ANT-EYFP fusion protein to the support (i.e., Nickel beads if a His-tagged ANT-EYFP fusion protein is used), and the CypD ligand is a CypD-ECFP fusion protein (Example 11). In this mode, a fluorometer is used to measure FRET that occurs when the ANT-EYFP and CypD-ECFP fusion proteins are in close proximity (see the next Example).

These and other embodiments of the assays of the invention may be incorporated into automated assay systems adapted by those skilled in the art. Such automated systems are useful for high throughput screening (HTS) of candidate compounds that influence CypD:ANT interactions (or interactions of MPT pore components with each other and/or with other mitochondrial factors) or chemical libraries comprising such compounds. Such compounds may be further characterized and developed as drug candidates and drugs useful for preventing, treating or curing diseases or disorders resulting from the overexpression or dysfunction of one or more ANT, cyclophilin or cyclosporin proteins, or from the overexpression or dysfunction of a factor that positively regulates or stimulates of one or more ANT, cyclophilin or cyclosporin proteins.

A preferred element of many automated assay systems is the incorporation of a target molecule into a 96-well plate. This format is readily adaptable for use in a variety of automated label detection systems. For HTS assays, robotic label detection systems are preferred. When fluorescent CypD ligands are used in such HTS assays, an automatic fluorescence counter is used and may be, for example, a FLUOROCOUNT™ Counter (Packard Instrument Company, Meriden, Conn.).

Example 17
FRET-Based Assays of Interactions Between MPT Pore Components and Mitochondrial Factors: General Considerations The preceding Examples describe the production of exemplary reagents and systems that can be used in assays that are based on fluorescence resonance energy transfer (FRET) between two molecules in close physical proximity. Such assays, which can be carried out in vitro or in vivo, and design considerations therefor, are described in general in this Example and in specific for human ANT3:CypD interactions in the subsequent Example.

A. General Description of FRET-Based Assays

In general, energy transfer (ET) is generated from a resonant interaction between two molecules: an energy-contributing "donor" molecule and an energy-receiving "acceptor" molecule. Energy transfer can occur when (1) the emission spectrum of the donor overlaps the absorption spectrum of the acceptor and (2) the donor and the acceptor are within a certain distance (for example, less than about 10 nm) from each other. The efficiency of energy transfer is dictated largely by the proximity of the donor and acceptor, and decreases as a power of 6 with distance. Measurements of ET thus strongly reflect the proximity of the acceptor and donor compounds, and changes in ET sensitively reflect changes in the proximity of the compounds such as, e.g., association or dissociation of the donor and acceptor.

In the present invention, the donor and acceptor compounds are typically both fusion proteins derived from MPT pore components and/or mitochondrial factors. In the assays of the invention, the donor and acceptor compounds (fusion proteins) interact with each other under certain conditions in such a manner as to achieve sufficient proximity to one another for a particular type of energy transfer to occur. In certain aspects of the invention, such interactions are influenced (e.g., enhanced, modulated, inhibited or blocked) by one or more chemical agents, with a resulting increase (enhanced interaction) or decrease (reduced interaction) in energy transfer that can be monitored. Thus, measurements of degree or rate of energy transfer between the donor and acceptor fusion proteins serve as part of an assay for interactions between the two endogenous (mitochondrial and/or cellular) proteins from which the fusion proteins are derived.

Although not required in the present invention, the donor molecule and the acceptor molecule can both be, for ease of measurement, light emission molecules, such as fluorescent, phosphorescent, and chemiluminescent molecules, which emit light when excited by excitation light. Preferable donor-acceptor combinations that can be used with the present invention are fluorescent donors with fluorescent or phosphorescent acceptors, or phosphorescent donors with phosphorescent or fluorescent acceptors. "Fluorescence" refers to luminescence (emission of light) that is caused by the absorption of radiation at one wavelength ("excitation"), followed by nearly immediate reradiation ("emission"), usually at a different wavelength, that ceases almost at once when the incident radiation stops. At a molecular level, fluorescence occurs as certain compounds, known as fluorophores, are taken from a ground state to a higher state of excitation by light energy; as the molecules return to their ground state, they emit light, typically at a different wavelength. "Phosphorescence," in contrast, refers to lumninescence that is caused by the absorption of radiation at one wavelength followed by a delayed reradiation that occurs at a different wavelength and continues for a noticeable time after the incident radiation stops. "Chemiluminescence"

refers to luminescence resulting from a chemical reaction, and "bioluminescence" refers to the emission of light from living organisms or cells, organelles or extracts derived therefrom.

By way of illustration and not limitation, one exemplary class of energy transfer is known as fluorescence resonance energy transfer (FRET). FRET occurs within a molecule, or between two different types of molecules, when energy from an excited donor fluorophore is transferred directly to an acceptor fluorophore (for a review, see Wu et al., *Analytical Biochem.* 218:1–13, 1994). In general, the energy transfer from an excited fluorophore (donor) to an absorber (acceptor) is measured by (1) measuring the spectra (including changes in the spectra) of fluorescence from the donor and acceptor; (2) measuring the speed at which the intensity of the fluorescent intensity of the donor decreases after pulse-laser excitation (i.e., the fluorescence lifetime); or (3) measuring the reduction in intensity of fluorescence from the donor compound (indirect measurement of FRET), or the increase in intensity of fluorescence from the acceptor compound (direct measurement of FRET). Direct measuring of energy transfer involves monitoring the signal from an excited acceptor compound, which increases as the compounds achieve proximity to each other, whereas indirect measuring of energy transfer involves monitoring a signal from an excited donor compound that decreases (ie., is quenched) as the compounds achieve proximity.

B. Pairs of Donor:Acceptor Polypeptide Motifs for FRET-Based Assays

A number of criteria are generally used to determine what combinations of energy-donating compounds (donors) and energy-accepting compounds (acceptors) are acceptable for FRET-based assays of the invention. One criterion is that the emission spectrum of the donor compound should at least partially overlap the absorption spectrum of the acceptor compound, so that energy transfer from the donor to the acceptor can occur. Typically, a donor compounds has an emission peak wavelength herein, "λD(em)") that is within a few nm of the excitation peak wavelength of the acceptor compound [herein, "λA(ex)"]. That is, the difference between D(em) and A(ex) is typically from about 70 nm to about 20 nm or less, with typical values for λD(em)–λA(ex) being 60 nm, 50 nm, 40 nm, 30 nm, 25 nm, 20 nm, 15 nm, 10 nm, 5 nm or 1 nm.

Another criterion is that the emission signal from the excited acceptor compound must be capable of being distinguished from the emission signal from the excited donor compound. An emission signal from an excited donor can be so distinguished if, for example, (1) the wavelength of the emission signal from the excited acceptor is sufficiently distinct from the wavelength of the emission signal from the excited acceptor or (2) the acceptor quenches the emission signal from the excited acceptor.

A variety of classes of compounds can serve as acceptors and donors, and the acceptor and donor can, but need not, belong to the same class of compound. Any appropriate signal-emitting, preferably light-emitting (fluorescent, phosphorescent, or chemiluminescent) polypeptide motif or chemical moiety may be used as a detectable label in the present invention. Chemical moieties may be conjugated to polypeptides according to methods known in the art.

Recombinant production of fusion proteins comprising (1) a polypeptide sequence corresponding to or derived from a mitochondrial factor of interest and (2) a fluorescent polypeptide is a straightforward way to produce homogenous batches of proteins that serve as fluorescent ligands that are useful in the assays of the invention. Table 2 lists appropriately overlapping (in terms of donor emission and acceptor excitation spectra) pairs of fluorescent polypeptide motifs. Green fluorescent proteins are described infra (Example 6). Fusion proteins comprising "FLASH" (fluorescein arsenical helix binder) sequences have been described (Griffin et al., *Science* 281:269–272, 1998).

TABLE 2

Energy Transfer Molecule Donor-Acceptor Pairs for FRET-Based Assays

| | DONORS | | | ACCEPTORS | |
|---|---|---|---|---|---|
| Protein or Motif | Peak Excitation Wave-length | Peak Emission Wave-length | Peak Excitation Wave-length | Peak Emission Wave-length | Protein or Motif |
| Group I Donors | 375–390 nm | 425–475 nm | Suitable For Use With Any Group I Donor: | | |
| EBFP-F64L/S65T/Y66H/Y145F | 380 nm | 440 nm | 433 nm 453 nm* | 475 nm 501 nm* | ECFP-F64L/S65T/Y66W/N1461/M153T/V163A/(±N212L) |
| BFP-Y66H/Y145F | 381 nm | 445 nm | | | |
| BFP-Y66H | 382 nm | 448 nm | 470 nm* (395 nm) | 510 nm | Wildtype GFP |
| BFP-F64M/Y66H/V681 | 385 nm | 450 nm | | | |
| Group II Wildtype GFP | 390–405 nm 395 nm (470 nm*) | 475–525 nm 510 nm | Suitable For Use With Any Group II Donor: | | |
| | | | 502 nm | 512 nm | YFP-S65G/Y66W/S72A/T203Y |
| | | | 508 nm | 528 nm | "FLASH" proteins |
| | | | 513 nm | 527 nm | EYFP-S65G/V68L/S72A/T203Y |
| Group III ECFP-F64L/S65T/ | 425–440 nm 433 nm (453 nm*) | 475–525 nm 501 nm* (475 nm) | Suitable For Use With Any Group III Donor: 502 nm | 512 nm | YFP-S65G/Y66W/ |

TABLE 2-continued

Energy Transfer Molecule Donor-Acceptor Pairs for FRET-Based Assays

| | DONORS | | ACCEPTORS | | |
|---|---|---|---|---|---|
| Protein or Motif | Peak Excitation Wave-length | Peak Emission Wave-length | Peak Excitation Wave-length | Peak Emission Wave-length | Protein or Motif |
| Y66W/N1461/M153T/V163A/(±N212L) | | | 508 nm | 528 nm | S72A/T203Y "FLASH" proteins |
| | | | 513 nm | 527 nm | EYFP-S65G/V68L/S72A/T203Y |
| Group IV Wildtype GFP | 465–495 nm 470 nm* (395 nm) | 475–525 nm 510 nm | Suitable For Use With Any Group IV Donor: 502 nm | 512 nm | YFP-S65G/Y66W/S72A/T203Y |
| RFP-S65C | 479 nm | 507 nm | 508 nm | 528 nm | "FLASH" proteins |
| EGFP, RFP-F64L/S65T | 488 nm | 507 nm | 513 nm | 527 nm | EYFP-S65G/V68L/S72A/T203Y |
| RFP-S65T | 489 nm | 511 nm | | | |
| RFP-F64M/S65G/Q69L | 490 nm | 509 nm | | | |

*Minor excitation or emission peak.

C. Instrumentation for Detecting Energy Transfer

A variety of instruments can be used in methods of the invention to excite an energy transfer molecule that is an energy transfer donor compound and to measure emission from an energy transfer molecule that is an energy transfer acceptor compound. Which instrument(s) is (are) applicable for a particular donor-acceptor pair depends on factors such as (1) the need to apply energy at a wavelength that will excite the donor compound, preferably at or near $\lambda D(ex)$, to samples; (2) the need to measure energy within the emission spectrum of the acceptor compound, preferably at or near $\lambda A(em)$; (3) the type of samples to be assayed in a given program; and (4) the number of samples to be assayed in a given program.

With regard to factors (1) and (2), the spectra of energy being applied to samples to excite a donor compound, and the spectra of energy being emitted by an excited acceptor compound and measured in samples will determine, in general, what type of instrument will be used. For example, although $\lambda D(em)$ should not be identical to $\lambda A(em)$, the minimal acceptable amount of difference between these two values will be influenced by, among other factors, the instrumentation being used. That is, as $\lambda D(em)$ approaches $\lambda A(em)$, instruments capable of resolving closely-spaced wavelengths are required, and an assay using a donor-acceptor pair wherein the difference between $\lambda D(em)$ and $\lambda A(em)$ is less than about 3 to about 5 nm requires a high resolution instrument. Conversely, an assay using a donor-acceptor pair wherein the difference between $\lambda D(em)$ and $\lambda A(em)$ is greater than about 50 to about 75 nm requires an instrument of medium to low resolution.

With specific regard to factor (2), the type of energy being emitted by an excited acceptor compound and measured in samples will determine, in general, what type of instrument will be used. By definition, a fluorometer is a device that measures fluorescent energy and should therefor be part of the instrumentation. A fluorometer may be anything from a relatively simple, manually operated instrument that accommodates only a few sample tubes at a time, to a somewhat more complex manually operated or robotic instrument that accommodates a larger number of samples in a format such as, e.g., a 96-well microplate (such as, e.g., an fmax™ fluorimetric plate reader, Molecular Devices Corp., Sunnyvale, Calif.; or a Cytofluor fluorimetric plate reader, model #2350, Millipore Corp., Bedford, Mass.), or a complex robotic instrument (such as, e.g., a FLIPR™ instrument; see infra) that accommodates a multitude of samples in a variety of formats such as 96-well microplates.

With regard to factor (3), the type of samples to be assayed in a given program, different formats will be appropriate for different types of samples. For example, 96-well microplates are suitable in instances where the cells or isolated organdies of interest adhere to the material of the microplate or to some material applied to the wells of the microplate; however, plastic fluorescence results in a larger background component at excitation wavelengths below about 400 nm. For measurements involving nonadherent cells or organelles, or soluble extracts prepared therefrom, an instrument capable of reading fluorescent signals in glass or polymeric tubes or tubing is preferred. Regardless of what type of format is used, it should allow for the introduction of donor and acceptor compounds, as well as control reagents and compounds being evaluated, into the samples at appropriate points in time.

Factor (4), the number of samples to be assayed in a given program, will influence how automated the instrument will be. For example, when high throughput (HTS) assaying of a large number of samples is desired, robotic or semi-robotic instruments are preferred. However, a fair number of samples can be processed manually, particularly when formats that accommodate large sample numbers (such as, e.g., 96-well microplates) are used.

Depending on the assay, a Fluorometric Imaging Plate Reader (FLIPR™) instrument (Molecular Devices, Sunnyvale, Calif.) is often the instrument of choice for ET-based assays of the invention. The FLIPR™ system (see http://www.moleculardevices.com/pages/flipr.html) has the following desirable features: it uses a combination of a water-cooled, argon-ion laser illumination and cooled CCD camera as an integrating detector that accumulates signal over the period of time in which it is exposed to the image and, as a result, its signal-to-noise characteristics are generally superior to those of conventional imaging optics; it also makes use of a proprietary cell-layer isolation optics that allow signal discrimination on a cell monolayer, thus reducing undesirable extracellular background fluorescence; it provides data in real-time, and can also provide kinetic data (i.e., readings at a multitude of timepoints); it has the ability to simultaneously stimulate and read all 96 wells of a 96-well microplate; it provides for precise control of temperature and humidity of samples during analysis; it includes an integrated state-of-the-art 96-well pipettor, which uses dispensible tips to eliminate carryover between experiments, that can be used to aspirate, dispense and mix precise volumes of fluids from microplates; and, in the case of the FLIPR[384] instrument, it can be adapted to run sample assays in a robotic or semi-robotic fashion, thus providing for analysis of large numbers of samples in shortest amount of time (e.g., up to about a hundred 96-well microplates per day).

Example 18
FRET-Based Assays of ANT3 :CypD Interactions

The reagents and systems described in Examples 1 through 12 can be used in FRET-based assays of CypD:ANT interactions (specifically, huANT3:huCypD). Procedures for performing such assays, which can be carried out in vitro or in vivo, are described in this Example.

A. In Vivo FRET-Based Assays of CypD:ANT Interactions

Cells are transformed (transiently or permanently) with expression constructs that direct the production of two or more fluorescent (or otherwise detectably labeled) mitochondrial fusion proteins that can act as energy transfer donor:acceptor pairs with each other. Alternatively, cells are transformed with a single expression construct that directs the production of two or more fluorescent (or otherwise detectably labeled) mitochondrial fusion protein proteins that make up at least one energy transfer donor:acceptor pair. Transformation and appropriate localization of the fusion proteins is confirmed by, e.g., fluorescence microscopy and/or fluorescence detection for GFP fusion proteins.

In the case of huANT3 and huCypD, the GFP fusion protein derivatives of these mitochondrial factors are used in FRET-based assays of their interaction. Specifically, the donor molecule is huCypD-ECFP ($\lambda$ex, 433 nm, minor peak at 453 nm; $\lambda$em, 475 nm, minor peak at 501 nm; Example 11), and the acceptor molecule is huANT3-EYFP(C) ($\lambda$ex, 513 nm; $\lambda$em, 527 nm), in which the EYFP polypeptide is on the carboxy terminal side of the fusion protein (Example 6). The association (positive interaction) of these fusion proteins can be detected and measured in a variety of ways. First, the transfer of energy from huCypD-ECFP to huANT3-EYFP(C) can be directly detected as an increase in fluorescence from excited acceptor molecules, i.e., as an increase in fluorescence around the peak emission wavelength (527 nm) for huANT3-EYFP(C). Second, the transfer of energy from huCypD-ECFP to huANT3-EYFP(C) can be detected indirectly as a decrease in fluorescence (quenching) from excited donor molecules, i.e., by a decrease in fluorescence around the peak emission wavelength (475 nm, minor peak at 501 nm) for huCypD-ECFP. Conversely, inhibition of molecular interactions, and/or promotion of repulsion (negative interaction) of these fusion proteins can be detected and measured directly , i.e., as an decrease in fluorescence, resulting from decreased energy transfer from huCypD-ECFP and huANT3-EYFP(C), around the peak emission wavelength (527 nm) for huANT3-EYFP(C), or indirectly, i.e., as an increase in fluorescence from excited donor molecules, i.e., by a decrease in fluorescence around the peak emission wavelength (475 nm, minor peak at 501 nm) for huCypD-ECFP.

Transformed cells are contacted with candidate compounds and compositions. The term "candidate compounds and compositions" is meant to encompass chemical compounds, including small organic molecules, polypeptides, proteins, oligonucleotides including ribozymes and other antisense oligonucleotides, nucleic acids including gene therapy and antisense constructs, and extracts from natural biological sources including extracts from particular plants or animal tissues. A detectable signal, e.g., the fluorescence that results from the interaction of from the samples is measured, e.g., over time, including before and after addition of the candidate compound(s) and/or composition(s), or as a single point after an appropriate period of incubation. The results are examined in order to evaluate the effect (positive, negative or neutral) of the candidate compound(s) and/or composition(s) on the interaction of ANT3 and CypD.

Cells are solubilized as need be to ease the entry of compounds that are being tested for their ability to affect CypD:ANT interactions in vivo. Using methodologies known in the art and/or the present disclosure, those skilled in the art will be able to determine appropriate doses, conditions and samples (e.g., whole or permeabilized cells, and appropriate cell types or lines) for assays utilizing specific agents and/or conditions for inducing an altered mitochondrial state. By way of example and not limitation, cells may be permeabilized by the addition of permeabilizing agents such as digitonin, streptolysin O, *Staphylococcus aureus* $\alpha$-toxin ($\alpha$-hemolysin), saponin (all available from Sigma Chemical Co., St. Louis, Mo.; see Sigma catalog entitled "Biochemicals and Reagents for Life Science Research," Anon., 1999, and references cited therein for these permeabilizing agents), or by physical manipulations such as, e.g., electroporation.

In a related embodiment, mitochondria are prepared from cells that have been transformed with expression constructs that direct the production of two or more fluorescent (or otherwise detectably labeled) mitochondrial fusion proteins that can act as energy transfer donor:acceptor pairs. Candidate compounds and compositions are added directly to isolated mitochondria comprising FRET donor:acceptor pairs of fusion proteins, and fluorescence in the samples is measured, e.g., over time, including before and after addition of the candidate compound(s) and/or composition(s), or as a single point after an appropriate period of incubation.

B. In Vitro FRET-Based Assays of CypD:ANT Interactions

FRET-based in vitro assays of CypD:ANT interactions are carried out according to the methods described in this Example and in Example 15. Multiwell plates can be coated with either an ANT-EYFP or a CypD-ECFP fusion protein and then contacted with either a CypD-ECFP or an ANT-EYFP fusion protein, respectively, in the presence or absence of candidate compounds, and the fluorescent signal in each well (which corresponds directly with the number of ANT and CypD molecules in close proximity to one another) can be read by automated or semi-automated fluorometers.

Because in vitro assays do not require that the ANT and CypD fusion proteins co-localize in the same subcellular compartment, either of the ANT-EYFP fusion proteins (i.e., either ANT-EYFP, in which the EYFP polypeptide is located on the carboxy terminus of the fusion protein, or EYFP-ANT, in which the EYFP polypeptide is located on the amino terminus) described herein may be used in such assays.

Example 19
Assay for CypD-ANT Binding Interactions Using Submitochondrial Particles This example describes compositions and methods for assaying CypD binding to submitochondrial particles (SMP) prepared from mitochondria derived from cells expressing recombinant human ANT3. Transfected *T. ni* insect cells expressing His-tagged recombinant human ANT3, as described above in Example 3, were the source of SMP.

SMP preparation was according to a modification of Halestrap et al. (1998 *Biochim. Biophys. Acta* 1366:79–94), and all steps were performed at 4° C. Starting material was one liter of cell culture, corresponding to $1 \times 10^9$ *T. ni* cells. Cells were pelleted by centrifugation and stored frozen at −20° C. For isolation of mitochondria, the cell pellet was thawed and resuspended in 15 ml of mitochondrial isolation buffer (MIB, all reagents from Sigma, St. Louis, Mo., unless otherwise noted): 0.22 M mannitol, 70 mM sucrose, 10 mM Hepes, 0.2 mM EDTA, 0.2 mM 2-mercaptoethanol (2-ME), pH 7.2 plus a standard protease inhibitor cocktail (Roche Molecular Biochemicals, Indianapolis, Ind.). The suspension was subjected to two freeze-thaw cycles by shell-freezing the container in a dry ice/ETOH bath and then thawing the suspension at room temperature, and was then diluted with 20 ml of MIB. The suspension was next homogenized with 10 strokes in a Potter-Elvehjem homogenizer (rheostat setting 28). The resulting homogenate was further diluted with MIB to a volume of approximately 200 ml and centrifuged at 600×g at 4° C. for 10 min. Supernatant fluids were saved and the pellet was resuspended in 20 ml MIB, homogenized as described above, diluted to 100 ml final volume with MIB and again centrifuged for 10 min at 600×g. Supernatants were pooled and pellets were homogenized three additional times as just described, until the supernatant fluid following centrifugation was clear. The pooled supernatant fluids were again centrifuged for 10 min at 600×g to remove contaminating nuclei, which accumulated following centrifugation in the form of pellets having a white appearance. The post-nuclear supernatants were then centrifuged for 15 minutes at 12,000×g to yield a mitochondrial pellet having a pink color, which was resuspended in 8 ml of MIB supplemented with protease inhibitors. Protein concentration was measured using the Pierce BCA (Pierce Chemical Co., Rockford, Ill.) according to the manufacturer's instructions.

Preparation of SMP from isolated *T. ni* mitochondria was performed by a modification of the method of Nicolli et al. (1996 *J Biol Chem* 271(4):2185–92). Briefly, in a 25 ml glass beaker supported in an ice/water bath, mitochondria were suspended at 30 mg/ml (based on protein content) in Mito B buffer (0.25 M Sucrose, 10 mM Tris-Cl pH 7.4, 0.1 mM EGTA-Tris) at 30 mg/ml and sonicated under an argon stream using a Sonofier™ model 450 probe tip sonicator (Branson Ultrasonics, Inc. Danbury, Conn.) set at 60% cycle and at a power setting of 20 (Brinkmann Instruments, Westbury N.Y.) for three sonication periods, each lasting three minutes. Unbroken mitochondria were then removed by centrifugation at 8000×g for 10 minutes, followed by a high speed centrifugation of the supernatants at 100,000×g for 60 minutes to pellet the SMP. The supernatant was decanted and the SMP pellet was rinsed with Mito B buffer and then resuspended in the same buffer.

Figure 12:
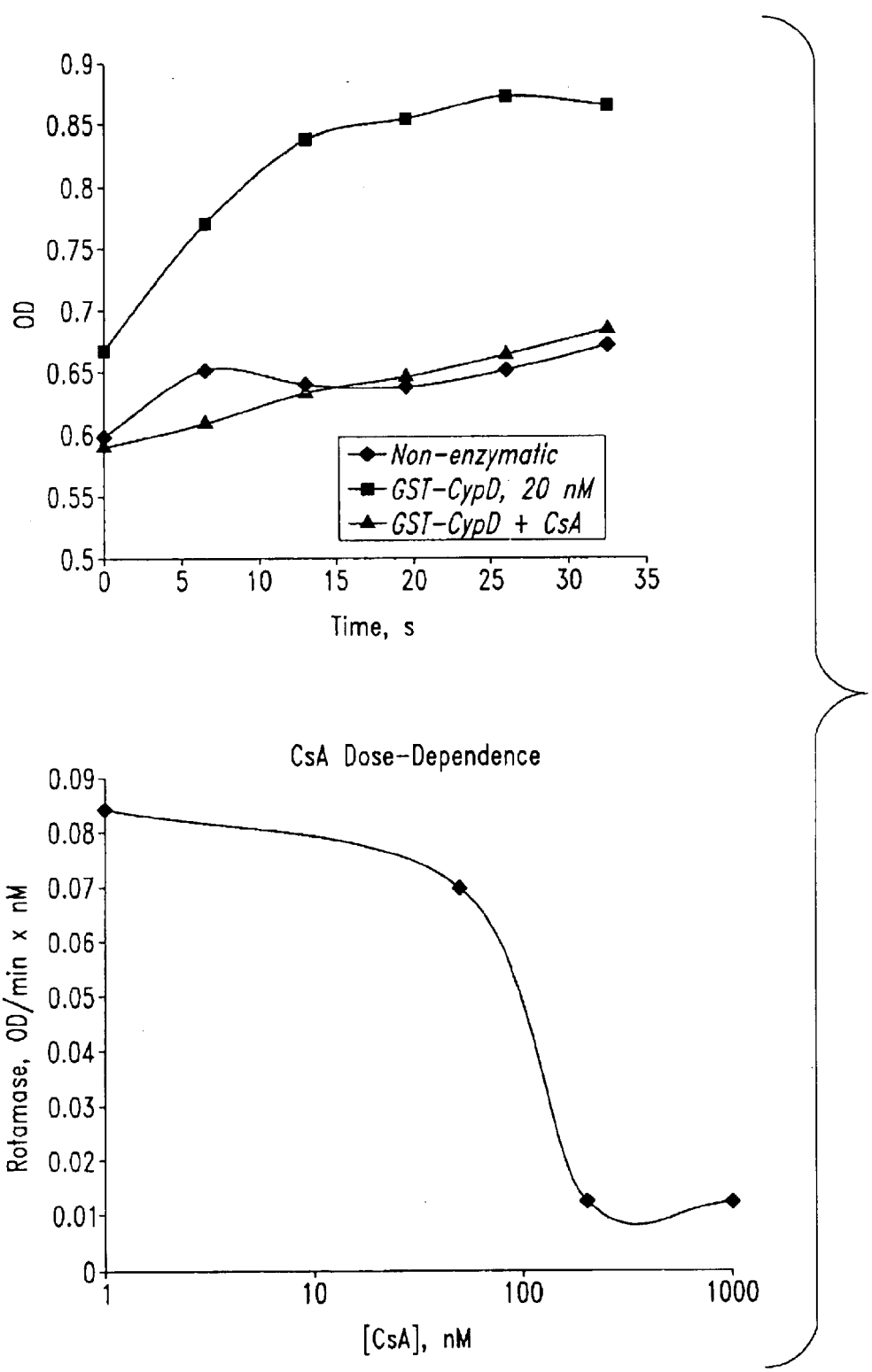
FIG. 12 shows rotamase activity of GST-CypD fusion proteins.
Figure 13:
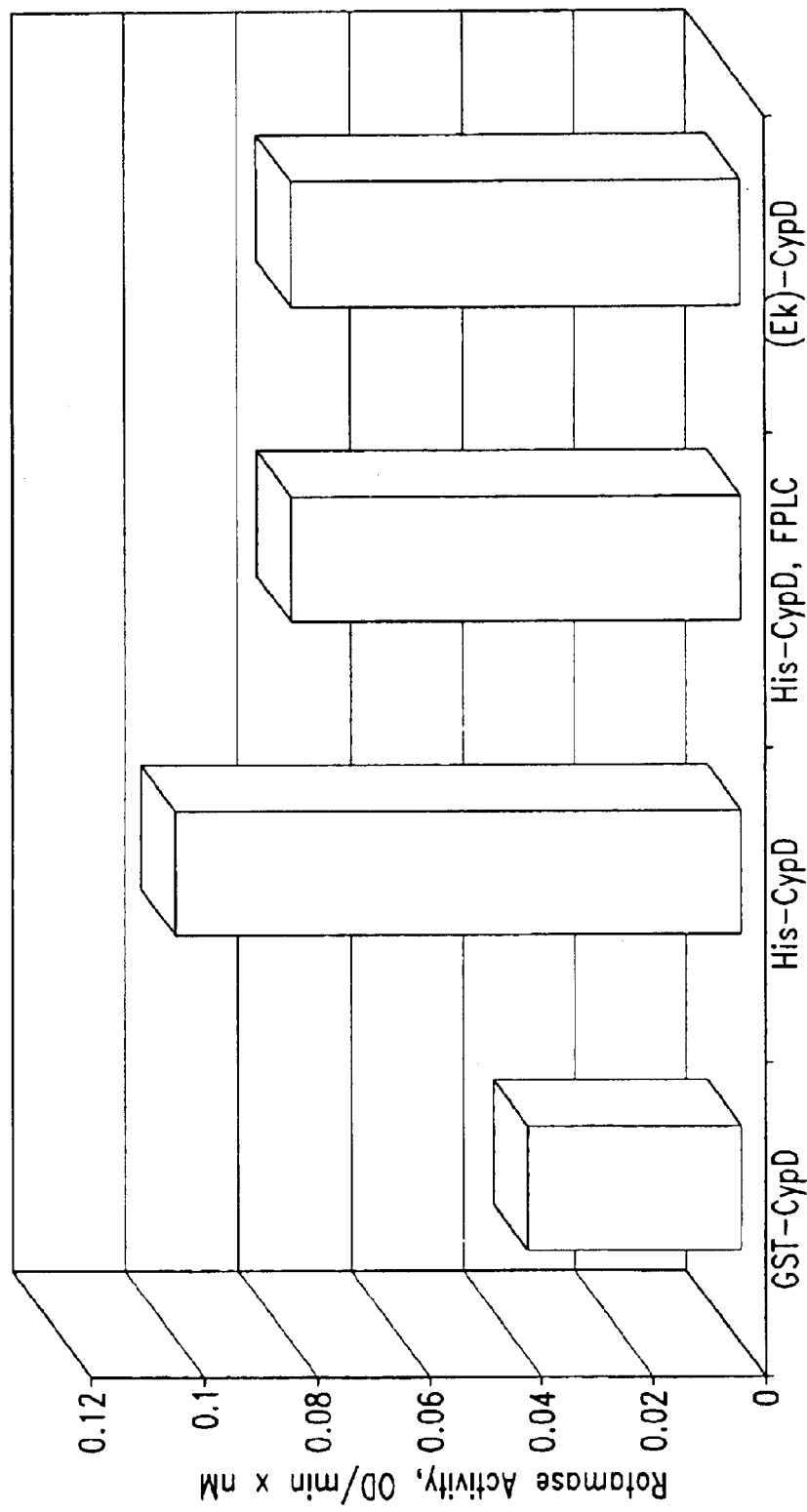
FIG. 13 shows rotamase activities of GST-Cyp and, His-CypD fusion proteins, and or recombinant CypD recovered following enterokinase (Ek) cleaveage of CypD fusion protein.

Cyclophilin binding to ANT present in the SMP was determined using soluble recombinant GST-cyclophilin D (see Example 10, above). Rotamase (peptidylprolyl cis-trans isomerase) activity of the GST-CypD preparation was determined according to the "solvent jump" method of Kofron et al. (1991 *Biochemistry* 30: 6127–6134). Briefly, Ala-Ala-$_{cis/trans}$-Pro-Phe-pNa was used as the rotamase substrate, coupled with α-chymotrypsin cleavage of all trans-Pro containing peptide to yield p-nitroanilide, detected by absorbance at 390 nm. As shown in FIG. 12 (left panel), GST-CypD exhibited readily apparent rotamase activity relative to test reactions performed in the absence of added GST-CypD for purposes of determining non-enzymatic cis-to-trans isomerization of the substrate peptide. Cyclosporin A (CsA) inhibited the CypD rotamase activity (FIG. 12) in a dose-dependent manner (FIG. 12, right panel), further confirming the activity of the recombinant GST-CypD fusion protein. Using the same methodology, rotamase activity was also demonstrated for recombinant polyHis-tagged CypD fusion proteins (see Example 9), including His-CypD affinity purified on nickel columns as described above, His-CypD purified by fast protein liquid chromatography (FPLC™, Pharmacia, Piscataway, N.J.), and CypD liberated from the polyHis fusion tag following enterokinase cleavage (Ek-CypD); these data are shown in FIG. 13.

Figure 11:
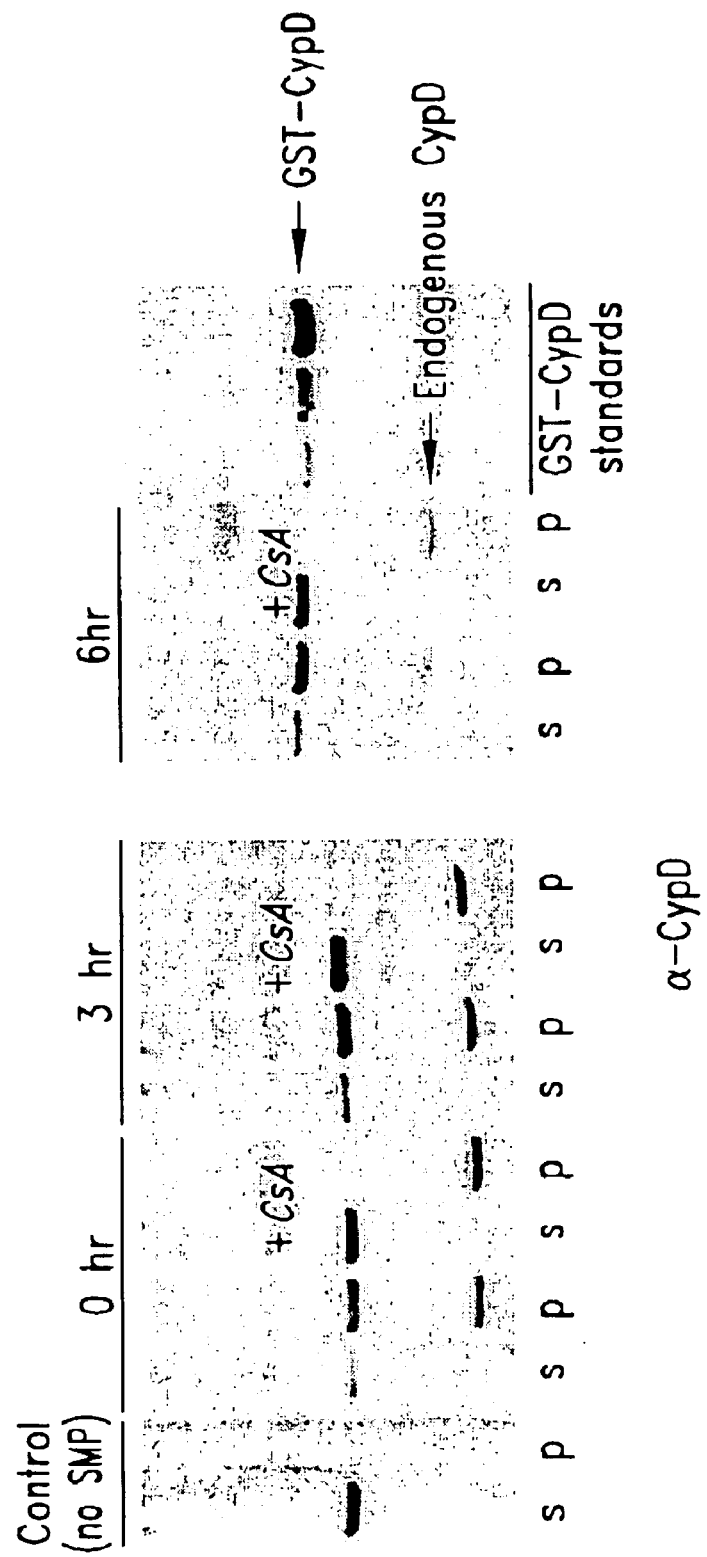
FIG. 11 shows western immunoblot analysis of the stability of GST-CypD binding to huANT3containing *T. ni* cell submitochondrial particles, using anti-CypD antibody for detection. CsA, cyclosporin A; s, supernatant; p, pellet.

To assay binding of cyclophilins to the SMP prepared from *T. ni* cells, binding reactions were set up in polycarbonate centrifuge tubes containing 1 mg SMP and 2.6 µM GST-cyclophilin D (Example 10) in a final volume of 1 ml binding buffer (50 mM NaCl; 20 mM imidazole; 10 mM HEPES pH 7.2; 10 mM $K_2HPO_4$; 1 mM EDTA). For certain reactions, 10 µM cyclosporin A (CsA) was also present. To assess the stability of the reaction components, GST-CypD and SMP were either (i) combined immediately following preparation of the SMP (FIG. 11, 0 hr), or (ii) held at 4° C. for 3–6 hours (FIG. 11, 3 hr and 6 hr) prior to initiation of the binding assay. Binding reaction mixtures were incubated at room temperature for 20 min, placed in a centrifuge rotor that had been pre-cooled to 15° C. and then centrifuged at 100,000×g for 60 min to pellet the SMP. Pellets were solubilized overnight at 37° C. in SDS-PAGE sample buffer, and protein determinations were performed as described above on aliquots of the dissolved pellets, and of the supernatants. Pellet and supernatant samples corresponding to equivalent ligand (GST-CypD) concentrations were electrophoresed on SDS-polyacrylamide gels and blot transferred to nitrocellulose according to standard procedures. SMP-bound CypD present in the pellets, and unbound (free) CypD present in the supernatants, were determined by western immunoblot analysis as described above, except using as a source of primary antibodies rabbit antisera containing CypD-specific antibodies generated by immunization with a CypD peptide according to the method of Bergsma et al. (1991 *J. Biol. Chem.* 266:23204). FIG. 11 shows the results of the western blot analysis, where no CypD was detected in the pellet (p) fraction of a control sample to which no SMP were added, but CypD was readily detected in the supernatant (s) fraction of this control sample. When SMP were added to GST-CypD immediately after preparation (0 hr), or after 3–6 hours (3 hr, 6 hr), GST-CypD was readily detectable in SMP pellet fractions in a CsA-inhibited manner.

Example 20
Assay for CypD-ANT Binding Interactions Using Proteoliposomes This example describes compositions and methods for assaying CypD binding to proteoliposomes (PLS) prepared from lipids reconstituted with bacteriorhodopsin (BR) and/or recombinant human ANT3 mitochondria derived from *T. ni* cells expressing His-tagged recombinant human ANT3 (see Examples 3 and 15 above). Inclusion of BR in the reconstituted liposomes provided density and a source of visible color to facilitate proteoliposome isolation, and also provided a non-specific control for protein-protein binding.

Reconstitution of purified ANT into liposomes was performed based on the methods of fast detergent removal using adsorbent beads (Kramer et al., 1986 *Biochim. Biophys. Acta,* 863, 289–286) and of formation of relatively large, unilamellar liposomes using nonionic detergents (Ueno et al., 1984 *Biochemistry,* 23, 3070–3076), which have been modified to accelerate the process of proteoliposome formation and to minimize loss of lipids by adsorption to the beads. Preformed liposomes were prepared by a freeze/thaw/sonication procedure. Briefly, egg-yolk lecithin (240 mg) was suspended in 3 ml of reconstitution buffer (50 mM NaCl, 10 mM HEPES, pH 7.4). The suspension was pulsed with argon stream to remove oxygen, partially frozen by contacting the vessel with a dry ice/ethanol bath, and sonicated as described above for SMP except the sonication period was for 1 min. The freeze/sonication step was repeated at least 3–4 times until clarification of lipid suspension was achieved.

Small EconoColumns™ (BioRad, Hercules, Calif.) were filled with 1.7 gm of SM-2 BioBeads™ (BioRad), washed with methanol followed by water, and equilibrated with the reconstitution buffer. Elution buffer (50 mM NaCl, 1 mM EDTA, 10 mM Hepes, 1.3% Triton X-100™, 0.5 ml) containing His-tagged, affinity purified recombinant human ANT3 was mixed with 200 µl of preformed liposomes, and then either ATP (50 mM) or methylumbelliferone phosphate (MUP, 5 mM, Molecular Probes, Inc., Eugene, Oreg.) was added. Control (protein-free) liposomes were prepared in parallel by adding 0.5 ml of the elution buffer (50 mM NaCl, 1 mM EDTA, 10 mM Hepes, 1.3% Triton X-100™) to 200 µl of the liposome suspension. Each mixture was vortexed, applied to the BioBeads™ SM-2 column and passed through the column 5–6 times. Formation of proteoliposomes was visualized by apparent turbidity of the solution. Non-entrapped MUP or ATP was removed either during pelleting of the proteoliposomes by centrifugation, or by filtration of the proteoliposome suspension on a column of Sephadex™ G-50 (Pharmacia, Piscataway, N.J.).

Bacteriorhodopsin (BR) was co-reconstituted into the ANT liposomes as follows. Bacteriorhodopsin (5 mg, Sigma, St Louis, Mo.) was monomerized by preincubation for 6 hr on a rotator in 200 µl of elution buffer (containing 1.3%Triton). The monomeric protein was added to the ANT-lipid mixture following addition of ANT to lipids as described above, but prior to the addition of ATP or MUP.

Integrity of liposomes and proteoliposomes integrity was evaluated by determining retention of encapsulated MUP (Molecular Probes) according to the supplier's instructions. Briefly, fluorescent detection of methylumbelliferyl anion, an alkaline phosphatase cleavage product o MUP, was monitored in aliquots of liposomes and proteoliposomes exposed to alkaline phosphatase. Integrity of liposomes and proteoliposomes was also evaluated by determining liposomal permeability detectable as efflux of entrapped ATP using a coupled hexokinase and glucose-6-phosphate dehydrogenase system as described (Streicher-Scott et al., 1993 *Anal. Biochem.* 210, 69–76) with fluorimetric detection of NADPH. Using these procedures no loss of entrapped indicators from liposomes or proteoliposomes was detected.

Assays for detection of GST-CypD binding to liposomes or proteoliposomes were performed essentially as described above in Example 19, but substituting liposomes (LS) or proteoliposomes (PLS) for SMP with the following additional modifications: The reaction buffer for the binding assay was 5 mM K2HPO4, 10 mM HEPES pH 7.2; each binding reaction contained 200 µl of a LS or PLS suspension prepared as described above, and pelleting LS and PLS required centrifugation at 140,000×g.

Figure 14:
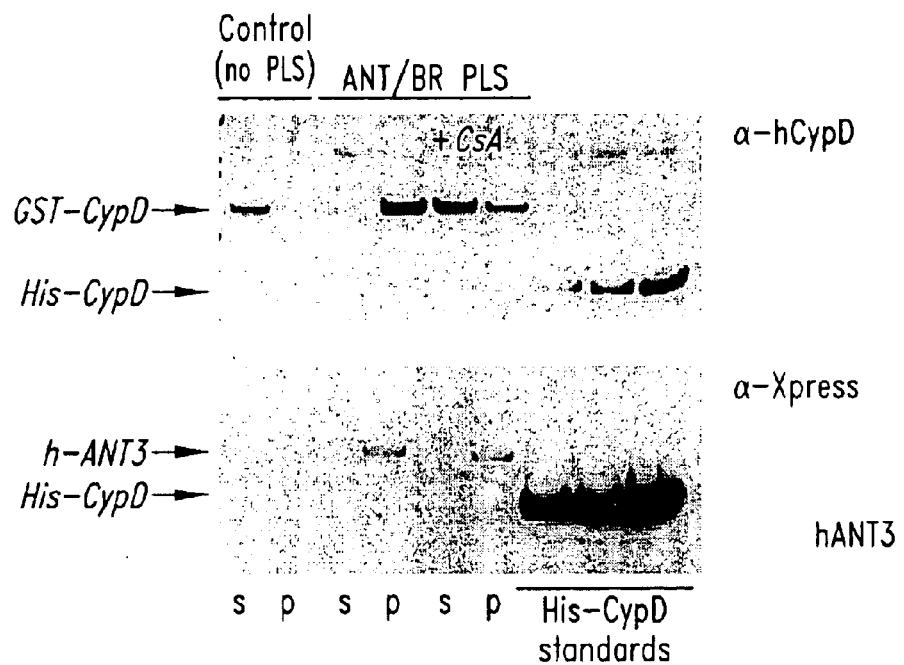
FIG. 14 shows western immunoblot analysis of GST-CypD binding to proteoliposomes reconstituted with huANT3 and bacteriorhodopsin.
Figure 15:
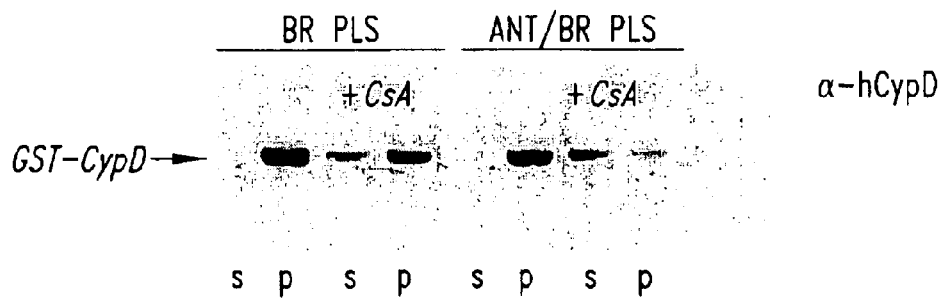
FIG. 15 shows western immunoblot analysis of GST-CypD binding to proteoliposomes reconstituted with bacteriorhodopsin (BR PLS) or with huANT3 and bacteriorhodopsin (ANT/BR).

FIG. 14 shows western blot analysis in which binding of GST-CypD to PLS reconstituted with both human ANT3 and bacteriorhodopsin was readily apparent. The upper panel of FIG. 14 shows a western blot developed with anti-human CypD antibodies as described in the preceding Example, wherein CypD remained in the supernatant when no PLS were added (left-most lane), but a pronounced CypD signal appeared in the ANT/BR PLS pellet when PLS were added without detectable signal in the corresponding supernatant fraction. As also shown in FIG. 14, in the presence of CsA the distribution of CypD was altered, with a readily detectable signal remaining in the supernatant. The lower panel of FIG. 14 shows the same western blot developed with a monoclonal antibody specific for the Express™ epitope tag engineered into the huANT3 construct, as described above. To further characterize the specificity of CsA inhibition of the CypD-ANT3 binding interaction, binding assays were conducted comparing CypD binding to PLS reconstituted with either BR only, or with both BR and ANT. As shown in FIG. 15, GST-CypD binding to ANT/BR PLS was readily detectable and was inhibited by CsA, which effected a pronounced reduction of detectable CypD in the ANT/BR PLS pellet (FIG. 15, right-hand four lanes) but did not appear to do so from the BR PLS pellet (FIG. 15, fourth lane from left).

As an alternative to the ANT/CypD binding assays described above, which feature centrifugation of PLS to identify binding interactions, a "spin-dialysis" method was also developed. This assay permitted determination of binding interactions with protein-free liposomes (LS) as well as PLS, since it did not require the added density conferred upon PLS by reconstitution with proteins, which, as noted above, facilitated PLS recovery by ultracentrifugation. The spin-dialysis assay method for determining CypD-ANT binding was performed as follows.

An aliquot (100 µl) of each liposome preparation (e.g., LS, BR PLS, ANT/BR PLS) prepared as described above was mixed with 10 µg of GST-CypD and diluted with 400 µl of standard buffer (50 mM NaCl, 10 mM Hepes, pH 7.4). Control (liposome-free) samples contained 500 µl of the buffer and 10 µg of GST-CypD. All samples were incubated on a rotator for 20 min at room temperature, and were then individually transferred into Amicon (Beverly, Mass.) microncentrator tubes with 100 kDa molecular weight cutoff filters. The tubes were centrifuged (in a bucket rotor) at 4° C. according to the instructions provided by the manufacturer. The time of centrifugation was adjusted so that retentate volume would be about 40 µl in each tube, which varied among the samples. The control sample was centrifuged briefly (4 min), the samples containing protein-free liposomes, BR liposomes, and ANT/BR liposomes were centrifuged for 55, 65, and 75 min. respectively. Both flow-through solutions (containing free CypD ligand) and retentates containing concentrated liposomes (e.g., with bound ligand) or buffer alone (control) were tested for CypD content by western blot analysis using anti-CypD antibodies as described above. To rule out the possibility that CypD was being lost from samples by adsorption to the concentrator filters, the filters were washed with 90 µl of a diluted SDS-sample buffer and the wash analyzed for CypD by western immunoblotting. No CypD was detected in the wash, indicating an apparent absence of CypD binding to the filters.

From the foregoing it will be appreciated that, although specific embodiments of the invention have been described herein for purposes of illustration, various modifications may be made without deviating from the spirit and scope of the invention. Accordingly, the invention is not limited except as by the appended claims.

```
[\]m                        SEQUENCE LISTING

<160> NUMBER OF SEQ ID NOS: 57

<210> SEQ ID NO 1
<211> LENGTH: 894
<212> TYPE: DNA
<213> ORGANISM: Homo sapien

<400> SEQUENCE: 1
atgggtgatc acgcttggag cttcctaaag gacttcctgg ccggggcggt cgccgctgcc      60
gtctccaaga ccgcggtcgc ccccatcgag agggtcaaac tgctgctgca ggtccagcat     120
gccagcaaac agatcagtgc tgagaagcag tacaaaggga tcattgattg tgtggtgaga     180
atccctaagg agcagggctt cctctccttc tggagcggta acctggccaa cgtgatccgt     240
tacttcccca cccaagctct caacttcgcc ttcaaggaca agtacaagca gctcttctta     300
gggggtgtgg atcggcataa gcagttctgg cgctactttg ctggtaacct ggcgtccggt     360
ggggccgctg gggccacctc cctttgcttt gtctacccgc tggactttgc taggaccagg     420
ttggctgctg atgtgggcag gcgcgcccag cgtgagttcc atggtctggg cgactgtatc     480
atcaagatct tcaagtctga tggcctgagg gggctctacc agggtttcaa cgtctctgtc     540
caaggcatca ttatctatag agctgcctac ttcggagtct atgatactgc caaggggatg     600
ctgcctgacc ccaagaacgt gcacattttt gtgagctgga tgattgccca gagtgtgacg     660
gcagtcgcag ggctgctgtc ctacccgttt gacactgttc gtcgtagaat gatgatgcag     720
tccggccgga aggggccgga tattatgtac acggggacag ttgactgctg gaggaagatt     780
gcaaaagacg aaggagccaa ggccttcttc aaaggtgcct ggtccaatgt gctgagaggc     840
atgggcggtc cttttgtatt ggtgttgtat gatgagatca aaaaatatgt ctaa           894

<210> SEQ ID NO 2
<211> LENGTH: 897
<212> TYPE: DNA
<213> ORGANISM: Homo sapien

<400> SEQUENCE: 2
atgacagatg ccgcattgtc cttcgccaag gacttcctgg caggtggagt ggccgcagcc      60
atctccaaga cggcggtagc gcccatcgag cgggtcaagc tgctgctgca ggtgcagcat     120
gccagcaagc agatcactgc agataagcaa tacaaaggca ttatagactg cgtggtccgt     180
attcccaagg agcaggaagt tctgtccttc tggcgcggta acctggccaa tgtcatcaga     240
tacttcccca cccaggctct taacttcgcc ttcaaagata aatacaagca gatcttcctg     300
ggtggtgtgg acaagagaac ccagttttgg cgctactttg cagggaatct ggcatcgggt     360
ggtgccgcag gggccacatc cctgtgtttt gtgtaccctc ttgattttgc ccgtacccgt     420
ctagcagctg atgtgggtaa agctggagct gaaagggaat tccgaggcct cggtgactgc     480
ctggttaaga tctacaaatc tgatgggatt aagggcctgt accaaggctt taacgtgtct     540
gtgcagggta ttatcatcta ccgagccgcc tacttcggta tctatgacac tgcaagggga     600
atgcttccgg atcccaagaa cactcacatc gtcatcagct ggatgatcgc acagactgtc     660
actgctgttt ccgggttgac ttcctatcca tttgacaccg ttcgccgccg catgatgatg     720
cagtcagggc gcaaaggaac tgacatcatg tacacaggca cgcttgactg ctggcggaag     780
```

```
attgctcgtg atgaaggagg caaagctttt ttcaagggtg catggtccaa tgttctcaga    840
ggcatgggtg gtgcttttgt gcttgtcttg tatgatgaaa tcaagaagta cacataa       897
```

<210> SEQ ID NO 3
<211> LENGTH: 897
<212> TYPE: DNA
<213> ORGANISM: Homo sapiens

<400> SEQUENCE: 3

```
atgacggaac aggccatctc cttcgccaaa gacttcttgg ccggaggcat cgccgccgcc    60
atctccaaga cggccgtggc tccgatcgag cgggtcaagc tgctgctgca ggtccagcac   120
gccagcaagc agatcgccgc cgacaagcag tacaagggca tcgtggactg cattgtccgc   180
atccccaagg agcagggcgt gctgtccttc tggagggca accttgccaa cgtcattcgc    240
tacttcccca ctcaagccct caacttcgcc ttcaaggata gtacaagca gatcttcctg     300 gggggcgtgg acaagcacac gcagttctgg aggtactttg cgggcaacct ggcctccggc   360
ggtgcggccg gcgcgacctc cctctgcttc gtgtacccgc tggattttgc cagaacccgc   420
ctggcagcga acgtgggaaa gtcaggcaca gagcgcgagt tccgaggcct gggagactgc   480
ctggtgaaga tcaccaagtc cgacggcatc cggggcctgt accagggctt cagtgtctcc   540
gtgcagggca tcatcatcta ccgggcggcc tacttcggcg tgtacgatac ggccaagggc   600
atgctccccg accccaagaa cacgcacatc gtggtgagct ggatgatcgc gcagaccgtg   660
acggccgtgg ccggcgtggt gtcctacccc ttcgacacgt gcggcggcg catgatgatg   720 cagtccgggc gcaaaggagc tgacatcatg tacacgggca ccgtcgactg ttggaggaag   780
atcttcagag atgaggggg caaggccttc ttcaaggtg cgtggtccaa cgtcctgcgg    840 ggcatgggg gcgccttcgt gctggtcctg tacgacgagc tcaagaaggt gatctaa       897
```

<210> SEQ ID NO 4
<211> LENGTH: 43
<212> TYPE: DNA
<213> ORGANISM: Artificial Sequence
<220> FEATURE:
<223> OTHER INFORMATION: PCR Primer

<400> SEQUENCE: 4

```
ttatatctcg agtatgggtg atcacgcttg gagcttccta aag                      43
```

<210> SEQ ID NO 5
<211> LENGTH: 43
<212> TYPE: DNA
<213> ORGANISM: Artificial Sequence
<220> FEATURE:
<223> OTHER INFORMATION: PCR Primer

<400> SEQUENCE: 5

```
tataggta ccttagacat attttttgat ctcatcatac aac                        43
```

<210> SEQ ID NO 6
<211> LENGTH: 43
<212> TYPE: DNA
<213> ORGANISM: Artificial Sequence
<220> FEATURE:
<223> OTHER INFORMATION: PCR Primer

<400> SEQUENCE: 6

```
ttatatctcg agtatgacag atgccgctgt gtccttcgcc aag                      43
```

<210> SEQ ID NO 7
<211> LENGTH: 43
<212> TYPE: DNA
<213> ORGANISM: Artificial Sequence
<220> FEATURE:
<223> OTHER INFORMATION: PCR Primer

<400> SEQUENCE: 7
tatataggta ccttatgtgt acttcttgat tcatcatac aag                43

<210> SEQ ID NO 8
<211> LENGTH: 43
<212> TYPE: DNA
<213> ORGANISM: Artificial Sequence
<220> FEATURE:
<223> OTHER INFORMATION: PCR Primer

<400> SEQUENCE: 8
ttatatctcg agtatgacgg aacaggccat ctccttcgcc aaa                43

<210> SEQ ID NO 9
<211> LENGTH: 44
<212> TYPE: DNA
<213> ORGANISM: Artificial Sequence
<220> FEATURE:
<223> OTHER INFORMATION: PCR Primer

<400> SEQUENCE: 9
tatataggta ccttagagtc accttcttga gctcgtcgta cagg               44

<210> SEQ ID NO 10
<211> LENGTH: 21
<212> TYPE: DNA
<213> ORGANISM: Artificial Sequence
<220> FEATURE:
<223> OTHER INFORMATION: PCR Primer

<400> SEQUENCE: 10
tatgccatag catttttatc c                                        21

<210> SEQ ID NO 11
<211> LENGTH: 18
<212> TYPE: DNA
<213> ORGANISM: Artificial Sequence
<220> FEATURE:
<223> OTHER INFORMATION: PCR Primer

<400> SEQUENCE: 11
cgccaaaaca gccaagct                                            18

<210> SEQ ID NO 12
<211> LENGTH: 45
<212> TYPE: DNA
<213> ORGANISM: Artificial Sequence
<220> FEATURE:
<223> OTHER INFORMATION: Mutagenic oligonucleotide primer

<400> SEQUENCE: 12
ggagatggcc tgttccgtca tcttatcgtc atcgtcgtac agatc              45

<210> SEQ ID NO 13
<211> LENGTH: 45
<212> TYPE: DNA
<213> ORGANISM: Artificial Sequence
<220> FEATURE:
<223> OTHER INFORMATION: Mutagenic oligonucleotide primer

```
<400> SEQUENCE: 13
gatctgtacg acgatgacga taagatgacg aacaggcca tctcc            45

<210> SEQ ID NO 14
<211> LENGTH: 35
<212> TYPE: DNA
<213> ORGANISM: Artificial Sequence
<220> FEATURE:
<223> OTHER INFORMATION: PCR Primer

<400> SEQUENCE: 14
cccggggaat tctgatgacg aacaggcca tctcc                       35

<210> SEQ ID NO 15
<211> LENGTH: 34
<212> TYPE: DNA
<213> ORGANISM: Artificial Sequence
<220> FEATURE:
<223> OTHER INFORMATION: PCR Primer

<400> SEQUENCE: 15
cccgggctcg agttagagtc accttcttga gctc                       34

<210> SEQ ID NO 16
<211> LENGTH: 41
<212> TYPE: DNA
<213> ORGANISM: Artificial Sequence
<220> FEATURE:
<223> OTHER INFORMATION: PCR Primer

<400> SEQUENCE: 16
ttataggatc catgacggaa caggccatct ccttcgccaa a               41

<210> SEQ ID NO 17
<211> LENGTH: 41
<212> TYPE: DNA
<213> ORGANISM: Artificial Sequence
<220> FEATURE:
<223> OTHER INFORMATION: PCR Primer

<400> SEQUENCE: 17
ttaaagaatt cttagatcac cttcttgagc tcgtcgtaca g               41

<210> SEQ ID NO 18
<211> LENGTH: 18
<212> TYPE: DNA
<213> ORGANISM: Artificial Sequence
<220> FEATURE:
<223> OTHER INFORMATION: Sequencing primer

<400> SEQUENCE: 18
aaatgataac catctcgc                                         18

<210> SEQ ID NO 19
<211> LENGTH: 18
<212> TYPE: DNA
<213> ORGANISM: Artificial Sequence
<220> FEATURE:
<223> OTHER INFORMATION: Sequencing primer

<400> SEQUENCE: 19
acttcaagga gaatttcc                                         18

<210> SEQ ID NO 20
```

```
<211> LENGTH: 18
<212> TYPE: DNA
<213> ORGANISM: Artificial Sequence
<220> FEATURE:
<223> OTHER INFORMATION: Sequencing primer

<400> SEQUENCE: 20
acttcgcctt cacggata                                                 18

<210> SEQ ID NO 21
<211> LENGTH: 18
<212> TYPE: DNA
<213> ORGANISM: Artificial Sequence
<220> FEATURE:
<223> OTHER INFORMATION: Sequencing primer

<400> SEQUENCE: 21
tacggccaag ggcattct                                                 18

<210> SEQ ID NO 22
<211> LENGTH: 18
<212> TYPE: DNA
<213> ORGANISM: Artificial Sequence
<220> FEATURE:
<223> OTHER INFORMATION: Sequencing primer

<400> SEQUENCE: 22
tgaagcggaa gttcctat                                                 18

<210> SEQ ID NO 23
<211> LENGTH: 18
<212> TYPE: DNA
<213> ORGANISM: Artificial Sequence
<220> FEATURE:
<223> OTHER INFORMATION: Sequencing primer

<400> SEQUENCE: 23
atgccggttc ccgtacga                                                 18

<210> SEQ ID NO 24
<211> LENGTH: 31
<212> TYPE: DNA
<213> ORGANISM: Artificial Sequence
<220> FEATURE:
<223> OTHER INFORMATION: Mutagenic oligonucleotide primer

<400> SEQUENCE: 24
ggcctgttcc gtcatcttat cgtcatcgtc g                                  31

<210> SEQ ID NO 25
<211> LENGTH: 31
<212> TYPE: DNA
<213> ORGANISM: Artificial Sequence
<220> FEATURE:
<223> OTHER INFORMATION: Mutagenic oligonucleotide primer

<400> SEQUENCE: 25
cgacgatgac gataagatga cggaacaggc c                                  31

<210> SEQ ID NO 26
<211> LENGTH: 498
<212> TYPE: DNA
<213> ORGANISM: Homo sapien
<220> FEATURE:
<221> NAME/KEY: CDS
<222> LOCATION: (1)...(495)
```

```
<400> SEQUENCE: 26 atg gtc aac ccc acc gtg ttc ttc gac att gcc gtc gac ggc gag ccc      48
Met Val Asn Pro Thr Val Phe Phe Asp Ile Ala Val Asp Gly Glu Pro
 1               5                  10                  15 ttg ggc cgc gtc tcc ttt gag ctg ttt gca gac aag gtc cca aag aca      96
Leu Gly Arg Val Ser Phe Glu Leu Phe Ala Asp Lys Val Pro Lys Thr
             20                  25                  30 gca gaa aat ttt cgt gct ctg agc act gga gag aaa gga ttt ggt tat     144
Ala Glu Asn Phe Arg Ala Leu Ser Thr Gly Glu Lys Gly Phe Gly Tyr
         35                  40                  45 aag ggt tcc tgc ttt cac aga att att cca ggg ttt atg tgt cag ggt     192
Lys Gly Ser Cys Phe His Arg Ile Ile Pro Gly Phe Met Cys Gln Gly
     50                  55                  60 ggt gac ttc aca cgc cat aat ggc act ggt ggc aag tcc atc tat ggg     240
Gly Asp Phe Thr Arg His Asn Gly Thr Gly Gly Lys Ser Ile Tyr Gly
 65                  70                  75                  80 gag aaa ttt gaa gat gag aac ttc atc cta aag cat acg ggt cct ggc     288
Glu Lys Phe Glu Asp Glu Asn Phe Ile Leu Lys His Thr Gly Pro Gly
                 85                  90                  95 atc ttg tcc atg gca aat gct gga ccc aac aca aat ggt tcc cag ttt     336
Ile Leu Ser Met Ala Asn Ala Gly Pro Asn Thr Asn Gly Ser Gln Phe
            100                 105                 110 ttc atc tgc act gcc aag act gag tgg ttg gat ggc aag cat gtg gtg     384
Phe Ile Cys Thr Ala Lys Thr Glu Trp Leu Asp Gly Lys His Val Val
        115                 120                 125 ttt ggc aaa gtg aaa gaa ggc atg aat att gtg gag gcc atg gag cgc     432
Phe Gly Lys Val Lys Glu Gly Met Asn Ile Val Glu Ala Met Glu Arg
    130                 135                 140 ttt ggg tcc agg aat ggc aag acc agc aag aag atc acc att gct gac     480
Phe Gly Ser Arg Asn Gly Lys Thr Ser Lys Lys Ile Thr Ile Ala Asp
145                 150                 155                 160 tgt gga caa ctc gaa taa                                              498
Cys Gly Gln Leu Glu
                165

<210> SEQ ID NO 27
<211> LENGTH: 165
<212> TYPE: PRT
<213> ORGANISM: Homo sapien

<400> SEQUENCE: 27

Met Val Asn Pro Thr Val Phe Phe Asp Ile Ala Val Asp Gly Glu Pro
 1               5                  10                  15

Leu Gly Arg Val Ser Phe Glu Leu Phe Ala Asp Lys Val Pro Lys Thr
             20                  25                  30

Ala Glu Asn Phe Arg Ala Leu Ser Thr Gly Glu Lys Gly Phe Gly Tyr
         35                  40                  45

Lys Gly Ser Cys Phe His Arg Ile Ile Pro Gly Phe Met Cys Gln Gly
     50                  55                  60

Gly Asp Phe Thr Arg His Asn Gly Thr Gly Gly Lys Ser Ile Tyr Gly
 65                  70                  75                  80

Glu Lys Phe Glu Asp Glu Asn Phe Ile Leu Lys His Thr Gly Pro Gly
                 85                  90                  95

Ile Leu Ser Met Ala Asn Ala Gly Pro Asn Thr Asn Gly Ser Gln Phe
            100                 105                 110

Phe Ile Cys Thr Ala Lys Thr Glu Trp Leu Asp Gly Lys His Val Val
        115                 120                 125

Phe Gly Lys Val Lys Glu Gly Met Asn Ile Val Glu Ala Met Glu Arg
```

```
              130                 135                 140
Phe Gly Ser Arg Asn Gly Lys Thr Ser Lys Lys Ile Thr Ile Ala Asp
145                 150                 155                 160

Cys Gly Gln Leu Glu
                165
```

<210> SEQ ID NO 28
<211> LENGTH: 42
<212> TYPE: DNA
<213> ORGANISM: Artificial Sequence
<220> FEATURE:
<223> OTHER INFORMATION: PCR primer

<400> SEQUENCE: 28
ttaatgggta ccatgacgga acaggccatc tccttcgcca aa                              42

<210> SEQ ID NO 29
<211> LENGTH: 42
<212> TYPE: DNA
<213> ORGANISM: Artificial Sequence
<220> FEATURE:
<223> OTHER INFORMATION: PCR primer

<400> SEQUENCE: 29
ttatactcga gttagatcac cttcttgagc tcgtcgtaca gg                              42

<210> SEQ ID NO 30
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 30

```
Cys Trp Arg Lys Ile Phe Arg Asp Glu Gly Gly Lys Ala Phe Phe
 1               5                  10                  15
```

<210> SEQ ID NO 31
<211> LENGTH: 41
<212> TYPE: DNA
<213> ORGANISM: Artificial Sequence
<220> FEATURE:
<223> OTHER INFORMATION: Primer for PCR amplification of human ANT3 for
      expression construct

<400> SEQUENCE: 31
ttaatggtac catgacggaa caggccatct ccttcgccaa a                               41

<210> SEQ ID NO 32
<211> LENGTH: 42
<212> TYPE: DNA
<213> ORGANISM: Artificial Sequence
<220> FEATURE:
<223> OTHER INFORMATION: Primer for PCR amplification of human ANT3 for
      expression constructs

<400> SEQUENCE: 32
ttatactcga gttagatcac cttcttgagc tcgtcgtaca gg                              42

<210> SEQ ID NO 33
<211> LENGTH: 30
<212> TYPE: DNA
<213> ORGANISM: Artificial Sequence
<220> FEATURE:
<223> OTHER INFORMATION: Primer for PCR amplification of EYFP -continued

```
<400> SEQUENCE: 33
gggcccctcg agatggtgag caagggcgag                                    30

<210> SEQ ID NO 34
<211> LENGTH: 33
<212> TYPE: DNA
<213> ORGANISM: Artificial Sequence
<220> FEATURE:
<223> OTHER INFORMATION: Primer for PCR amplification of EYFP

<400> SEQUENCE: 34
gggccctcta gactacttgt acagctcgtc cat                                33

<210> SEQ ID NO 35
<211> LENGTH: 34
<212> TYPE: DNA
<213> ORGANISM: Artificial Sequence
<220> FEATURE:
<223> OTHER INFORMATION: PCR primer

<400> SEQUENCE: 35
tttaaactcg agtatggtca accccaccgt gttc                               34

<210> SEQ ID NO 36
<211> LENGTH: 35
<212> TYPE: DNA
<213> ORGANISM: Artificial Sequence
<220> FEATURE:
<223> OTHER INFORMATION: PCR Primer

<400> SEQUENCE: 36
tatataggta ccttattcga gttgtccaca gtcag                              35

<210> SEQ ID NO 37
<211> LENGTH: 31
<212> TYPE: DNA
<213> ORGANISM: Artificial Sequence
<220> FEATURE:
<223> OTHER INFORMATION: PCR Primer

<400> SEQUENCE: 37
ttaaggatcc atggtcaacc ccaccgtgtt c                                  31

<210> SEQ ID NO 38
<211> LENGTH: 33
<212> TYPE: DNA
<213> ORGANISM: Artificial Sequence
<220> FEATURE:
<223> OTHER INFORMATION: PCR primer

<400> SEQUENCE: 38
atatctcgag ttattcgagt tgtccacagt cag                                33

<210> SEQ ID NO 39
<211> LENGTH: 624
<212> TYPE: DNA
<213> ORGANISM: Homo sapien
<220> FEATURE:
<221> NAME/KEY: CDS
<222> LOCATION: (1)...(621)

<400> SEQUENCE: 39 atg ctg gcg ctg cgc tgc ggc tcc cgc tgg ctc ggc ctg ctc tcc gtc    48
Met Leu Ala Leu Arg Cys Gly Ser Arg Trp Leu Gly Leu Leu Ser Val
 1               5                  10                  15
```

| | | |
|---|---|---|
| ccg cgc tcc gtg ccg ctg cgc ctc ccc gcg gcc cgc gcc tgc agc aag<br>Pro Arg Ser Val Pro Leu Arg Leu Pro Ala Ala Arg Ala Cys Ser Lys<br>              20                        25                        30 | 96 |
| ggc tcc ggc gac ccg tcc tct tcc tcc tcc tcc ggg aac ccg ctc gtg<br>Gly Ser Gly Asp Pro Ser Ser Ser Ser Ser Ser Gly Asn Pro Leu Val<br>              35                        40                        45 | 144 |
| tac ctg gac gtg gac gcc aac ggg aag ccg ctc ggc cgc gtg gtg ctg<br>Tyr Leu Asp Val Asp Ala Asn Gly Lys Pro Leu Gly Arg Val Val Leu<br>  50                        55                        60 | 192 |
| gag ctg aag gca gat gtc gtc cca aag aca gct gag aac ttc aga gcc<br>Glu Leu Lys Ala Asp Val Val Pro Lys Thr Ala Glu Asn Phe Arg Ala<br>65                      70                        75                        80 | 240 |
| ctg tgc act ggt gag aag ggc ttc ggc tac aaa ggc tcc acc ttc cac<br>Leu Cys Thr Gly Glu Lys Gly Phe Gly Tyr Lys Gly Ser Thr Phe His<br>                    85                        90                        95 | 288 |
| agg gtg atc cct tcc ttc atg tgc cag gcg ggc gac ttc acc aac cac<br>Arg Val Ile Pro Ser Phe Met Cys Gln Ala Gly Asp Phe Thr Asn His<br>              100                      105                     110 | 336 |
| aat ggc aca ggc ggg aag tcc atc tac gga agc cgc ttt cct gac gag<br>Asn Gly Thr Gly Gly Lys Ser Ile Tyr Gly Ser Arg Phe Pro Asp Glu<br>            115                      120                     125 | 384 |
| aac ttt aca ctg aag cac gtg ggg cca ggt gtc ctg tcc atg gct aat<br>Asn Phe Thr Leu Lys His Val Gly Pro Gly Val Leu Ser Met Ala Asn<br>130                     135                       140 | 432 |
| gct ggt cct aac acc aac ggc tcc cag ttc ttc atc tgc acc ata aag<br>Ala Gly Pro Asn Thr Asn Gly Ser Gln Phe Phe Ile Cys Thr Ile Lys<br>145                     150                       155                     160 | 480 |
| aca gac tgg ttg gat ggc aag cat gtt gtg ttc ggt cac gtc aaa gag<br>Thr Asp Trp Leu Asp Gly Lys His Val Val Phe Gly His Val Lys Glu<br>            165                      170                     175 | 528 |
| ggc atg gac gtc gtg aag aaa ata gaa tct ttc ggc tct aag agt ggg<br>Gly Met Asp Val Val Lys Lys Ile Glu Ser Phe Gly Ser Lys Ser Gly<br>              180                      185                     190 | 576 |
| agg aca tcc aag aag att gtc atc aca gac tgt ggc cag ttg agc<br>Arg Thr Ser Lys Lys Ile Val Ile Thr Asp Cys Gly Gln Leu Ser<br>            195                      200                     205 | 621 |
| taa | 624 |

<210> SEQ ID NO 40
<211> LENGTH: 207
<212> TYPE: PRT
<213> ORGANISM: Homo sapien

<400> SEQUENCE: 40

Met Leu Ala Leu Arg Cys Gly Ser Arg Trp Leu Gly Leu Leu Ser Val
 1               5                  10                  15

Pro Arg Ser Val Pro Leu Arg Leu Pro Ala Ala Arg Ala Cys Ser Lys
            20                  25                  30

Gly Ser Gly Asp Pro Ser Ser Ser Ser Ser Ser Gly Asn Pro Leu Val
        35                  40                  45

Tyr Leu Asp Val Asp Ala Asn Gly Lys Pro Leu Gly Arg Val Val Leu
    50                  55                  60

Glu Leu Lys Ala Asp Val Val Pro Lys Thr Ala Glu Asn Phe Arg Ala
65                  70                  75                  80

Leu Cys Thr Gly Glu Lys Gly Phe Gly Tyr Lys Gly Ser Thr Phe His
                85                  90                  95

Arg Val Ile Pro Ser Phe Met Cys Gln Ala Gly Asp Phe Thr Asn His
            100                 105                 110

```
Asn Gly Thr Gly Gly Lys Ser Ile Tyr Gly Ser Arg Phe Pro Asp Glu
        115                 120                 125

Asn Phe Thr Leu Lys His Val Gly Pro Gly Val Leu Ser Met Ala Asn
130                 135                 140

Ala Gly Pro Asn Thr Asn Gly Ser Gln Phe Phe Ile Cys Thr Ile Lys
145                 150                 155                 160

Thr Asp Trp Leu Asp Gly Lys His Val Val Phe Gly His Val Lys Glu
                165                 170                 175

Gly Met Asp Val Val Lys Lys Ile Glu Ser Phe Gly Ser Lys Ser Gly
                180                 185                 190

Arg Thr Ser Lys Lys Ile Val Ile Thr Asp Cys Gly Gln Leu Ser
        195                 200                 205
```

<210> SEQ ID NO 41
<211> LENGTH: 31
<212> TYPE: DNA
<213> ORGANISM: Artificial Sequence
<220> FEATURE:
<223> OTHER INFORMATION: PCR primer

<400> SEQUENCE: 41
attaatctcg agtatgctgg cgctgcgctg c                                31

<210> SEQ ID NO 42
<211> LENGTH: 32
<212> TYPE: DNA
<213> ORGANISM: Artificial Sequence
<220> FEATURE:
<223> OTHER INFORMATION: PCR primer

<400> SEQUENCE: 42
tattaaggta ccttagctca actggccaca gt                               32

<210> SEQ ID NO 43
<211> LENGTH: 28
<212> TYPE: DNA
<213> ORGANISM: Artificial Sequence
<220> FEATURE:
<223> OTHER INFORMATION: PCR primer

<400> SEQUENCE: 43
ttatggatcc atgctggcgc tgcgctgc                                    28

<210> SEQ ID NO 44
<211> LENGTH: 30
<212> TYPE: DNA
<213> ORGANISM: Artificial Sequence
<220> FEATURE:
<223> OTHER INFORMATION: PCR primer

<400> SEQUENCE: 44
taatctcgag ttagctcaac tggccacagt                                  30

<210> SEQ ID NO 45
<211> LENGTH: 36
<212> TYPE: DNA
<213> ORGANISM: Artificial Sequence
<220> FEATURE:
<223> OTHER INFORMATION: PCR primer

<400> SEQUENCE: 45
gggcccctcg agcccgcgat gctggcgctg cgctgc                           36

-continued

```
<210> SEQ ID NO 46
<211> LENGTH: 32
<212> TYPE: DNA
<213> ORGANISM: Artificial Sequence
<220> FEATURE:
<223> OTHER INFORMATION: PCR primer

<400> SEQUENCE: 46
cccggtggat ccgcgctcaa ctggccacag tc                                    32

<210> SEQ ID NO 47
<211> LENGTH: 297
<212> TYPE: PRT
<213> ORGANISM: Homo sapien

<400> SEQUENCE: 47
```

Met Gly Asp His Ala Trp Ser Phe Leu Lys Asp Phe Leu Ala Gly Ala
 1               5                  10                  15

Val Ala Ala Val Ser Lys Thr Ala Val Pro Ile Glu Arg Val
            20                  25                  30

Lys Leu Leu Gln Val Gln His Ala Ser Lys Gln Ile Ser Ala Glu
        35                  40                  45

Lys Gln Tyr Lys Gly Ile Ile Asp Cys Val Val Arg Ile Pro Lys Glu
    50                  55                  60

Gln Gly Phe Leu Ser Phe Trp Arg Gly Asn Leu Ala Asn Val Ile Arg
65                  70                  75                  80

Tyr Phe Pro Thr Gln Ala Leu Asn Phe Ala Phe Lys Asp Lys Tyr Lys
                85                  90                  95

Gln Leu Phe Leu Gly Gly Val Asp Arg His Lys Gln Phe Trp Arg Tyr
            100                 105                 110

Phe Ala Gly Asn Leu Ala Ser Gly Gly Ala Ala Gly Ala Thr Ser Leu
        115                 120                 125

Cys Phe Val Tyr Pro Leu Asp Phe Ala Arg Thr Arg Leu Ala Ala Asp
    130                 135                 140

Val Gly Arg Arg Ala Gln Arg Glu Phe His Gly Leu Gly Asp Cys Ile
145                 150                 155                 160

Ile Lys Ile Phe Lys Ser Asp Gly Leu Arg Gly Leu Tyr Gln Gly Phe
                165                 170                 175

Asn Val Ser Val Gln Gly Ile Ile Ile Tyr Arg Ala Ala Tyr Phe Gly
            180                 185                 190

Val Tyr Asp Thr Ala Lys Gly Met Leu Pro Asp Pro Lys Asn Val His
        195                 200                 205

Ile Phe Val Ser Trp Met Ile Ala Gln Ser Val Thr Ala Val Ala Gly
    210                 215                 220

Leu Leu Ser Tyr Pro Phe Asp Thr Val Arg Arg Arg Met Met Met Gln
225                 230                 235                 240

Ser Gly Arg Lys Gly Ala Asp Ile Met Tyr Thr Gly Thr Val Asp Cys
                245                 250                 255

Trp Arg Lys Ile Ala Lys Asp Glu Gly Ala Lys Ala Phe Phe Lys Gly
            260                 265                 270

Ala Trp Ser Asn Val Leu Arg Gly Met Gly Gly Ala Phe Val Leu Val
        275                 280                 285

Leu Tyr Asp Glu Ile Lys Lys Tyr Val
    290                 295

```
<210> SEQ ID NO 48
<211> LENGTH: 298
```

```
<212> TYPE: PRT
<213> ORGANISM: Homo sapien

<400> SEQUENCE: 48

Met Thr Asp Ala Ala Leu Ser Phe Ala Lys Asp Phe Leu Ala Gly Gly
 1               5                  10                  15

Val Ala Ala Ile Ser Lys Thr Ala Val Ala Pro Ile Glu Arg Val
            20                  25                  30

Lys Leu Leu Leu Gln Val Gln His Ala Ser Lys Gln Ile Thr Ala Asp
             35                  40                  45

Lys Gln Tyr Lys Gly Ile Ile Asp Cys Val Val Arg Ile Pro Lys Glu
 50                  55                  60

Gln Glu Val Leu Ser Phe Trp Arg Gly Asn Leu Ala Asn Val Ile Arg
 65                  70                  75                  80

Tyr Phe Pro Thr Gln Ala Leu Asn Phe Ala Phe Lys Asp Lys Tyr Lys
                 85                  90                  95

Gln Ile Phe Leu Gly Gly Val Asp Lys Arg Thr Gln Phe Trp Arg Tyr
            100                 105                 110

Phe Ala Gly Asn Leu Ala Ser Gly Gly Ala Ala Gly Ala Thr Ser Leu
            115                 120                 125

Cys Phe Val Tyr Pro Leu Asp Phe Ala Arg Thr Arg Leu Ala Ala Asp
130                 135                 140

Val Gly Lys Ala Gly Ala Glu Arg Glu Phe Arg Gly Leu Gly Asp Cys
145                 150                 155                 160

Leu Val Lys Ile Tyr Lys Ser Asp Gly Ile Lys Gly Leu Tyr Gln Gly
                165                 170                 175

Phe Asn Val Ser Val Gln Gly Ile Ile Ile Tyr Arg Ala Ala Tyr Phe
            180                 185                 190

Gly Ile Tyr Asp Thr Ala Lys Gly Met Leu Pro Asp Pro Lys Asn Thr
            195                 200                 205

His Ile Val Ile Ser Trp Met Ile Ala Gln Thr Val Thr Ala Val Ala
        210                 215                 220

Gly Leu Thr Ser Tyr Pro Phe Asp Thr Val Arg Arg Arg Met Met Met
225                 230                 235                 240

Gln Ser Gly Arg Lys Gly Thr Asp Ile Met Tyr Thr Gly Thr Leu Asp
                245                 250                 255

Cys Trp Arg Lys Ile Ala Arg Asp Glu Gly Gly Lys Ala Phe Phe Lys
                260                 265                 270

Gly Ala Trp Ser Asn Val Leu Arg Gly Met Gly Gly Ala Phe Val Leu
            275                 280                 285

Val Leu Tyr Asp Glu Ile Lys Lys Tyr Thr
            290                 295

<210> SEQ ID NO 49
<211> LENGTH: 298
<212> TYPE: PRT
<213> ORGANISM: Homo sapien

<400> SEQUENCE: 49

Met Thr Glu Gln Ala Ile Ser Phe Ala Lys Asp Phe Leu Ala Gly Gly
 1               5                  10                  15

Ile Ala Ala Ala Ile Ser Lys Thr Ala Val Ala Pro Ile Glu Arg Val
            20                  25                  30

Lys Leu Leu Leu Gln Val Gln His Ala Ser Lys Gln Ile Ala Ala Asp
             35                  40                  45
```

```
                        -continued

Lys Gln Tyr Lys Gly Ile Val Asp Cys Ile Val Arg Ile Pro Lys Glu
         50                  55                  60

Gln Gly Val Leu Ser Phe Trp Arg Gly Asn Leu Ala Asn Val Ile Arg
 65                  70                  75                  80

Tyr Phe Pro Thr Gln Ala Leu Asn Phe Ala Phe Lys Asp Lys Tyr Lys
                 85                  90                  95

Gln Ile Phe Leu Gly Val Asp Lys His Thr Gln Phe Trp Arg Tyr
             100                 105                 110

Phe Ala Gly Asn Leu Ala Ser Gly Gly Ala Ala Gly Ala Thr Ser Leu
             115                 120                 125

Cys Phe Val Tyr Pro Leu Asp Phe Ala Arg Thr Arg Leu Ala Ala Asp
             130                 135                 140

Val Gly Lys Ser Gly Thr Glu Arg Glu Phe Arg Gly Leu Gly Asp Cys
145                 150                 155                 160

Leu Val Lys Ile Thr Lys Ser Asp Gly Ile Arg Gly Leu Tyr Gln Gly
                 165                 170                 175

Phe Ser Val Ser Val Gln Gly Ile Ile Ile Tyr Arg Ala Ala Tyr Phe
             180                 185                 190

Gly Val Tyr Asp Thr Ala Lys Gly Met Leu Pro Asp Pro Lys Asn Thr
             195                 200                 205

His Ile Val Val Ser Trp Met Ile Ala Gln Thr Val Thr Ala Val Ala
             210                 215                 220

Gly Val Val Ser Tyr Pro Phe Asp Thr Val Arg Arg Arg Met Met Met
225                 230                 235                 240

Gln Ser Gly Arg Lys Gly Ala Asp Ile Met Tyr Thr Gly Thr Val Asp
                 245                 250                 255

Cys Trp Arg Lys Ile Phe Arg Asp Glu Gly Gly Lys Ala Phe Phe Lys
                 260                 265                 270

Gly Ala Trp Ser Asn Val Leu Arg Gly Met Gly Gly Ala Phe Val Leu
             275                 280                 285

Val Leu Tyr Asp Glu Leu Lys Lys Val Ile
290                 295

<210> SEQ ID NO 50
<211> LENGTH: 4
<212> TYPE: PRT
<213> ORGANISM: Artificial Sequence
<220> FEATURE:
<223> OTHER INFORMATION: Synthetic peptide

<400> SEQUENCE: 50

Tyr Val Ala Asp
 1

<210> SEQ ID NO 51
<211> LENGTH: 5
<212> TYPE: PRT
<213> ORGANISM: Homo sapien

<400> SEQUENCE: 51

Pro Ser Ser Ser Met
 1               5

<210> SEQ ID NO 52
<211> LENGTH: 6
<212> TYPE: PRT
<213> ORGANISM: Homo sapien

<400> SEQUENCE: 52
```

```
Gly Ser Pro Gly Ile Leu
1               5

<210> SEQ ID NO 53
<211> LENGTH: 4
<212> TYPE: PRT
<213> ORGANISM: Homo sapien

<400> SEQUENCE: 53

Pro Ser Ser Ser
1

<210> SEQ ID NO 54
<211> LENGTH: 7
<212> TYPE: PRT
<213> ORGANISM: Homo sapien

<400> SEQUENCE: 54

Gly Ser Pro Gly Ile Leu Met
1               5

<210> SEQ ID NO 55
<211> LENGTH: 8
<212> TYPE: PRT
<213> ORGANISM: Artificial Sequence
<220> FEATURE:
<223> OTHER INFORMATION: Epitope tag

<400> SEQUENCE: 55

Asp Tyr Lys Asp Asp Asp Asp Lys
1               5

<210> SEQ ID NO 56
<211> LENGTH: 8
<212> TYPE: PRT
<213> ORGANISM: Artificial Sequence
<220> FEATURE:
<223> OTHER INFORMATION: Epitope tag

<400> SEQUENCE: 56

Asp Leu Tyr Asp Asp Asp Asp Lys
1               5

<210> SEQ ID NO 57
<211> LENGTH: 897
<212> TYPE: DNA
<213> ORGANISM: Homo sapiens

<400> SEQUENCE: 57
atgacagatg ccgctgtgtc cttcgccaag gacttcctgg caggtggagt ggccgcagcc      60
atctccaaga cggcggtagc gcccatcgag cgggtcaagc tgctgctgca ggtgcagcat     120
gccagcaagc agatcactgc agataagcaa tacaaaggca ttatagactg cgtggtccgt     180
attcccaagg agcagggagt tctgtccttc tggcgcggta acctggccaa tgtcatcaga     240
tacttcccca cccaggctct taacttcgcc ttcaaagata aatacaagca gatcttcctg     300
ggtggtgtgg acaagagaac ccagtttttgg ctctactttg cagggaatct ggcatcgggt     360
ggtgccgcag gggccacatc cctgtgtttt gtgtaccctc ttgattttgc ccgtacccgt     420
ctagcagctg atgtgggtaa agctggagct gaaagggaat tccgaggcct cggtgactgc     480
ctgggtaaga tctacaaaatc tgatgggatt aagggcctgt accaaggctt taacgtgtct     540
gtgcagggta ttatcatcta ccgagccgcc tacttcggta tctatgacac tgcaaaggga     600
```

```
atgcttccgg atcccaagaa cactcacatc gtcatcagct ggatgatcgc acagactgtc      660
actgctgttg ccgggttgac ttcctatcca tttgacactg ttcgccgccg catgatgatg      720
cagtcagggc gcaaaggaac tgacatcatg tacacaggca cgcttgactg ctggcggaag      780
attgctcgtg atgaaggagg caaagctttt ttcaagggtg catggtccaa tgttctcaga      840
ggcatgggtg gtgcttttgt gcttgtcttg tatgatgaaa tcaagaagta cacataa        897
```

We claim:

1. A method of identifying an agent that alters binding of an adenine nucleotide translocator polypeptide to a cyclophilin polypeptide, comprising:
  (a) contacting, in the absence and presence of a candidate agent, (i) a first isolated recombinant polypeptide comprising a cyclphilin polypeptide or variant thereof with (ii) a sample comprising a second isolated recombinant polypeptide that comprises a recombinant human adenine nucleotide translocator polypeptide or variant thereof, under conditions and for a time sufficient to permit the cyclophilin polypeptide, the adenine nucleotide translocator polypeptide and the candidate agent to interact; and
  (b) comparing a level of binding of the first isolated recombinant polypeptide to the second isolated recombinant polypeptide in the absence of the candidate agent to the level of binding of the first isolated recombinant polypeptide to the second isolated recombinant polypeptide in the presence of the candidate agent, wherein a decreased level of binding in the presence of the agent indicates an agent that inhibits binding of an adenine nucleotide translocator polypeptide to a cyclophilin polypeptide and wherein an increased level of binding in the presence of the agent indicates an agent that enhances binding of an adenine nucleotide translocator polypeptide to a cyclophilin polypeptide, and therefrom identifying an agent that alters binding of an adenine nucleotide translocator polypeptide to a cyclophilin polypeptide.

2. The method of claim 1 wherein at least one of the first and second isolated recombinant polypeptides is a fusion polypeptide.

3. The method of claim 1 wherein the first isolated recombinant polypeptide comprises a human cyclophilin D polypeptide that is fused to an additional polypeptide, wherein the additional polypeptide is other than glutathione-S-transferase.

4. The method of claim 1 wherein the cyclophilin polypeptide is selected from the group consisting of human cyclophilin A, human cyclophilin B, human cyclophilin C and human Cyp-60.

5. The method of claim 1 wherein the first isolated recombinant polypeptide comprises a cyclophilin polypeptide fused to an additional polypeptide that is selected from the group consisting of polyhistidine, polylysine, a haemagglutinin epitope tag, a DLYDDDDK (SEQ ID NO: 56) epitope tag, a DYKDDDDK (SEQ ID NO: 55) epitope tag, a Myc epitope polypeptide, a FLASH peptide, an immunoglobulin constant region polypeptide, streptavidin, a green fluorescent protein polypeptide, an aequorin polypeptide, a glutathione-S-transferase polypeptide and a Staphylococcus aureus protein A polypeptide.

6. The method of claim 1 wherein the first isolated recombinant polypeptide is detectably labeled with a linked reporter group.

7. The method of claim 1 wherein the first isolated recombinant polypeptide comprises a cyclophilin polypeptide fused to an additional polypeptide that is polylysine and the second isolated recombinant polypeptide comprises a recombinant human adenine nucleotide tanslocator polypeptide fused to an XPRESS™ epitope tag.

8. The method of claim 7 wherein the first isolated recombinant polypeptide is detectably labeled with a linked reporter group.

9. The method of either claim 6 or claim 8 wherein the linked reporter group is selected from the group consisting of a radioactive reporter group, a dye, an enzyme, a ligand, a receptor, a protease recognition sequence, a luminescent reporter group and a fluorescent reporter group.

10. The method of claim 1 wherein the sample which comprises the second isolated recombinant polypeptide comprises at least one isolated mitochondrion.

11. The method of claim 1 wherein the sample which comprises the second isolated recombinant polypeptide comprises at least one submitochondrial particle.

12. The method of claim 1 wherein the sample which comprises the second isolated recombinant polypeptide is immobilized on a solid support.

13. The method of claim 1 wherein the second isolated recombinant polypeptide comprises a human adenine nucleotide translocator polypeptide or variant thereof that is fused to an additional polypeptide selected from the group consisting of polyhistidine, polylysine, a haemagglutinin epitope tag, a DLYDDDDK (SEQ ID NO: 56) epitope tag, a DYKDDDDK (SEQ ID NO: 55) epitope tag, a Myc epitope polypeptide, a FLASH peptide, an immunoglobulin constant region polypeptide, streptavidin, a green fluorescent protein polypeptide, an aequorin polypeptide, a glutathione-S-transferase polypeptide and a Staphylococcus aureus protein A polypeptide.

14. The method of claim 1 wherein the step of comparing binding levels comprises detection of a detection reagent that specifically binds to at least one of the polypeptides selected from the group consisting of the first isolated recombinant polypeptide and the second isolated recombinant polypeptide.

15. The method of claim 14 wherein the detection reagent is an antibody.

16. The method of claim 15 wherein the second isolated recombinant polypeptide comprises a human adenine nucleotide translocator polypeptide or variant thereof that is fused to a polypeptide selected from the group consisting of a DLYDDDDK (SEQ ID NO: 56) epitope tag and a DYKDDDDK (SEQ ID NO: 55) epitope tag, and wherein the antibody specifically binds to at least one polypeptide selected from the group consisting of the human adenine nucleotide translocator polypeptide, the XPRESS™ epitope tag and the FLAG® epitope tag.

17. The method of claim 1 wherein the first isolated recombinant polypeptide comprises human cyclophilin D and wherein the sample which comprises the second isolated recombinant polypeptide comprises at least one submitochondrial particle isolated from a *T. ni* cell that expresses a recombinant human adenine nucleotide translocator-3 polypeptide fused to a DLYDDDDK (SEQ ID NO: 56) epitope tag.

* * * * *

UNITED STATES PATENT AND TRADEMARK OFFICE
CERTIFICATE OF CORRECTION

PATENT NO. : 6,797,467 B1
DATED : September 28, 2004
INVENTOR(S) : Anne N. Murphy et al.

It is certified that error appears in the above-identified patent and that said Letters Patent is hereby corrected as shown below:

Column 115,
Line 20, "cyclphilin" should read as -- cyclophilin --.

Column 116,
Line 21, "tanslocator" should read as -- transloctor --.

Column 117,
Line 5, "EXPRESS™" should read as -- DLYDDDDK [SEQ ID NO:56] --.
Line 6, "FLAG®" should read as -- DYKDDDDK [SEQ ID NO:55] --.

Signed and Sealed this

Twenty-third Day of August, 2005

JON W. DUDAS
*Director of the United States Patent and Trademark Office*